United States Patent [19]
Christianson et al.

[11] Patent Number: 5,985,639
[45] Date of Patent: Nov. 16, 1999

[54] MUTANT PROTEOLYTIC ENZYMES AND METHOD OF PRODUCTION

[75] Inventors: Teresa Christianson, Cotati; Dean Goddette, Rohnert Park; Beth Frances Ladin, Santa Rosa; Maria R. Lau, Fairfield; Christian Paech, Santa Rosa; Robert B. Reynolds, Santa Rosa; Charles R. Wilson, Santa Rosa; Shiow-Shong Yang, Santa Rosa, all of Calif.

[73] Assignee: Henkel Kommanditgesellschaft auf Aktien, Duesseldorf, Germany

[21] Appl. No.: 08/618,446

[22] Filed: Mar. 19, 1996

Related U.S. Application Data

[62] Division of application No. 08/254,021, Jun. 2, 1994, Pat. No. 5,500,364, which is a division of application No. 07/706,691, May 29, 1991, Pat. No. 5,340,735.

[51] Int. Cl.⁶ .............. C12N 9/54; C12N 15/57; C12N 15/62; C12N 15/75
[52] U.S. Cl. .............. 435/221; 435/69.1; 435/69.7; 435/220; 435/252.31; 435/320.1; 435/471; 536/23.2; 536/23.5
[58] Field of Search .................. 435/220, 221, 435/69.1, 69.7, 172.3, 252.31, 320.1, 471; 536/23.2, 23.5

[56] References Cited

U.S. PATENT DOCUMENTS

| | | | |
|---|---|---|---|
| 4,760,025 | 7/1988 | Estell et al. | 510/392 |
| 4,853,871 | 8/1989 | Pantoliano et al. | 364/496 |
| 4,908,773 | 3/1990 | Pantoliano et al. | 364/496 |
| 4,914,031 | 4/1990 | Zukowski et al. | 435/222 |
| 5,352,604 | 10/1994 | Wilson et al. | 435/221 |
| 5,700,676 | 12/1997 | Bott et al. | 435/221 |
| 5,741,694 | 4/1998 | Hastrup et al. | 435/221 |
| 5,763,257 | 6/1998 | Bott et al. | 435/221 |
| 5,801,038 | 9/1998 | Bott et al. | 435/221 |

FOREIGN PATENT DOCUMENTS

| | | |
|---|---|---|
| 0130756 | 1/1985 | European Pat. Off. . |
| 0247647 | 12/1987 | European Pat. Off. . |
| 0251446 | 1/1988 | European Pat. Off. . |
| 0260105 | 3/1988 | European Pat. Off. . |
| 0328229 | 8/1989 | European Pat. Off. . |
| 1137972 | 5/1989 | Japan . |
| 87 04461 | 7/1987 | WIPO . |
| 87 05050 | 8/1987 | WIPO . |
| 88 07578 | 10/1988 | WIPO . |
| 88 08028 | 10/1988 | WIPO . |
| 88 08033 | 10/1988 | WIPO . |
| 89-06279 | 7/1989 | WIPO . |
| 89-09819 | 10/1989 | WIPO . |
| 89-09830 | 10/1989 | WIPO . |
| WO 91-02792 | 3/1991 | WIPO . |

OTHER PUBLICATIONS

"Construction and characterization of new coliphage M13 cloning vectors", Hines et al., Gene, 11:207–218 (1980).

Oligonucleotide–directed mutagenesis using M13–derived vectors . . . , Zoller et al., Nucleic Acids Research, vol. 10, 6487–6500 (1982).

Construction of improved M13 vectors using oligodeoxy-nucleotide–directed mutagenesis, Norrander et al., Gene, 26, 101–106 (1983).

(List continued on next page.)

*Primary Examiner*—Ponnathapu Achutamurthy
*Assistant Examiner*—William W. Moore
*Attorney, Agent, or Firm*—Wayne C. Jaeschke; John E. Drach; Jeffrey S. Steen

[57] ABSTRACT

Mutant *B. lentus* DSM 5483 proteases are derived by the replacement of at least one amino acid residue of the mature form of the *B. lentus* DSM 5483 alkaline protease. The mutant proteases are expressed by genes which are mutated by site-specific mutagenesis. The amino acid sites selected for replacement are identified by means of a computer based method which compares the three dimensional structure of the wild-type protease and a reference protease.

48 Claims, 18 Drawing Sheets

OTHER PUBLICATIONS

"Improvement of oligonucleotide–directed site–specific mutagenesis using double–stranded plasmid DNA", Morinaga et al., Bio/Technology 2:636–639 (1984).

"The gapped duplex DNA approach to oligonucleotide–directed mutation construction", Kramer et al., Nucleic Acids Research, 12:9441–9456 (1984).

"Improved oligonucleotide site–directed mutagenesis using M13 vectors", Carter et al., Nucleic Acids Research, 13:4431–4443 (1985).

"Rapid and efficient site–specific mutagenesis without phenotypic selection", Kunkel et al., Proc. Natl. Acad. Sci. USA, 82:488–492 (1985).

"Site–directed mutagenesis and the role of the oxyanion hole in subtilisin", Bryan et al., Proc. Natl. Acad. Sci. USA, 83:3743–3745 (1986).

Replacement of the *Bacillus subtilis* Subtilisin Structural Gene with an In–Vitro–Derived Deletion Mutation, Stahl et al., J. Bacteriol. 158:411–418 (1984).

"Genes for Alkaline Protease and Neutral Protease . . . Mature Protein", Vasantha et al., J. Bacteriol, 159:811–819 (1984).

Cloning, sequencing and expression of subtilisin Carlsberg from *Bacillus Lincheniformis*, Jacobs et al., Nucleic Acids Research, 13:8913–8926 (1985).

Determination of the Complete Amino–Acid Sequence of Subtilisin DY . . . Carlsberg and Amylosaccahriticus, Nedkov et al., Biol. Chem. Hoppe Seyler, 366:421–430 (1985).

"Subtilisin Amylosacchariticus", Kurihara et al., Journal of Biological Chemistry, 247:5619–5631 (1972).

"Complete amino acid sequence of alkaline mesentericopeptidase", Svendsen et al., FEBS Lett., 196:228–232 (1986).

"Complete primary structure of thermitase from *Thermoactinomyces vulgaris* . . . " Meloun et al., FEBS Lett. 183:195–200 (1985).

Proteinase K from *Tritirachium album* Limber, Jany et al., Biol. Chem Hoppe–Seyler, 366:485–492, (1985).

"Designing substrate specificity by protein engineering of electrostatic interactions", Wells et al., Proc. Natl. Acad. Sci. USA 84:1219–1223 (1987).

"Crystal Structure of Thermitase at 14A Resolution", Teplyakov et al., J. Mol. Biol., 214:261–279 (1990).

"The Three–dimensional Structure of *Bacillus amyloliquefaciens* Subtilisn . . . ", Bott et al., J. Biol. Chem. 263:7895–7906 (1988).

"Refined 1.2 A crystal structure of the complex formed between subtilisn Carlsberg . . . interaction with subtilisin", Bode et al., EMBO Journal, 5:813–818 (1986).

"Cleavage at Asn–Gly Bonds with Hydroxylamine", Bornstein et al., Methods Enzymol. 47:132–145 (1977).

"The Effect on Subtilisn Activity of Oxidizing a Methionine Residue", Stauffer, et al., J. Biol. Chem., 244:5333–5338 (1969).

"Rational modification of enzyme catalysis by engineering surface charge", Russell et al., Nature, 328:496–500 (1987).

"Electrostatic Effects on Modification of Charged Groups . . . by Protein Engineering" Russell et al., J. Mol. Biol., 193:803–813 (1987).

Enhanced protein thermostability for site–directed mutations . . . , Matthews et al., Proc. Natl. Acad. Sci., 84:6663–6667 (1987).

"Influence of Interior Packing and Hydrophobicity on the Stability of a Protein", Sandberg et al., Science, 245:54–57 (1989).

"Engineering Protein Thermal Stability . . . Substitutions in α–Helices", Menendez–Arias et al., J. Mol. Biol. 206:397–406 (1989).

"Contributioin of hydrophobic interactions to protein stability", Kellis et al., Nature, 333:784–786 (1988).

"Structural invariants in protein folding", Cyrus Chothia, Nature, 254:304–308, (1975).

"Deciphering the Message in Protein Sequences: Tolerance to Amino Acid Substitutions", Bowie et al., Science, 247:1306–1310 (1990).

Repacking protein interiors, Sandberg et al., Trends Biotechnol., 9:59–63 (1991).

"Efficient oligonucleotide–directed construction of mutations . . . using alternating selectable markers", Stanssens, Nucleic Acids Res., 17:4441–4454 (1989).

Construction of a *Bacillus subtilis* Double Mutant Deficient in Extracellular . . . Proteases, Kawamura et al., J. Bacteriol., 160:442–444 (1984).

"Areas, Volumes, Packaging, and Protein Structure", F. M. Richards, Ann. Rev. Biophys. Bioeng., 6:151–176 (1977).

A Computational Procedure for Determining energetically Favorable Binding Sites . . . Macromolecules, P. J. Goodford, J. Med. Chem., 28:849–857 (1985).

"Charakterisierung einer Protease aus *Thermoactinomyces vulgaris* (Thermitase)", Froemmel, et al., Acta biol. med. germ., 37:1193–1204 (1978).

"Optimal alignments in linear space", Myers et al., Comput. Applic. Biosci., 4:11–17 (1988).

"Improved tools for biological sequence comparison", Pearson et al., Proc. Natl. Acad. Sci USA, 85:2444–2448, (1988).

"Knowledge based modelling of homologous proteins, part I: . . . multiple structures", Sutcliffe et al., Protein Eng., 1:377–384 (1987).

"A solution for the best rotation to relate two sets of vectors", W. Kabsch., Acta Cryst., A32:922–923 (1976).

"Suggestions for 'Safe ' Residue Substitutions in Site–directed Mutagenesis", Bordo, et al., J. Mol. Biol., 217:721–729 (1991).

"Use of Packing Criteria in the Enumeration of Allowed Sequences for Different Structural Classes", Ponder et al., J. Mol. Biol., 193:775–791 (1987).

"Engineering Thermostability in Subtilisn BPN' In Vitro Mutagenesis", Rollence et al., Critical Rev. Biotechnol. 8:217–224, (1988).

The Protein Data Bank: A Computer–based Archival File for Macromolecular Structures, Bernstein et al., J. Mol. Biol. 112:535–542, (1977).

Inorganic Phosphate Determination in the Presence of a Labile Organic Phosphate: . . . Phosphatase Activity, Black et al., Anal. Biochem. 135:233–238 (1983).

"Somanase Project", P. Bryan., Office of Naval Research, Document No. AD–A182 669 (1987).

"Proteases of Enhanced Stability: Characterization of a Thermostable Variant of Subtilisn", Bryan et al., Proteins: Struct. Funct. Genet. 1:326–334 (1986).

"Engineering Enzyme Specificity by 'Substrate–Assisted Catalysis'", Carter et al., Science, 237:394–399 (1987).

"Improvement in the alkaline stability of subtilisin using an efficient . . . screening procedure", Cunningham et al., Protein Eng. 1:319–325 (1987).

"A Sensitive New Substrate for Chymotrypsin", DelMar et al., Anal. Biochem., 99:316–320 (1979).

"Engineering an Enzyme by Site–directed Mutagenesis to be Resistant to Chemical Oxidation", J. Biol. Chem. 260:6518–6521 (1985).

"Determination of Serum Proteins by Means of the Biuret Reaction", Gornall et al., J. Biol. Chem. 177:751–766 (1948).

"Biological Function for 6–Methyladenine Residues in the DNA of *Escherichia coli* K12", Marinus et al., J. Mol. Biol., 85:309–322 (1974).

"Protein Engineering of Disulfide Bonds in Subtilisin BPN", Mitchinson et al., Biochemistry, 28:4807–4815 (1989).

Protein Engineering of Subtilisin BPN': Enhanced Stabilization through . . . Disulfide Bond:, Pantoliano et al., Biochemistry, 26:2077–2082 (1987).

"Large Increases in General Stability for Subtilisin BPN'through . . . Free Energy of Unfolding", Pantoliano e al., Biochemistry, 28:7205–7213 (1989).

"The Engineering of Binding Affinity at Metal Ion Binding Sites . . . Subtilisin as a Test Case", Pantoliano et al., Biochemistry, 27:8311–8317 (1988).

"Mutant Subtilisn E with Enhanced Protease Activity Obtained by Site–directed Mutagenesis", Takagi et al., J. Biol. Chem. 263:19592–19596 (1988).

"The Role of Pro–239 in the Catalysis and Heat Stability of Subtilisn E", Takagi et al., J. Biochem. 105:953–956 (1989).

"Importance of hydrogen–bond formation in stabilizing the transition state of subtilisin", Wells et al., Phil. Trans. R. Soc. Lond., A317:415–423 (1986).

"Recruitment of substrate–specificity properties from one enzyme . . . by protein engineering", Wells et al., Proc. Natl. Acad. Sci. USA, 84:5167–5171 (1987).

"In Vivo Formation and Stability of Engineered Disulfide Bonds in Subtilisin", Wells et al., J. Biol. Chem. 261:6564–6570 (1986).

"DNA mismatch–repair in *Escherichia coli* counteracting the hydrolytic deamination of 5–methyl–cytosine residues", Zell et al., EMBO J. 6:1809–1815 (1987).

Society for Industrial Microbiology Annual Meeting, Abstract P60, B. Ladin, et al. (1990).

Atlas of Protein Sequence and Structure, vol. 5, Supplement 2 (1976) (Dayhoff, M.O., ed., Natl. Biomed. Res. Found., Silver Springs, MD).

Betzel, C., et al., Journal of Molecular Biology, vol. 204, "Crystallization and preliminary X–ray diffraction studies of an alkaline protease from *Bacillus lentus*", pp. 803–804, 1988.

| | | | | | | | | | | | |
|---|---|---|---|---|---|---|---|---|---|---|---|
| 1 | GLY | C | 27.985 | 27.065 | 7.578 | 8 | ILE | O | 29.238 | 35.790 | 21.181 |
| 1 | GLY | O | 26.834 | 26.692 | 7.822 | 9 | SER | N | 28.255 | 36.591 | 19.284 |
| 1 | GLY | N | 27.785 | 25.660 | 5.657 | 9 | SER | CA | 29.270 | 37.572 | 19.075 |
| 1 | GLY | CA | 28.517 | 26.825 | 6.143 | 9 | SER | CB | 29.158 | 38.161 | 17.652 |
| 2 | GLN | N | 28.745 | 27.585 | 8.522 | 9 | SER | OG | 29.411 | 37.107 | 16.718 |
| 2 | GLN | CA | 28.205 | 27.868 | 9.851 | 9 | SER | C | 29.191 | 38.684 | 20.145 |
| 2 | GLN | CB | 29.179 | 27.265 | 10.835 | 9 | SER | O | 30.236 | 39.113 | 20.660 |
| 2 | GLN | CG | 28.905 | 27.589 | 12.287 | 10 | ARG | N | 27.977 | 39.085 | 20.540 |
| 2 | GLN | CD | 29.834 | 26.805 | 13.151 | 10 | ARG | CA | 27.775 | 40.132 | 21.537 |
| 2 | GLN | OE1 | 29.476 | 25.685 | 13.540 | 10 | ARG | CB | 26.288 | 40.423 | 21.686 |
| 2 | GLN | NE2 | 31.008 | 27.317 | 13.461 | 10 | ARG | CG | 25.946 | 41.656 | 22.562 |
| 2 | GLN | C | 28.045 | 29.384 | 10.049 | 10 | ARG | CD | 26.666 | 42.953 | 22.101 |
| 2 | GLN | O | 28.927 | 30.159 | 9.642 | 10 | ARG | NE | 26.378 | 43.300 | 20.705 |
| 3 | SER | N | 26.940 | 29.781 | 10.693 | 10 | ARG | CZ | 25.394 | 44.138 | 20.338 |
| 3 | SER | CA | 26.568 | 31.160 | 10.999 | 10 | ARG | NH1 | 25.226 | 44.365 | 19.048 |
| 3 | SER | CB | 25.036 | 31.390 | 10.712 | 10 | ARG | NH2 | 24.604 | 44.767 | 21.215 |
| 3 | SER | OG | 24.576 | 30.913 | 9.455 | 10 | ARG | C | 28.351 | 39.782 | 22.893 |
| 3 | SER | C | 26.815 | 31.424 | 12.488 | 10 | ARG | O | 28.942 | 40.673 | 23.476 |
| 3 | SER | O | 26.464 | 30.580 | 13.314 | 11 | VAL | N | 28.222 | 38.532 | 23.377 |
| 4 | VAL | N | 27.371 | 32.570 | 12.897 | 11 | VAL | CA | 28.862 | 38.186 | 24.642 |
| 4 | VAL | CA | 27.534 | 32.913 | 14.309 | 11 | VAL | CB | 28.127 | 37.003 | 25.339 |
| 4 | VAL | CB | 28.860 | 33.625 | 14.552 | 11 | VAL | CG1 | 26.664 | 37.416 | 25.538 |
| 4 | VAL | CG1 | 29.008 | 33.965 | 16.045 | 11 | VAL | CG2 | 28.227 | 35.723 | 24.530 |
| 4 | VAL | CG2 | 30.006 | 32.739 | 14.035 | 11 | VAL | C | 30.343 | 37.832 | 24.471 |
| 4 | VAL | C | 26.397 | 33.869 | 14.655 | 11 | VAL | O | 31.021 | 37.393 | 25.404 |
| 4 | VAL | O | 26.344 | 34.990 | 14.097 | 12 | GLN | N | 30.868 | 37.944 | 23.261 |
| 5 | PRO | N | 25.384 | 33.471 | 15.449 | 12 | GLN | CA | 32.288 | 37.745 | 22.957 |
| 5 | PRO | CD | 25.140 | 32.114 | 15.924 | 12 | GLN | CB | 33.129 | 38.763 | 23.772 |
| 5 | PRO | CA | 24.313 | 34.393 | 15.856 | 12 | GLN | CG | 32.773 | 40.196 | 23.319 |
| 5 | PRO | CB | 23.404 | 33.524 | 16.740 | 12 | GLN | CD | 33.643 | 41.252 | 23.997 |
| 5 | PRO | CG | 23.629 | 32.110 | 16.189 | 12 | GLN | OE1 | 34.842 | 41.403 | 23.753 |
| 5 | PRO | C | 24.823 | 35.677 | 16.538 | 12 | GLN | NE2 | 33.145 | 42.035 | 24.926 |
| 5 | PRO | O | 25.816 | 35.601 | 17.282 | 12 | GLN | C | 32.806 | 36.330 | 23.186 |
| 6 | TRP | N | 24.126 | 36.804 | 16.302 | 12 | GLN | O | 33.978 | 36.104 | 23.557 |
| 6 | TRP | CA | 24.597 | 38.070 | 16.867 | 13 | ALA | N | 31.938 | 35.350 | 22.940 |
| 6 | TRP | CB | 23.589 | 39.231 | 16.567 | 13 | ALA | CA | 32.333 | 33.978 | 23.095 |
| 6 | TRP | CG | 22.313 | 39.360 | 17.414 | 13 | ALA | CB | 31.189 | 33.004 | 22.890 |
| 6 | TRP | CD2 | 22.238 | 40.080 | 18.588 | 13 | ALA | C | 33.418 | 33.589 | 22.084 |
| 6 | TRP | CE2 | 20.905 | 39.872 | 18.955 | 13 | ALA | O | 34.293 | 32.789 | 22.477 |
| 6 | TRP | CE3 | 23.091 | 40.874 | 19.364 | 14 | PRO | N | 33.507 | 34.053 | 20.808 |
| 6 | TRP | CD1 | 21.120 | 38.755 | 17.097 | 14 | PRO | CD | 32.522 | 34.799 | 20.020 |
| 6 | TRP | NE1 | 20.274 | 39.089 | 18.047 | 14 | PRO | CA | 34.622 | 33.646 | 19.943 |
| 6 | TRP | CZ2 | 20.485 | 40.458 | 20.142 | 14 | PRO | CB | 34.311 | 34.283 | 18.601 |
| 6 | TRP | CZ3 | 22.638 | 41.455 | 20.536 | 14 | PRO | CG | 32.806 | 34.270 | 18.606 |
| 6 | TRP | CH2 | 21.339 | 41.249 | 20.918 | 14 | PRO | C | 35.977 | 34.034 | 20.525 |
| 6 | TRP | C | 24.859 | 38.028 | 18.378 | 14 | PRO | O | 36.900 | 33.216 | 20.393 |
| 6 | TRP | O | 25.812 | 38.610 | 18.854 | 15 | ALA | N | 36.096 | 35.170 | 21.257 |
| 7 | GLY | N | 24.056 | 37.299 | 19.142 | 15 | ALA | CA | 37.383 | 35.545 | 21.881 |
| 7 | GLY | CA | 24.171 | 37.250 | 20.597 | 15 | ALA | CB | 37.253 | 36.887 | 22.612 |
| 7 | GLY | C | 25.488 | 36.591 | 21.015 | 15 | ALA | C | 37.837 | 34.470 | 22.892 |
| 7 | GLY | O | 26.135 | 36.993 | 22.000 | 15 | ALA | O | 39.024 | 34.129 | 22.980 |
| 8 | ILE | N | 25.911 | 35.557 | 20.242 | 16 | ALA | N | 36.899 | 33.826 | 23.591 |
| 8 | ILE | CA | 27.125 | 34.811 | 20.543 | 16 | ALA | CA | 37.248 | 32.758 | 24.508 |
| 8 | ILE | CB | 27.250 | 33.554 | 19.559 | 16 | ALA | CB | 36.057 | 32.436 | 25.368 |
| 8 | ILE | CG2 | 28.525 | 32.760 | 19.882 | 16 | ALA | C | 37.632 | 31.505 | 23.705 |
| 8 | ILE | CG1 | 26.016 | 32.625 | 19.654 | 16 | ALA | O | 38.587 | 30.787 | 24.026 |
| 8 | ILE | CD | 25.683 | 32.107 | 21.080 | 17 | HIS | N | 36.927 | 31.180 | 22.610 |
| 8 | ILE | C | 28.303 | 35.772 | 20.363 | 17 | HIS | CA | 37.206 | 29.941 | 21.872 |

FIG. 1A

| | | | | | | | | | | | |
|---|---|---|---|---|---|---|---|---|---|---|---|
| 17 | HIS | CB | 36.283 | 29.667 | 20.715 | 27 | LYS | N | 29.799 | 19.815 | 32.589 |
| 17 | HIS | CG | 34.810 | 29.669 | 21.066 | 27 | LYS | CA | 28.459 | 19.291 | 32.434 |
| 17 | HIS | CD2 | 33.823 | 29.867 | 20.140 | 27 | LYS | CB | 28.206 | 18.148 | 33.370 |
| 17 | HIS | ND1 | 34.240 | 29.557 | 22.260 | 27 | LYS | CG | 29.146 | 17.001 | 33.191 |
| 17 | HIS | CE1 | 32.932 | 29.701 | 22.082 | 27 | LYS | CD | 28.427 | 15.942 | 33.969 |
| 17 | HIS | NE2 | 32.694 | 29.881 | 20.807 | 27 | LYS | CE | 29.530 | 15.137 | 34.529 |
| 17 | HIS | C | 38.557 | 30.109 | 21.246 | 27 | LYS | NZ | 29.022 | 14.047 | 35.345 |
| 17 | HIS | O | 39.290 | 29.114 | 21.115 | 27 | LYS | C | 27.394 | 20.331 | 32.719 |
| 18 | ASN | N | 38.978 | 31.354 | 20.903 | 27 | LYS | O | 27.368 | 20.968 | 33.797 |
| 18 | ASN | CA | 40.320 | 31.583 | 20.379 | 28 | VAL | N | 26.512 | 20.472 | 31.730 |
| 18 | ASN | CB | 40.420 | 32.976 | 19.792 | 28 | VAL | CA | 25.435 | 21.471 | 31.738 |
| 18 | ASN | CG | 39.771 | 33.007 | 18.426 | 28 | VAL | CB | 25.628 | 22.534 | 30.583 |
| 18 | ASN | OD1 | 39.324 | 34.072 | 17.991 | 28 | VAL | CG1 | 24.502 | 23.560 | 30.598 |
| 18 | ASN | ND2 | 39.604 | 31.952 | 17.631 | 28 | VAL | CG2 | 26.989 | 23.220 | 30.749 |
| 18 | ASN | C | 41.377 | 31.382 | 21.454 | 28 | VAL | C | 24.121 | 20.739 | 31.512 |
| 18 | ASN | O | 42.545 | 31.105 | 21.147 | 28 | VAL | O | 23.947 | 20.067 | 30.475 |
| 19 | ARG | N | 41.007 | 31.481 | 22.726 | 29 | ALA | N | 23.203 | 20.933 | 32.446 |
| 19 | ARG | CA | 41.934 | 31.108 | 23.756 | 29 | ALA | CA | 21.900 | 20.311 | 32.385 |
| 19 | ARG | CB | 41.579 | 31.808 | 25.055 | 29 | ALA | CB | 21.478 | 19.832 | 33.763 |
| 19 | ARG | CG | 41.755 | 33.269 | 24.901 | 29 | ALA | C | 20.906 | 21.382 | 31.920 |
| 19 | ARG | CD | 41.327 | 33.963 | 26.212 | 29 | ALA | O | 20.919 | 22.490 | 32.454 |
| 19 | ARG | NE | 41.469 | 35.388 | 26.008 | 30 | VAL | N | 20.038 | 21.127 | 30.938 |
| 19 | ARG | CZ | 40.620 | 36.280 | 26.485 | 30 | VAL | CA | 19.069 | 22.069 | 30.421 |
| 19 | ARG | NH1 | 40.880 | 37.535 | 26.211 | 30 | VAL | CB | 19.123 | 22.097 | 28.835 |
| 19 | ARG | NH2 | 39.567 | 35.963 | 27.217 | 30 | VAL | CG1 | 18.017 | 22.967 | 28.267 |
| 19 | ARG | C | 41.924 | 29.600 | 23.992 | 30 | VAL | CG2 | 20.480 | 22.654 | 28.369 |
| 19 | ARG | O | 42.655 | 29.144 | 24.864 | 30 | VAL | C | 17.731 | 21.519 | 30.928 |
| 20 | GLY | N | 41.166 | 28.766 | 23.312 | 30 | VAL | O | 17.275 | 20.467 | 30.425 |
| 20 | GLY | CA | 41.105 | 27.344 | 23.620 | 31 | LEU | N | 17.155 | 22.192 | 31.928 |
| 20 | GLY | C | 40.056 | 26.959 | 24.682 | 31 | LEU | CA | 15.899 | 21.751 | 32.514 |
| 20 | GLY | O | 40.026 | 25.824 | 25.187 | 31 | LEU | CB | 15.878 | 22.118 | 33.997 |
| 21 | LEU | N | 39.130 | 27.872 | 25.003 | 31 | LEU | CG | 16.523 | 21.135 | 34.997 |
| 21 | LEU | CA | 38.098 | 27.626 | 26.023 | 31 | LEU | CD1 | 18.034 | 21.230 | 34.828 |
| 21 | LEU | CB | 38.012 | 28.796 | 26.984 | 31 | LEU | CD2 | 16.177 | 21.487 | 36.457 |
| 21 | LEU | CG | 39.321 | 29.049 | 27.732 | 31 | LEU | C | 14.832 | 22.501 | 31.724 |
| 21 | LEU | CD1 | 39.370 | 30.463 | 28.219 | 31 | LEU | O | 14.647 | 23.705 | 31.887 |
| 21 | LEU | CD2 | 39.469 | 28.017 | 28.815 | 32 | ASP | N | 14.163 | 21.816 | 30.801 |
| 21 | LEU | C | 36.767 | 27.463 | 25.284 | 32 | ASP | CA | 13.254 | 22.474 | 29.860 |
| 21 | LEU | O | 36.254 | 28.371 | 24.622 | 32 | ASP | CB | 14.173 | 23.197 | 28.850 |
| 22 | THR | N | 36.294 | 26.227 | 25.368 | 32 | ASP | CG | 13.567 | 24.470 | 28.221 |
| 22 | THR | CA | 35.094 | 25.767 | 24.713 | 32 | ASP | OD1 | 14.128 | 25.565 | 28.394 |
| 22 | THR | CB | 35.488 | 24.785 | 23.658 | 32 | ASP | OD2 | 12.549 | 24.352 | 27.538 |
| 22 | THR | OG1 | 36.139 | 23.695 | 24.331 | 32 | ASP | C | 12.331 | 21.405 | 29.226 |
| 22 | THR | CG2 | 36.341 | 25.467 | 22.585 | 32 | ASP | O | 12.057 | 20.382 | 29.870 |
| 22 | THR | C | 34.069 | 25.126 | 25.622 | 33 | THR | N | 11.874 | 21.602 | 27.972 |
| 22 | THR | O | 33.010 | 24.745 | 25.146 | 33 | THR | CA | 10.956 | 20.709 | 27.245 |
| 23 | GLY | N | 34.304 | 24.953 | 26.918 | 33 | THR | CB | 10.237 | 21.562 | 26.131 |
| 23 | GLY | CA | 33.327 | 24.232 | 27.761 | 33 | THR | OG1 | 11.275 | 22.099 | 25.255 |
| 23 | GLY | C | 33.680 | 22.769 | 27.973 | 33 | THR | CG2 | 9.394 | 22.669 | 26.737 |
| 23 | GLY | O | 32.931 | 22.033 | 28.642 | 33 | THR | C | 11.600 | 19.465 | 26.594 |
| 24 | SER | N | 34.808 | 22.329 | 27.403 | 33 | THR | O | 10.948 | 18.766 | 25.806 |
| 24 | SER | CA | 35.218 | 20.939 | 27.546 | 34 | GLY | N | 12.919 | 19.306 | 26.830 |
| 24 | SER | CB | 36.565 | 20.776 | 26.874 | 34 | GLY | CA | 13.720 | 18.216 | 26.294 |
| 24 | SER | OG | 36.819 | 19.378 | 26.828 | 34 | GLY | C | 14.758 | 18.794 | 25.334 |
| 24 | SER | C | 35.310 | 20.485 | 29.016 | 34 | GLY | O | 14.875 | 20.030 | 25.242 |
| 24 | SER | O | 35.830 | 21.218 | 29.880 | 35 | ILE | N | 15.492 | 17.921 | 24.630 |
| 25 | GLY | N | 34.786 | 19.290 | 29.245 | 35 | ILE | CA | 16.417 | 18.299 | 23.557 |
| 25 | GLY | CA | 34.688 | 18.702 | 30.571 | 35 | ILE | CB | 17.881 | 18.366 | 24.013 |
| 25 | GLY | C | 33.657 | 19.387 | 31.517 | 35 | ILE | CG2 | 18.614 | 19.017 | 22.822 |
| 25 | GLY | O | 33.562 | 19.018 | 32.697 | 35 | ILE | CG1 | 18.149 | 19.249 | 25.273 |
| 26 | VAL | N | 32.861 | 20.356 | 31.079 | 35 | ILE | CD | 19.589 | 19.096 | 25.859 |
| 26 | VAL | CA | 31.862 | 20.949 | 31.956 | 35 | ILE | C | 16.257 | 17.256 | 22.439 |
| 26 | VAL | CB | 31.863 | 22.501 | 31.794 | 35 | ILE | O | 16.348 | 16.042 | 22.687 |
| 26 | VAL | CG1 | 30.812 | 23.111 | 32.729 | 36 | SER | N | 15.873 | 17.729 | 21.243 |
| 26 | VAL | CG2 | 33.281 | 23.055 | 32.071 | 36 | SER | CA | 15.797 | 16.830 | 20.099 |
| 26 | VAL | C | 30.488 | 20.382 | 31.604 | 36 | SER | CB | 14.885 | 17.400 | 19.036 |
| 26 | VAL | O | 30.089 | 20.375 | 30.446 | 36 | SER | OG | 13.589 | 17.293 | 19.580 |

FIG. 1B

| | | | | | | | | | | |
|---|---|---|---|---|---|---|---|---|---|---|
| 36 | SER | C | 17.166 | 16.572 | 19.462 | 44 | ARG | C | 24.399 | 12.088 | 27.123 |
| 36 | SER | O | 18.018 | 17.473 | 19.331 | 44 | ARG | O | 24.863 | 11.030 | 27.534 |
| 37 | THR | N | 17.380 | 15.298 | 19.076 | 45 | GLY | N | 23.168 | 12.489 | 27.392 |
| 37 | THR | CA | 18.541 | 14.930 | 18.274 | 45 | GLY | CA | 22.286 | 11.766 | 28.306 |
| 37 | THR | CB | 18.300 | 13.522 | 17.755 | 45 | GLY | C | 21.220 | 12.697 | 28.867 |
| 37 | THR | OG1 | 18.169 | 12.722 | 18.926 | 45 | GLY | O | 21.009 | 13.824 | 28.377 |
| 37 | THR | CG2 | 19.401 | 13.039 | 16.808 | 46 | GLY | N | 20.524 | 12.208 | 29.871 |
| 37 | THR | C | 18.675 | 15.912 | 17.089 | 46 | GLY | CA | 19.453 | 12.976 | 30.489 |
| 37 | THR | O | 17.670 | 16.153 | 16.374 | 46 | GLY | C | 18.430 | 12.113 | 31.221 |
| 38 | HIS | N | 19.880 | 16.435 | 16.837 | 46 | GLY | O | 18.632 | 10.912 | 31.445 |
| 38 | HIS | CA | 20.021 | 17.474 | 15.806 | 47 | ALA | N | 17.313 | 12.744 | 31.558 |
| 38 | HIS | CB | 19.786 | 18.868 | 16.461 | 47 | ALA | CA | 16.222 | 12.120 | 32.291 |
| 38 | HIS | CG | 19.722 | 20.046 | 15.486 | 47 | ALA | CB | 16.461 | 12.192 | 33.779 |
| 38 | HIS | CD2 | 20.803 | 20.545 | 14.801 | 47 | ALA | C | 14.953 | 12.896 | 31.997 |
| 38 | HIS | ND1 | 18.655 | 20.775 | 15.114 | 47 | ALA | O | 15.007 | 14.081 | 31.604 |
| 38 | HIS | CE1 | 19.051 | 21.670 | 14.239 | 48 | SER | N | 13.817 | 12.215 | 32.075 |
| 38 | HIS | NE2 | 20.348 | 21.530 | 14.048 | 48 | SER | CA | 12.537 | 12.888 | 31.947 |
| 38 | HIS | C | 21.432 | 17.344 | 15.305 | 48 | SER | CB | 11.680 | 12.343 | 30.801 |
| 38 | HIS | O | 22.341 | 17.174 | 16.118 | 48 | SER | OG | 10.390 | 12.945 | 30.842 |
| 39 | PRO | N | 21.740 | 17.555 | 14.025 | 48 | SER | C | 11.760 | 12.680 | 33.243 |
| 39 | PRO | CD | 20.795 | 17.752 | 12.918 | 48 | SER | O | 11.740 | 11.558 | 33.791 |
| 39 | PRO | CA | 23.135 | 17.467 | 13.571 | 49 | PHE | N | 11.224 | 13.808 | 33.696 |
| 39 | PRO | CB | 23.084 | 17.619 | 12.070 | 49 | PHE | CA | 10.358 | 13.821 | 34.885 |
| 39 | PRO | CG | 21.744 | 18.261 | 11.799 | 49 | PHE | CB | 10.967 | 14.782 | 35.924 |
| 39 | PRO | C | 24.112 | 18.457 | 14.195 | 49 | PHE | CG | 12.302 | 14.253 | 36.403 |
| 39 | PRO | O | 25.318 | 18.260 | 14.162 | 49 | PHE | CD1 | 13.454 | 14.844 | 35.923 |
| 40 | ASP | N | 23.645 | 19.520 | 14.832 | 49 | PHE | CD2 | 12.383 | 13.128 | 37.204 |
| 40 | ASP | CA | 24.583 | 20.488 | 15.375 | 49 | PHE | CE1 | 14.676 | 14.300 | 36.225 |
| 40 | ASP | CB | 24.218 | 21.897 | 14.900 | 49 | PHE | CE2 | 13.616 | 12.590 | 37.509 |
| 40 | ASP | CG | 25.453 | 22.801 | 14.740 | 49 | PHE | CZ | 14.760 | 13.176 | 37.008 |
| 40 | ASP | OD1 | 26.526 | 22.264 | 14.551 | 49 | PHE | C | 8.915 | 14.206 | 34.546 |
| 40 | ASP | OD2 | 25.389 | 24.037 | 14.740 | 49 | PHE | O | 8.115 | 14.601 | 35.418 |
| 40 | ASP | C | 24.561 | 20.439 | 16.874 | 50 | VAL | N | 8.571 | 14.104 | 33.248 |
| 40 | ASP | O | 24.918 | 21.450 | 17.480 | 50 | VAL | CA | 7.230 | 14.424 | 32.796 |
| 41 | LEU | N | 24.080 | 19.327 | 17.430 | 50 | VAL | CB | 7.264 | 15.245 | 31.450 |
| 41 | LEU | CA | 24.102 | 19.142 | 18.883 | 50 | VAL | CG1 | 5.869 | 15.427 | 30.821 |
| 41 | LEU | CB | 22.713 | 19.260 | 19.513 | 50 | VAL | CG2 | 7.766 | 16.635 | 31.755 |
| 41 | LEU | CG | 21.938 | 20.541 | 19.465 | 50 | VAL | C | 6.512 | 13.085 | 32.594 |
| 41 | LEU | CD1 | 20.485 | 20.249 | 19.882 | 50 | VAL | O | 6.894 | 12.336 | 31.695 |
| 41 | LEU | CD2 | 22.642 | 21.595 | 20.331 | 51 | PRO | N | 5.443 | 12.724 | 33.315 |
| 41 | LEU | C | 24.635 | 17.780 | 19.265 | 51 | PRO | CD | 4.826 | 13.553 | 34.344 |
| 41 | LEU | O | 24.417 | 16.802 | 18.530 | 51 | PRO | CA | 4.805 | 11.411 | 33.232 |
| 42 | ASN | N | 25.298 | 17.707 | 20.415 | 51 | PRO | CB | 3.632 | 11.476 | 34.218 |
| 42 | ASN | CA | 25.792 | 16.443 | 20.953 | 51 | PRO | CG | 4.118 | 12.525 | 35.235 |
| 42 | ASN | CB | 27.341 | 16.452 | 21.066 | 51 | PRO | C | 4.358 | 10.971 | 31.854 |
| 42 | ASN | CG | 27.960 | 15.195 | 21.667 | 51 | PRO | O | 4.621 | 9.848 | 31.454 |
| 42 | ASN | OD1 | 29.168 | 15.169 | 21.967 | 52 | GLY | N | 3.693 | 11.820 | 31.082 |
| 42 | ASN | ND2 | 27.260 | 14.090 | 21.803 | 52 | GLY | CA | 3.269 | 11.377 | 29.746 |
| 42 | ASN | C | 25.176 | 16.272 | 22.354 | 52 | GLY | C | 4.368 | 11.323 | 28.690 |
| 42 | ASN | O | 25.590 | 16.890 | 22.332 | 52 | GLY | O | 4.117 | 10.848 | 27.575 |
| 43 | ILE | N | 24.152 | 15.442 | 22.457 | 53 | GLU | N | 5.606 | 11.757 | 28.996 |
| 43 | ILE | CA | 23.458 | 15.252 | 23.736 | 53 | GLU | CA | 6.645 | 11.848 | 28.005 |
| 43 | ILE | CB | 21.958 | 15.077 | 23.423 | 53 | GLU | CB | 6.909 | 13.311 | 27.676 |
| 43 | ILE | CG2 | 21.208 | 14.865 | 24.766 | 53 | GLU | CG | 5.740 | 13.985 | 27.008 |
| 43 | ILE | CG1 | 21.451 | 16.284 | 22.605 | 53 | GLU | CD | 5.991 | 15.433 | 26.597 |
| 43 | ILE | CD | 20.150 | 16.044 | 21.857 | 53 | GLU | OE1 | 7.145 | 15.826 | 26.393 |
| 43 | ILE | C | 24.075 | 14.023 | 24.422 | 53 | GLU | OE2 | 5.012 | 16.167 | 26.462 |
| 43 | ILE | O | 24.160 | 12.963 | 23.781 | 53 | GLU | C | 7.901 | 11.202 | 28.519 |
| 44 | ARG | N | 24.520 | 14.131 | 25.675 | 53 | GLU | O | 8.803 | 11.919 | 28.919 |
| 44 | ARG | CA | 25.246 | 13.030 | 26.309 | 54 | PRO | N | 8.059 | 9.880 | 28.483 |
| 44 | ARG | CB | 26.332 | 13.557 | 27.250 | 54 | PRO | CD | 7.103 | 8.945 | 27.908 |
| 44 | ARG | CG | 27.060 | 14.753 | 26.730 | 54 | PRO | CA | 9.245 | 9.200 | 29.004 |
| 44 | ARG | CD | 27.731 | 14.330 | 25.467 | 54 | PRO | CB | 8.817 | 7.745 | 28.993 |
| 44 | ARG | NE | 29.007 | 13.812 | 25.844 | 54 | PRO | CG | 7.964 | 7.702 | 27.752 |
| 44 | ARG | CZ | 30.106 | 14.554 | 25.653 | 54 | PRO | C | 10.548 | 9.487 | 28.240 |
| 44 | ARG | NH1 | 31.274 | 14.034 | 26.023 | 54 | PRO | O | 11.625 | 9.172 | 28.750 |
| 44 | ARG | NH2 | 30.099 | 15.758 | 25.065 | 55 | SER | N | 10.497 | 10.048 | 27.015 |

FIG. 1C

```
55 SER  CA   11.678 10.360 26.197    65 HIS  CA   16.749 26.168 20.989
55 SER  CB   11.310 10.444 24.730    65 HIS  CB   15.534 27.012 20.769
55 SER  OG   12.390 10.759 23.870    65 HIS  CG   15.850 28.409 28.237
55 SER  C    12.250 11.702 26.559    65 HIS  CD2  15.686 28.794 18.918
55 SER  O    11.469 12.540 27.001    65 HIS  ND1  16.319 29.457 20.941
56 THR  N    13.533 11.968 26.265    65 HIS  CE1  16.438 30.455 20.096
56 THR  CA   14.084 13.315 26.487    65 HIS  NE2  16.056 30.048 18.887
56 THR  CB   15.596 13.250 26.945    65 HIS  C    17.672 26.657 22.118
56 THR  OG1  16.283 12.433 25.998    65 HIS  O    18.820 27.073 21.904
56 THR  CG2  15.743 12.741 28.390    66 VAL  N    17.220 26.535 23.376
56 THR  C    13.978 14.192 25.225    66 VAL  CA   18.084 26.803 24.544
56 THR  O    14.370 15.358 25.250    66 VAL  CB   17.351 26.378 25.832
57 GLN  N    13.331 13.623 24.170    66 VAL  CG1  18.194 26.482 27.092
57 GLN  CA   13.252 14.317 22.886    66 VAL  CG2  16.264 27.335 25.994
57 GLN  CB   12.743 13.375 21.797    66 VAL  C    19.427 26.062 24.466
57 GLN  CG   13.825 12.370 21.360    66 VAL  O    20.494 26.687 24.586
57 GLN  CD   15.108 13.013 20.762    67 ALA  N    19.347 24.730 24.292
57 GLN  OE1  15.091 13.752 19.766    67 ALA  CA   20.534 23.878 24.204
57 GLN  NE2  16.267 12.793 21.390    67 ALA  CB   20.081 22.462 23.828
57 GLN  C    12.314 15.495 23.027    67 ALA  C    21.526 24.393 23.140
57 GLN  O    11.395 15.425 23.858    67 ALA  O    22.732 24.464 23.385
58 ASP  N    12.508 16.545 22.256    68 GLY  N    21.028 24.843 21.978
58 ASP  CA   11.724 17.738 22.451    68 GLY  CA   21.890 25.373 20.923
58 ASP  CB   12.619 18.910 22.214    68 GLY  C    22.602 26.682 21.221
58 ASP  CG   12.036 20.302 22.427    68 GLY  O    23.730 26.888 20.726
58 ASP  OD1  10.950 20.447 23.006    69 THR  N    22.009 27.580 22.020
58 ASP  OD2  12.737 21.245 22.032    69 THR  CA   22.727 28.785 22.414
58 ASP  C    10.499 17.854 21.573    69 THR  CB   21.703 29.733 23.084
58 ASP  O    10.627 18.076 20.358    69 THR  OG1  20.690 29.972 22.076
59 GLY  N     9.311 17.809 22.191    69 THR  CG2  22.339 31.046 23.576
59 GLY  CA    8.021 17.992 21.500    69 THR  C    23.902 28.431 23.353
59 GLY  C     7.601 19.445 21.318    69 THR  O    24.986 29.042 23.288
59 GLY  O     6.527 19.731 20.754    70 ILE  N    23.686 27.426 24.235
60 ASN  N     8.431 20.374 21.802    70 ILE  CA   24.771 26.952 25.107
60 ASN  CA    8.085 21.787 21.793    70 ILE  CB   24.305 25.947 26.219
60 ASN  CB    8.166 22.340 23.222    70 ILE  CG2  25.501 25.525 27.092
60 ASN  CG    7.768 23.804 23.268    70 ILE  CG1  23.197 26.607 27.065
60 ASN  OD1   8.585 24.702 23.090    70 ILE  CD   22.458 25.687 28.103
60 ASN  ND2   6.503 24.085 23.545    70 ILE  C    25.820 26.222 24.285
60 ASN  C     8.971 22.642 20.883    70 ILE  O    27.014 26.530 24.398
60 ASN  O     8.525 23.378 20.022    71 ALA  N    25.447 25.251 23.451
61 GLY  N    10.269 22.585 21.093    71 ALA  CA   26.467 24.349 22.986
61 GLY  CA   11.202 23.372 20.337    71 ALA  CB   26.523 23.129 23.948
61 GLY  C    12.035 24.187 21.318    71 ALA  C    26.352 23.895 21.578
61 GLY  O    13.231 24.429 21.115    71 ALA  O    26.869 22.805 21.295
62 HIS  N    11.417 24.583 22.439    72 ALA  N    25.785 24.709 20.671
62 HIS  CA   12.068 25.515 23.336    72 ALA  CA   25.772 24.252 19.280
62 HIS  CB   11.034 25.886 24.385    72 ALA  CB   25.105 25.252 18.367
62 HIS  CG   11.450 27.020 25.268    72 ALA  C    27.223 24.056 18.832
62 HIS  CD2  11.218 28.363 25.048    72 ALA  O    28.112 24.803 19.205
62 HIS  ND1  11.969 26.858 26.498    73 LEU  N    27.412 22.934 18.090
62 HIS  CE1  12.011 28.039 27.067    73 LEU  CA   28.744 22.458 17.726
62 HIS  NE2  11.572 28.932 26.189    73 LEU  CB   28.630 21.030 17.087
62 HIS  C    13.371 24.957 23.944    73 LEU  CG   27.913 19.969 17.918
62 HIS  O    14.409 25.642 23.918    73 LEU  CD1  27.805 18.638 17.193
63 GLY  N    13.351 23.723 24.453    73 LEU  CD2  28.650 19.898 19.221
63 GLY  CA   14.577 23.186 25.039    73 LEU  C    29.465 23.384 16.782
63 GLY  C    15.709 23.028 24.021    73 LEU  O    28.857 23.968 15.858
63 GLY  O    16.870 23.232 24.356    74 ASN  N    30.768 23.410 17.002
64 THR  N    15.375 22.712 22.746    74 ASN  CA   31.650 24.268 16.196
64 THR  CA   16.392 22.485 21.700    74 ASN  CB   32.829 24.736 17.002
64 THR  CB   15.729 21.894 20.395    74 ASN  CG   33.638 25.786 16.240
64 THR  OG1  15.057 20.682 20.709    74 ASN  OD1  33.278 26.358 15.207
64 THR  CG2  16.823 21.570 19.338    74 ASN  ND2  34.798 26.098 16.774
64 THR  C    17.078 23.790 21.373    74 ASN  C    32.170 23.435 15.022
64 THR  O    18.287 23.840 21.192    74 ASN  O    33.097 22.639 15.197
65 HIS  N    16.252 24.838 21.308    75 ASN  N    31.602 23.663 13.836
```

FIG. 1D

| | | | | | | | | | | |
|---|---|---|---|---|---|---|---|---|---|---|
| 75 | ASN | CA | 31.833 | 22.805 | 12.665 | 85 | SER | C | 31.718 | 21.142 | 25.147 |
| 75 | ASN | CB | 30.957 | 21.533 | 12.702 | 85 | SER | O | 32.117 | 20.128 | 25.689 |
| 75 | ASN | CG | 29.491 | 21.798 | 13.007 | 86 | ALA | N | 30.806 | 21.904 | 25.738 |
| 75 | ASN | OD1 | 28.914 | 22.891 | 12.815 | 86 | ALA | CA | 30.151 | 21.459 | 26.967 |
| 75 | ASN | ND2 | 28.869 | 20.780 | 13.605 | 86 | ALA | CB | 29.153 | 22.489 | 27.391 |
| 75 | ASN | C | 31.502 | 23.581 | 11.415 | 86 | ALA | C | 29.408 | 20.122 | 26.787 |
| 75 | ASN | O | 31.582 | 24.793 | 11.490 | 86 | ALA | O | 28.914 | 19.771 | 25.689 |
| 76 | SER | N | 31.121 | 22.947 | 10.298 | 87 | GLU | N | 29.338 | 19.367 | 27.882 |
| 76 | SER | CA | 30.794 | 23.635 | 9.055 | 87 | GLU | CA | 28.637 | 18.102 | 27.917 |
| 76 | SER | CB | 31.452 | 22.852 | 7.920 | 87 | GLU | CB | 29.274 | 17.235 | 28.985 |
| 76 | SER | OG | 32.867 | 22.956 | 8.023 | 87 | GLU | CG | 30.727 | 16.977 | 28.652 |
| 76 | SER | C | 29.308 | 23.826 | 8.771 | 87 | GLU | CD | 31.359 | 15.911 | 29.523 |
| 76 | SER | O | 28.913 | 24.172 | 7.628 | 87 | GLU | OE1 | 30.638 | 15.142 | 30.165 |
| 77 | ILE | N | 28.486 | 23.612 | 9.815 | 87 | GLU | OE2 | 32.580 | 15.850 | 29.550 |
| 77 | ILE | CA | 27.049 | 23.710 | 9.658 | 87 | GLU | C | 27.172 | 18.407 | 28.237 |
| 77 | ILE | CB | 26.315 | 22.283 | 9.597 | 87 | GLU | O | 26.787 | 18.788 | 29.353 |
| 77 | ILE | CG2 | 26.735 | 21.594 | 8.269 | 88 | LEU | N | 26.340 | 18.241 | 27.230 |
| 77 | ILE | CG1 | 26.604 | 21.393 | 10.803 | 88 | LEU | CA | 24.949 | 18.654 | 27.326 |
| 77 | ILE | CD | 25.657 | 20.178 | 10.887 | 88 | LEU | CB | 24.566 | 19.080 | 25.910 |
| 77 | ILE | C | 26.407 | 24.494 | 10.799 | 88 | LEU | CG | 23.561 | 20.137 | 25.626 |
| 77 | ILE | O | 26.960 | 24.700 | 11.891 | 88 | LEU | CD1 | 23.929 | 21.475 | 26.321 |
| 78 | GLY | N | 25.199 | 24.925 | 10.501 | 88 | LEU | CD2 | 23.521 | 20.293 | 24.093 |
| 78 | GLY | CA | 24.338 | 25.534 | 11.486 | 88 | LEU | C | 24.042 | 17.570 | 27.876 |
| 78 | GLY | C | 24.874 | 26.773 | 12.159 | 88 | LEU | O | 24.093 | 16.491 | 27.282 |
| 78 | GLY | O | 25.345 | 27.713 | 11.542 | 89 | TYR | N | 23.223 | 17.777 | 28.919 |
| 79 | VAL | N | 24.781 | 26.721 | 13.475 | 89 | TYR | CA | 22.249 | 16.807 | 29.449 |
| 79 | VAL | CA | 25.226 | 27.840 | 14.293 | 89 | TYR | CB | 22.538 | 16.474 | 30.942 |
| 79 | VAL | CB | 23.977 | 28.470 | 15.058 | 89 | TYR | CG | 23.828 | 15.673 | 31.047 |
| 79 | VAL | CG1 | 23.105 | 29.130 | 14.034 | 89 | TYR | CD1 | 25.048 | 16.317 | 30.920 |
| 79 | VAL | CG2 | 23.172 | 27.468 | 15.841 | 89 | TYR | CE1 | 26.230 | 15.627 | 30.860 |
| 79 | VAL | C | 26.342 | 27.460 | 15.258 | 89 | TYR | CD2 | 23.797 | 14.292 | 31.142 |
| 79 | VAL | O | 27.035 | 26.445 | 15.015 | 89 | TYR | CE2 | 24.979 | 13.578 | 31.070 |
| 80 | LEU | N | 26.574 | 28.266 | 16.310 | 89 | TYR | CZ | 26.175 | 14.250 | 30.937 |
| 80 | LEU | CA | 27.681 | 28.023 | 17.216 | 89 | TYR | OH | 27.340 | 13.513 | 30.872 |
| 80 | LEU | CB | 28.856 | 28.882 | 16.777 | 89 | TYR | C | 20.847 | 17.347 | 29.318 |
| 80 | LEU | CG | 30.090 | 28.886 | 17.612 | 89 | TYR | O | 20.561 | 18.513 | 29.646 |
| 80 | LEU | CD1 | 30.630 | 27.510 | 17.592 | 90 | ALA | N | 20.000 | 16.511 | 28.733 |
| 80 | LEU | CD2 | 31.076 | 29.900 | 17.113 | 90 | ALA | CA | 18.613 | 16.880 | 28.538 |
| 80 | LEU | C | 27.210 | 28.436 | 18.614 | 90 | ALA | CB | 17.991 | 16.206 | 27.306 |
| 80 | LEU | O | 26.667 | 29.536 | 18.725 | 90 | ALA | C | 17.794 | 16.453 | 29.749 |
| 81 | GLY | N | 27.333 | 27.597 | 19.625 | 90 | ALA | O | 17.565 | 15.260 | 29.984 |
| 81 | GLY | CA | 26.928 | 28.085 | 20.924 | 91 | VAL | N | 17.307 | 17.405 | 30.542 |
| 81 | GLY | C | 28.076 | 28.805 | 21.662 | 91 | VAL | CA | 16.489 | 17.070 | 31.706 |
| 81 | GLY | O | 29.253 | 28.863 | 21.248 | 91 | VAL | CB | 17.050 | 17.737 | 32.979 |
| 82 | VAL | N | 27.794 | 29.222 | 22.883 | 91 | VAL | CG1 | 16.278 | 17.172 | 34.186 |
| 82 | VAL | CA | 28.824 | 29.876 | 23.663 | 91 | VAL | CG2 | 18.529 | 17.434 | 33.152 |
| 82 | VAL | CB | 28.207 | 30.550 | 24.929 | 91 | VAL | C | 15.086 | 17.576 | 31.413 |
| 82 | VAL | CG1 | 29.266 | 31.108 | 25.913 | 91 | VAL | O | 14.803 | 18.789 | 31.545 |
| 82 | VAL | CG2 | 27.250 | 31.691 | 24.395 | 92 | LYS | N | 14.186 | 16.716 | 30.935 |
| 82 | VAL | C | 29.915 | 28.926 | 24.085 | 92 | LYS | CA | 12.860 | 17.211 | 30.608 |
| 82 | VAL | O | 31.102 | 29.295 | 24.118 | 92 | LYS | CB | 12.271 | 16.257 | 29.604 |
| 83 | ALA | N | 29.504 | 27.716 | 24.494 | 92 | LYS | CG | 10.802 | 16.621 | 29.273 |
| 83 | ALA | CA | 30.437 | 26.706 | 24.970 | 92 | LYS | CD | 10.070 | 15.579 | 28.398 |
| 83 | ALA | CB | 30.194 | 26.444 | 26.456 | 92 | LYS | CE | 10.580 | 15.652 | 26.970 |
| 83 | ALA | C | 30.270 | 25.404 | 24.181 | 92 | LYS | NZ | 9.873 | 14.730 | 26.095 |
| 83 | ALA | O | 29.605 | 24.459 | 24.615 | 92 | LYS | C | 12.009 | 17.347 | 31.892 |
| 84 | PRO | N | 30.827 | 25.356 | 22.956 | 92 | LYS | O | 11.719 | 16.396 | 32.624 |
| 84 | PRO | CD | 31.627 | 26.423 | 22.334 | 93 | VAL | N | 11.659 | 18.596 | 32.162 |
| 84 | PRO | CA | 30.449 | 24.325 | 21.985 | 93 | VAL | CA | 10.834 | 18.966 | 33.299 |
| 84 | PRO | CB | 30.988 | 24.826 | 20.658 | 93 | VAL | CB | 11.520 | 19.956 | 34.315 |
| 84 | PRO | CG | 31.954 | 25.925 | 20.928 | 93 | VAL | CG1 | 12.719 | 19.267 | 34.948 |
| 84 | PRO | C | 30.900 | 22.929 | 22.328 | 93 | VAL | CG2 | 11.808 | 21.301 | 33.634 |
| 84 | PRO | O | 30.460 | 21.987 | 21.673 | 93 | VAL | C | 9.545 | 19.632 | 32.844 |
| 85 | SER | N | 31.795 | 22.800 | 23.311 | 93 | VAL | O | 8.636 | 19.907 | 33.627 |
| 85 | SER | CA | 32.303 | 21.525 | 23.810 | 94 | LEU | N | 9.434 | 19.988 | 31.564 |
| 85 | SER | CB | 33.826 | 21.574 | 23.944 | 94 | LEU | CA | 8.253 | 20.628 | 31.023 |
| 85 | SER | OG | 34.358 | 21.691 | 22.630 | 94 | LEU | CB | 8.576 | 22.025 | 30.524 |

FIG. 1E

| | | | | | | | | | | |
|---|---|---|---|---|---|---|---|---|---|---|
| 94 | LEU | CG | 9.291 | 22.983 | 31.432 | 105 | ILE | CA | 11.308 | 20.992 | 38.055 |
| 94 | LEU | CD1 | 9.772 | 24.188 | 30.604 | 105 | ILE | CB | 10.782 | 22.425 | 38.033 |
| 94 | LEU | CD2 | 8.380 | 23.374 | 32.555 | 105 | ILE | CG2 | 12.002 | 23.365 | 38.118 |
| 94 | LEU | C | 7.783 | 19.781 | 29.830 | 105 | ILE | CG1 | 9.919 | 22.652 | 36.794 |
| 94 | LEU | O | 8.605 | 19.154 | 29.150 | 105 | ILE | CD | 9.191 | 24.036 | 36.796 |
| 95 | GLY | N | 6.479 | 19.754 | 29.581 | 105 | ILE | C | 12.186 | 20.703 | 39.293 |
| 95 | GLY | CA | 5.913 | 18.985 | 28.494 | 105 | ILE | O | 13.406 | 20.539 | 39.166 |
| 95 | GLY | C | 5.987 | 19.713 | 27.150 | 106 | ALA | N | 11.585 | 20.494 | 40.484 |
| 95 | GLY | O | 6.394 | 20.881 | 27.052 | 106 | ALA | CA | 12.324 | 20.165 | 41.677 |
| 96 | ALA | N | 5.518 | 18.995 | 26.112 | 106 | ALA | CB | 11.347 | 20.164 | 42.870 |
| 96 | ALA | CA | 5.460 | 19.485 | 24.733 | 106 | ALA | C | 13.009 | 18.797 | 41.505 |
| 96 | ALA | CB | 4.826 | 18.408 | 23.824 | 106 | ALA | O | 14.185 | 18.706 | 41.872 |
| 96 | ALA | C | 4.659 | 20.791 | 24.611 | 107 | GLN | N | 12.452 | 17.715 | 40.904 |
| 96 | ALA | O | 4.945 | 21.657 | 23.772 | 107 | GLN | CA | 13.267 | 16.487 | 40.797 |
| 97 | ASP | N | 3.680 | 20.986 | 25.508 | 107 | GLN | CB | 12.484 | 15.170 | 40.501 |
| 97 | ASP | CA | 2.957 | 22.248 | 25.636 | 107 | GLN | CG | 11.380 | 14.761 | 41.453 |
| 97 | ASP | CB | 1.637 | 22.010 | 26.330 | 107 | GLN | CD | 10.582 | 13.516 | 41.085 |
| 97 | ASP | CG | 1.665 | 21.267 | 27.665 | 107 | GLN | OE1 | 9.435 | 13.412 | 41.526 |
| 97 | ASP | OD1 | 2.704 | 20.782 | 28.130 | 107 | GLN | NE2 | 11.040 | 12.542 | 40.292 |
| 97 | ASP | OD2 | 0.596 | 21.183 | 28.270 | 107 | GLN | C | 14.299 | 16.625 | 39.702 |
| 97 | ASP | C | 3.645 | 23.410 | 26.351 | 107 | GLN | O | 15.333 | 15.973 | 39.804 |
| 97 | ASP | O | 3.058 | 24.477 | 26.509 | 108 | GLY | N | 14.058 | 17.494 | 38.722 |
| 98 | GLY | N | 4.885 | 23.232 | 26.820 | 108 | GLY | CA | 15.068 | 17.832 | 37.732 |
| 98 | GLY | CA | 5.597 | 24.264 | 27.561 | 108 | GLY | C | 16.281 | 18.376 | 38.456 |
| 98 | GLY | C | 5.223 | 24.311 | 29.038 | 108 | GLY | O | 17.409 | 17.922 | 38.169 |
| 98 | GLY | O | 5.866 | 24.997 | 29.828 | 109 | LEU | N | 16.086 | 19.337 | 39.380 |
| 99 | ARG | N | 4.228 | 23.548 | 29.442 | 109 | LEU | CA | 17.203 | 19.921 | 40.151 |
| 99 | ARG | CA | 3.746 | 23.492 | 30.813 | 109 | LEU | CB | 16.703 | 21.098 | 40.941 |
| 99 | ARG | CB | 2.274 | 23.049 | 30.885 | 109 | LEU | CG | 16.358 | 22.306 | 40.103 |
| 99 | ARG | CG | 1.275 | 23.728 | 29.965 | 109 | LEU | CD1 | 15.553 | 23.267 | 40.958 |
| 99 | ARG | CD | 1.373 | 25.198 | 30.169 | 109 | LEU | CD2 | 17.613 | 22.976 | 39.579 |
| 99 | ARG | NE | 0.065 | 25.771 | 29.978 | 109 | LEU | C | 17.899 | 18.952 | 41.088 |
| 99 | ARG | CZ | -0.085 | 27.070 | 29.703 | 109 | LEU | O | 19.137 | 18.923 | 41.163 |
| 99 | ARG | NH1 | -1.339 | 27.516 | 29.555 | 110 | GLU | N | 17.146 | 18.078 | 41.739 |
| 99 | ARG | NH2 | 0.956 | 27.923 | 29.560 | 110 | GLU | CA | 17.767 | 16.997 | 42.502 |
| 99 | ARG | C | 4.518 | 22.498 | 31.672 | 110 | GLU | CB | 16.706 | 16.208 | 43.295 |
| 99 | ARG | O | 4.851 | 21.418 | 31.175 | 110 | GLU | CG | 16.044 | 17.043 | 44.443 |
| 100 | GLY | N | 4.746 | 22.767 | 32.962 | 110 | GLU | CD | 16.869 | 17.518 | 45.693 |
| 100 | GLY | CA | 5.370 | 21.790 | 33.846 | 110 | GLU | OE1 | 16.284 | 18.250 | 46.507 |
| 100 | GLY | C | 5.043 | 22.002 | 35.327 | 110 | GLU | OE2 | 18.058 | 17.205 | 45.884 |
| 100 | GLY | O | 4.933 | 23.136 | 35.803 | 110 | GLU | C | 18.562 | 16.049 | 41.616 |
| 101 | ALA | N | 4.881 | 20.881 | 36.029 | 110 | GLU | O | 19.674 | 15.702 | 42.025 |
| 101 | ALA | CA | 4.592 | 20.897 | 37.462 | 111 | TRP | N | 18.111 | 15.691 | 40.389 |
| 101 | ALA | CB | 4.090 | 19.544 | 37.966 | 111 | TRP | CA | 18.867 | 14.850 | 39.469 |
| 101 | ALA | C | 5.844 | 21.210 | 38.278 | 111 | TRP | CB | 18.049 | 14.586 | 38.169 |
| 101 | ALA | O | 6.945 | 20.745 | 37.930 | 111 | TRP | CG | 18.743 | 13.709 | 37.091 |
| 102 | ILE | N | 5.672 | 21.920 | 39.412 | 111 | TRP | CD2 | 19.617 | 14.121 | 36.111 |
| 102 | ILE | CA | 6.812 | 22.262 | 40.268 | 111 | TRP | CE2 | 19.919 | 12.914 | 35.467 |
| 102 | ILE | CB | 6.297 | 23.134 | 41.461 | 111 | TRP | CE3 | 20.195 | 15.302 | 35.658 |
| 102 | ILE | CG2 | 7.414 | 23.536 | 42.429 | 111 | TRP | CD1 | 18.535 | 12.343 | 37.029 |
| 102 | ILE | CG1 | 5.672 | 24.383 | 40.856 | 111 | TRP | NE1 | 19.264 | 11.895 | 36.042 |
| 102 | ILE | CD | 6.675 | 25.257 | 40.045 | 111 | TRP | CZ2 | 20.803 | 12.903 | 34.389 |
| 102 | ILE | C | 7.555 | 21.016 | 40.763 | 111 | TRP | CZ3 | 21.073 | 15.292 | 34.585 |
| 102 | ILE | O | 8.790 | 21.014 | 40.848 | 111 | TRP | CH2 | 21.370 | 14.099 | 33.959 |
| 103 | SER | N | 6.839 | 19.922 | 41.067 | 111 | TRP | C | 20.160 | 15.563 | 39.124 |
| 103 | SER | CA | 7.477 | 18.691 | 41.459 | 111 | TRP | O | 21.198 | 14.910 | 39.072 |
| 103 | SER | CB | 6.399 | 17.659 | 41.711 | 112 | ALA | N | 20.134 | 16.881 | 38.876 |
| 103 | SER | OG | 5.570 | 17.479 | 40.562 | 112 | ALA | CA | 21.331 | 17.620 | 38.528 |
| 103 | SER | C | 8.451 | 18.211 | 40.361 | 112 | ALA | CB | 21.029 | 19.102 | 38.310 |
| 103 | SER | O | 9.575 | 17.820 | 40.676 | 112 | ALA | C | 22.411 | 17.530 | 39.612 |
| 104 | SER | N | 8.068 | 18.299 | 39.085 | 112 | ALA | O | 23.578 | 17.183 | 39.356 |
| 104 | SER | CA | 8.950 | 17.948 | 37.972 | 113 | GLY | N | 22.019 | 17.742 | 40.859 |
| 104 | SER | CB | 8.185 | 18.077 | 36.660 | 113 | GLY | CA | 22.962 | 17.686 | 41.947 |
| 104 | SER | OG | 7.214 | 17.048 | 36.535 | 113 | GLY | C | 23.404 | 16.258 | 42.205 |
| 104 | SER | C | 10.230 | 18.802 | 37.897 | 113 | GLY | O | 24.567 | 16.052 | 42.565 |
| 104 | SER | O | 11.330 | 18.272 | 37.756 | 114 | ASN | N | 22.524 | 15.285 | 42.009 |
| 105 | ILE | N | 10.136 | 20.124 | 38.041 | 114 | ASN | CA | 22.901 | 13.872 | 42.191 |

FIG. 1F

```
114  ASN   CB  21.735  12.858  42.176     123  SER   OG  16.514  29.408  29.479
114  ASN   CG  20.764  12.994  43.318     123  SER    C  13.240  29.029  31.383
114  ASN  OD1  21.095  13.531  44.373     123  SER    O  12.521  28.751  30.400
114  ASN  ND2  19.511  12.575  43.163     124  LEU    N  12.818  29.236  32.647
114  ASN    C  23.820  13.339  41.111     124  LEU   CA  11.426  29.119  33.059
114  ASN    O  24.532  12.346  41.311     124  LEU   CB  11.093  27.646  33.233
115  ASN    N  23.767  13.953  39.923     124  LEU   CG  12.008  26.810  34.115
115  ASN   CA  24.558  13.494  38.817     124  LEU  CD1  11.540  26.904  35.610
115  ASN   CB  23.678  13.382  37.576     124  LEU  CD2  11.993  25.356  33.606
115  ASN   CG  22.871  12.090  37.637     124  LEU    C  11.200  29.897  34.347
115  ASN  OD1  23.296  11.044  37.144     124  LEU    O  12.165  30.261  35.045
115  ASN  ND2  21.716  12.088  38.291     125  GLY    N   9.951  30.177  34.709
115  ASN    C  25.761  14.354  38.510     125  GLY   CA   9.733  31.019  35.884
115  ASN    O  26.352  14.277  37.428     125  GLY    C   8.243  31.204  36.140
116  GLY    N  26.126  15.225  39.431     125  GLY    O   7.396  31.003  35.252
116  GLY   CA  27.354  15.971  39.331     126  SER    N   7.991  31.643  37.370
116  GLY    C  27.372  16.991  38.204     126  SER   CA   6.640  31.772  37.888
116  GLY    O  28.450  17.247  37.614     126  SER   CB   6.331  30.503  38.752
117  MET    N  26.235  17.614  37.909     126  SER   OG   5.242  30.673  39.682
117  MET   CA  26.210  18.667  36.878     126  SER    C   6.623  33.055  38.707
117  MET   CB  24.807  19.105  36.509     126  SER    O   7.650  33.353  39.302
117  MET   CG  23.929  18.029  35.895     127  PRO    N   5.544  33.844  38.839
117  MET   SD  24.529  17.426  34.290     127  PRO   CD   4.300  33.663  38.088
117  MET   CE  24.874  15.741  34.705     127  PRO   CA   5.458  35.005  39.740
117  MET    C  26.888  19.893  37.466     127  PRO   CB   4.310  35.813  39.157
117  MET    O  26.805  20.170  38.688     127  PRO   CG   3.377  34.706  38.715
118  HIS    N  27.549  20.672  36.615     127  PRO    C   5.258  34.663  41.234
118  HIS   CA  28.186  21.879  37.094     127  PRO    O   5.342  35.518  42.119
118  HIS   CB  29.481  22.174  36.318     128  SER    N   4.904  33.408  41.511
118  HIS   CG  30.504  21.026  36.418     128  SER   CA   4.673  32.939  42.860
118  HIS  CD2  30.795  20.176  35.397     128  SER   CB   3.340  32.142  42.821
118  HIS  ND1  31.283  20.653  37.437     128  SER   OG   2.292  33.013  42.389
118  HIS  CE1  32.020  19.622  37.044     128  SER    C   5.845  32.100  43.399
118  HIS  NE2  31.715  19.339  35.797     128  SER    O   6.430  31.293  42.646
118  HIS    C  27.256  23.067  36.967     129  PRO    N   6.223  32.275  44.678
118  HIS    O  27.293  23.989  37.781     129  PRO   CD   5.713  33.322  45.595
119  VAL    N  26.349  23.070  35.989     129  PRO   CA   7.185  31.419  45.363
119  VAL   CA  25.540  24.246  35.723     129  PRO   CB   7.492  32.187  46.641
119  VAL   CB  26.124  25.082  34.533     129  PRO   CG   6.138  32.757  46.937
199  VAL  CG1  25.194  26.267  34.244     129  PRO    C   6.639  29.999  45.605
119  VAL  CG2  27.537  25.612  34.864     129  PRO    O   5.416  29.779  45.693
119  VAL    C  24.194  23.670  35.344     130  SER    N   7.567  29.069  45.789
119  VAL    O  24.123  22.627  34.674     130  SER   CA   7.242  27.724  46.139
120  ALA    N  23.150  24.305  35.817     130  SER   CB   7.197  26.894  44.888
120  ALA   CA  21.801  23.917  35.457     130  SER   OG   7.387  25.528  45.215
120  ALA   CB  21.074  23.434  36.689     130  SER    C   8.260  27.146  47.092
120  ALA    C  21.128  25.170  34.893     130  SER    O   9.462  27.127  46.751
120  ALA    O  21.156  26.255  35.503     131  ALA    N   7.759  26.596  48.220
121  ASN    N  20.621  25.061  33.673     131  ALA   CA   8.619  25.896  49.154
121  ASN   CA  19.917  26.133  32.994     131  ALA   CB   7.818  25.334  50.312
121  ASN   CB  20.330  26.144  31.516     131  ALA    C   9.445  24.755  48.557
121  ASN   CG  19.771  27.348  30.778     131  ALA    O  10.670  24.654  48.755
121  ASN  OD1  20.464  28.304  30.514     132  THR    N   8.761  23.973  47.716
121  ASN  ND2  18.511  27.315  30.418     132  THR   CA   9.373  22.810  47.044
121  ASN    C  18.399  25.942  33.133     132  THR   CB   8.274  22.155  46.232
121  ASN    O  17.793  24.936  32.715     132  THR  OG1   7.351  21.804  47.256
122  LEU    N  17.740  26.917  33.768     132  THR  CG2   8.667  20.937  45.371
122  LEU   CA  16.277  26.942  33.962     132  THR    C  10.547  23.223  46.156
122  LEU   CB  15.895  27.041  35.454     132  THR    O  11.674  22.711  46.213
122  LEU   CG  16.010  25.856  36.340     133  LEU    N  10.257  24.266  45.394
122  LEU  CD1  15.879  26.350  37.770     133  LEU   CA  11.185  24.742  44.396
122  LEU  CD2  14.914  24.875  36.068     133  LEU   CB  10.467  25.753  43.511
122  LEU    C  15.706  28.182  33.264     133  LEU   CG  11.231  26.287  42.326
122  LEU    O  15.618  29.298  33.808     133  LEU  CD1  11.504  25.174  41.324
123  SER    N  15.297  28.013  32.012     133  LEU  CD2  10.395  27.377  41.663
123  SER   CA  14.756  29.116  31.232     133  LEU    C  12.393  25.365  45.081
123  SER   CB  15.184  28.969  29.748     133  LEU    O  13.539  25.053  44.693
```

FIG. 1G

| | | | | | | | | | | |
|---|---|---|---|---|---|---|---|---|---|---|
|134|GLU|N|12.164|26.195|46.111|143|ARG|NE|22.030|17.901|45.589|
|134|GLU|CA|13.276|26.827|46.768|143|ARG|CZ|21.037|17.422|44.816|
|134|GLU|CB|12.749|27.786|47.793|143|ARG|NH1|20.140|18.281|44.355|
|134|GLU|CG|13.795|28.476|48.645|143|ARG|NH2|20.887|16.134|44.524|
|134|GLU|CD|13.249|29.330|49.814|143|ARG|C|26.745|20.456|44.602|
|134|GLU|OE1|14.013|30.014|50.482|143|ARG|O|27.216|19.708|43.740|
|134|GLU|OE2|12.046|29.337|50.036|144|GLY|N|27.007|21.760|44.635|
|134|GLU|C|14.181|25.795|47.420|144|GLY|CA|27.925|22.456|43.737|
|134|GLU|O|15.396|25.915|47.353|144|GLY|C|27.365|22.887|42.396|
|135|GLN|N|13.598|24.770|48.060|144|GLY|O|28.139|23.324|41.539|
|135|GLN|CA|14.373|23.701|48.651|145|VAL|N|26.048|22.782|42.186|
|135|GLN|CB|13.350|22.830|49.331|145|VAL|CA|25.465|22.150|40.874|
|135|GLN|CG|13.897|21.596|59.006|145|VAL|CB|24.118|22.435|40.672|
|135|GLN|CD|12.823|20.790|50.764|145|VAL|CG1|23.521|22.778|39.291|
|135|GLN|OE1|11.779|20.305|50.258|145|VAL|CG2|24.324|20.921|40.792|
|135|GLN|NE2|13.143|20.692|52.060|145|VAL|C|25.262|24.680|40.827|
|135|GLN|C|15.248|22.952|47.620|145|VAL|O|24.836|25.282|41.840|
|135|GLN|O|16.434|22.651|47.868|146|LEU|N|25.677|25.350|39.742|
|136|ALA|N|14.690|22.749|46.420|146|LEU|CA|25.317|26.759|39.578|
|136|ALA|CA|15.406|22.071|45.337|146|LEU|CB|26.351|27.518|38.740|
|136|ALA|CB|14.430|21.762|44.225|146|LEU|CG|26.005|28.987|38.374|
|136|ALA|C|16.556|22.950|44.802|146|LEU|CD1|25.819|29.816|39.604|
|136|ALA|O|17.676|22.465|44.513|146|LEU|CD2|27.114|29.556|37.506|
|137|VAL|N|16.313|24.272|44.677|146|LEU|C|23.979|26.800|38.875|
|137|VAL|CA|17.375|25.224|44.305|146|LEU|O|23.873|26.371|37.710|
|137|VAL|CB|16.834|26.694|44.238|147|VAL|N|22.940|27.297|39.523|
|137|VAL|CG1|17.988|27.738|44.134|147|VAL|CA|21.611|27.371|38.926|
|137|VAL|CG2|15.876|26.776|43.047|147|VAL|CB|20.552|27.093|40.011|
|137|VAL|C|18.531|25.152|45.317|147|VAL|CG1|19.153|27.272|39.387|
|137|VAL|O|19.711|24.982|44.974|147|VAL|CG2|20.649|25.642|40.526|
|138|ASN|N|18.136|25.179|46.588|147|VAL|C|21.405|28.740|38.305|
|138|ASN|CA|19.136|25.146|47.616|147|VAL|O|21.480|29.768|38.965|
|138|ASN|CB|18.498|25.457|48.973|148|VAL|N|21.138|28.776|37.003|
|138|ASN|CG|18.125|26.934|49.063|148|VAL|CA|21.007|30.019|36.251|
|138|ASN|OD1|18.598|27.789|48.320|148|VAL|CB|21.982|30.003|35.055|
|138|ASN|ND2|17.258|27.299|49.985|148|VAL|CG1|21.916|31.349|34.328|
|138|ASN|C|19.869|23.832|47.685|148|VAL|CG2|23.403|29.791|35.562|
|138|ASN|O|21.103|23.849|47.846|148|VAL|C|19.557|30.040|35.781|
|139|SER|N|19.209|22.709|47.506|148|VAL|O|19.127|29.064|35.128|
|139|SER|CA|19.937|21.466|47.610|149|ALA|N|18.826|31.120|36.019|
|139|SER|CB|19.001|20.303|47.649|149|ALA|CA|17.387|31.187|35.758|
|139|SER|OG|18.203|20.407|46.479|149|ALA|CB|16.610|31.028|37.063|
|139|SER|C|20.860|21.316|46.403|149|ALA|C|16.952|32.515|35.111|
|139|SER|O|22.027|20.902|46.586|149|ALA|O|17.539|33.555|35.396|
|140|ALA|N|20.431|21.663|45.160|150|ALA|N|15.931|32.454|34.249|
|140|ALA|CA|21.392|21.545|44.053|150|ALA|CA|15.375|33.605|33.549|
|140|ALA|CB|20.755|21.895|42.723|150|ALA|CB|14.427|33.109|32.448|
|140|ALA|C|22.593|22.460|44.264|150|ALA|C|14.588|34.558|34.469|
|140|ALA|O|23.740|22.070|44.057|150|ALA|O|13.789|34.092|35.290|
|141|THR|N|22.377|23.682|44.756|151|SER|N|14.717|35.878|34.313|
|141|THR|CA|23.473|24.599|45.081|151|SER|CA|13.991|36.841|35.145|
|141|THR|CB|22.851|25.918|45.587|151|SER|CB|14.526|38.284|34.979|
|141|THR|OG1|22.034|26.472|44.549|151|SER|OG|14.430|38.730|33.630|
|141|THR|CG2|23.908|26.914|45.924|151|SER|C|12.485|36.873|34.867|
|141|THR|C|24.419|23.994|46.121|151|SER|O|11.692|37.218|35.761|
|141|THR|O|25.644|24.054|45.907|152|GLY|N|12.062|36.534|33.633|
|142|SER|N|23.975|23.363|47.202|152|GLY|CA|10.646|36.425|33.269|
|142|SER|CA|24.937|22.839|48.134|152|GLY|C|10.382|37.457|32.193|
|142|SER|CB|24.216|22.599|49.442|152|GLY|O|11.117|38.447|32.024|
|142|SER|OG|23.086|21.786|49.207|153|ASN|N|9.271|37.263|31.499|
|142|SER|C|25.620|21.592|47.583|153|ASN|CA|8.969|38.082|30.352|
|142|SER|O|26.616|21.131|48.150|153|ASN|CB|8.689|37.237|29.116|
|143|ARG|N|25.155|21.025|46.447|153|ASN|CG|9.865|36.443|28.658|
|143|ARG|CA|25.865|19.945|45.761|153|ASN|OD1|11.041|36.707|28.880|
|143|ARG|CB|24.848|18.907|45.261|153|ASN|ND2|9.501|35.396|27.943|
|143|ARG|CG|24.269|18.107|46.467|153|ASN|C|7.759|38.990|30.526|
|143|ARG|CD|23.132|17.127|46.152|153|ASN|O|7.190|39.421|29.524|

FIG.1H

| | | | | | | | | | | | |
|---|---|---|---|---|---|---|---|---|---|---|---|
| 154 | SER | N | 7.390 | 39.398 | 31.739 | 164 | ARG | CB | 12.939 | 36.127 | 43.071 |
| 154 | SER | CA | 6.193 | 40.206 | 31.915 | 164 | ARG | CG | 12.741 | 37.084 | 44.237 |
| 154 | SER | CB | 5.577 | 39.973 | 33.284 | 164 | ARG | CD | 13.377 | 38.408 | 43.906 |
| 154 | SER | OG | 6.365 | 40.558 | 34.319 | 164 | ARG | NE | 13.251 | 39.367 | 44.988 |
| 154 | SER | C | 6.534 | 41.682 | 31.798 | 164 | ARG | CZ | 14.206 | 39.530 | 45.901 |
| 154 | SER | O | 5.599 | 42.468 | 31.793 | 164 | ARG | NH1 | 14.020 | 40.475 | 46.838 |
| 155 | GLY | N | 7.805 | 42.092 | 31.773 | 164 | ARG | NH2 | 15.289 | 38.737 | 45.965 |
| 155 | GLY | CA | 8.154 | 43.499 | 31.759 | 164 | ARG | C | 15.032 | 35.123 | 43.973 |
| 155 | GLY | C | 8.028 | 44.150 | 33.143 | 164 | ARG | O | 15.559 | 35.875 | 44.807 |
| 155 | GLY | O | 8.292 | 45.349 | 33.278 | 165 | TYR | N | 15.147 | 33.808 | 44.046 |
| 156 | ALA | N | 7.640 | 43.439 | 34.195 | 165 | TYR | CA | 15.787 | 33.157 | 45.176 |
| 156 | ALA | CA | 7.476 | 44.065 | 35.498 | 165 | TYR | CB | 15.503 | 31.609 | 45.150 |
| 156 | ALA | CB | 6.649 | 43.170 | 36.405 | 165 | TYR | CG | 14.046 | 31.230 | 45.501 |
| 156 | ALA | C | 8.814 | 44.359 | 36.187 | 165 | TYR | CD1 | 13.399 | 31.807 | 46.600 |
| 156 | ALA | O | 9.864 | 43.754 | 35.891 | 165 | TYR | CE1 | 12.084 | 31.484 | 46.885 |
| 157 | SER | N | 8.746 | 45.315 | 37.132 | 165 | TYR | CD2 | 13.379 | 30.328 | 44.696 |
| 157 | SER | CA | 9.857 | 45.747 | 37.932 | 165 | TYR | CE2 | 12.067 | 30.003 | 44.992 |
| 157 | SER | CB | 9.592 | 47.150 | 38.402 | 165 | TYR | CZ | 11.444 | 30.587 | 46.078 |
| 157 | SER | OG | 8.442 | 47.158 | 39.213 | 165 | TYR | OH | 10.133 | 30.227 | 46.357 |
| 157 | SER | C | 10.085 | 44.828 | 39.123 | 165 | TYR | C | 17.293 | 33.408 | 45.179 |
| 157 | SER | O | 10.623 | 45.251 | 40.147 | 165 | TYR | O | 17.996 | 33.477 | 44.141 |
| 158 | SER | N | 9.695 | 43.568 | 39.049 | 166 | ALA | N | 17.829 | 33.600 | 46.368 |
| 158 | SER | CA | 10.126 | 42.600 | 40.061 | 166 | ALA | CA | 19.222 | 33.986 | 46.544 |
| 158 | SER | CB | 9.046 | 42.518 | 41.150 | 166 | ALA | CB | 19.552 | 34.070 | 48.042 |
| 158 | SER | OG | 7.823 | 41.997 | 40.640 | 166 | ALA | C | 20.231 | 33.070 | 45.878 |
| 158 | SER | C | 10.335 | 41.293 | 39.275 | 166 | ALA | O | 21.192 | 33.553 | 45.278 |
| 158 | SER | O | 9.682 | 41.091 | 38.225 | 167 | ASN | N | 19.920 | 31.767 | 45.871 |
| 159 | ILE | N | 11.265 | 40.413 | 39.718 | 167 | ASN | CA | 20.860 | 30.806 | 45.280 |
| 159 | ILE | CA | 11.600 | 39.245 | 38.894 | 167 | ASN | CB | 20.778 | 29.446 | 46.048 |
| 159 | ILE | CB | 13.164 | 39.024 | 38.847 | 167 | ASN | CG | 21.566 | 29.545 | 47.374 |
| 159 | ILE | CG2 | 13.801 | 40.300 | 38.272 | 167 | ASN | OD1 | 22.592 | 30.238 | 47.502 |
| 159 | ILE | CG1 | 13.729 | 38.612 | 40.201 | 167 | ASN | ND2 | 21.130 | 28.931 | 48.461 |
| 159 | ILE | CD | 15.208 | 38.246 | 40.013 | 167 | ASN | C | 20.712 | 30.572 | 43.776 |
| 159 | ILE | C | 10.906 | 37.978 | 39.381 | 167 | ASN | O | 21.411 | 29.727 | 43.205 |
| 159 | ILE | O | 10.454 | 37.888 | 40.528 | 168 | ALA | N | 19.760 | 31.248 | 43.121 |
| 160 | SER | N | 10.806 | 36.974 | 38.510 | 168 | ALA | CA | 19.673 | 31.167 | 41.683 |
| 160 | SER | CA | 10.114 | 35.754 | 38.841 | 168 | ALA | CB | 18.206 | 31.007 | 41.284 |
| 160 | SER | CB | 9.658 | 35.097 | 37.513 | 168 | ALA | C | 20.259 | 32.481 | 41.121 |
| 160 | SER | OG | 10.700 | 34.817 | 36.581 | 168 | ALA | O | 19.961 | 33.600 | 41.595 |
| 160 | SER | C | 10.947 | 34.777 | 39.691 | 169 | MET | N | 21.005 | 32.366 | 40.015 |
| 160 | SER | O | 12.152 | 34.921 | 39.958 | 169 | MET | CA | 21.563 | 33.497 | 39.321 |
| 161 | TYR | N | 10.265 | 33.738 | 40.148 | 169 | MET | CB | 22.854 | 33.069 | 38.636 |
| 161 | TYR | CA | 10.867 | 32.645 | 40.876 | 169 | MET | CG | 23.476 | 34.273 | 37.972 |
| 161 | TYR | CB | 9.887 | 32.231 | 41.988 | 169 | MET | SD | 25.057 | 33.851 | 37.212 |
| 161 | TYR | CG | 9.698 | 33.315 | 43.030 | 169 | MET | CE | 25.641 | 35.532 | 37.199 |
| 161 | TYR | CD1 | 10.614 | 33.397 | 44.072 | 169 | MET | C | 20.493 | 33.939 | 38.305 |
| 161 | TYR | CE1 | 10.459 | 34.368 | 45.057 | 169 | MET | O | 19.998 | 33.150 | 37.484 |
| 161 | TYR | CD2 | 8.619 | 34.189 | 42.939 | 170 | ALA | N | 20.047 | 35.196 | 38.436 |
| 161 | TYR | CE2 | 8.459 | 35.175 | 43.906 | 170 | ALA | CA | 18.956 | 35.777 | 37.681 |
| 161 | TYR | CZ | 9.384 | 35.241 | 44.953 | 170 | ALA | CB | 18.208 | 36.758 | 38.591 |
| 161 | TYR | OH | 9.270 | 36.241 | 45.896 | 170 | ALA | C | 19.430 | 36.504 | 36.432 |
| 161 | TYR | C | 11.101 | 31.499 | 39.865 | 170 | ALA | O | 20.278 | 37.405 | 36.596 |
| 161 | TYR | O | 10.257 | 31.307 | 38.975 | 171 | VAL | N | 18.927 | 36.158 | 35.241 |
| 162 | PRO | N | 12.153 | 30.681 | 39.954 | 171 | VAL | CA | 19.332 | 36.739 | 33.966 |
| 162 | PRO | CD | 12.388 | 29.536 | 39.042 | 171 | VAL | CB | 19.862 | 35.590 | 33.075 |
| 162 | PRO | CA | 13.162 | 30.687 | 41.003 | 171 | VAL | CG1 | 20.380 | 36.267 | 31.766 |
| 162 | PRO | CB | 13.715 | 29.232 | 40.966 | 171 | VAL | CG2 | 20.946 | 34.749 | 33.786 |
| 162 | PRO | CG | 13.726 | 28.915 | 39.470 | 171 | VAL | C | 18.192 | 37.445 | 33.235 |
| 162 | PRO | C | 14.243 | 31.756 | 40.879 | 171 | VAL | O | 17.145 | 36.824 | 32.979 |
| 162 | PRO | O | 15.044 | 31.845 | 41.789 | 172 | GLY | N | 18.474 | 38.712 | 32.887 |
| 163 | ALA | N | 14.352 | 32.580 | 39.814 | 172 | GLY | CA | 17.594 | 39.568 | 32.123 |
| 163 | ALA | CA | 15.393 | 33.575 | 39.716 | 172 | GLY | C | 18.038 | 39.553 | 30.640 |
| 163 | ALA | CB | 15.165 | 34.416 | 38.441 | 172 | GLY | O | 19.106 | 39.023 | 30.302 |
| 163 | ALA | C | 15.538 | 34.529 | 40.935 | 173 | ALA | N | 17.231 | 40.184 | 29.781 |
| 163 | ALA | O | 16.640 | 34.874 | 41.399 | 173 | ALA | CA | 17.461 | 40.220 | 28.347 |
| 164 | ARG | N | 14.417 | 34.878 | 41.559 | 173 | ALA | CB | 16.278 | 39.626 | 27.617 |
| 164 | ARG | CA | 14.385 | 35.740 | 42.745 | 173 | ALA | C | 17.667 | 41.631 | 27.812 |

FIG. 1I

| | | | | | | | | | | |
|---|---|---|---|---|---|---|---|---|---|---|
|173|ALA|O|16.987|42.599|28.169|182|SER|CB|9.735|46.338|25.967|
|174|THR|N|18.639|41.714|26.910|182|SER|OG|9.316|45.472|24.927|
|174|THR|CA|18.993|42.944|26.178|182|SER|C|10.061|44.602|27.814|
|174|THR|CB|20.504|43.281|26.349|182|SER|O|9.557|44.957|28.879|
|174|THR|OG1|21.329|42.130|26.074|183|PHE|N|10.058|43.321|27.403|
|174|THR|CG2|20.733|43.727|27.767|183|PHE|CA|9.501|42.231|28.191|
|174|THR|C|18.715|42.787|24.688|183|PHE|CB|9.261|40.999|27.282|
|174|THR|O|18.622|41.662|24.148|183|PHE|CG|10.501|40.486|26.518|
|175|ASP|N|18.674|43.934|24.029|183|PHE|CD1|11.508|39.734|27.142|
|175|ASP|CA|18.518|43.907|22.588|183|PHE|CD2|10.653|40.840|25.173|
|175|ASP|CB|17.388|44.840|22.148|183|PHE|CE1|12.617|39.325|26.421|
|175|ASP|CG|17.584|46.353|22.386|183|PHE|CE2|11.782|40.415|24.478|
|175|ASP|OD1|18.675|46.844|22.682|183|PHE|CZ|12.774|39.665|25.095|
|175|ASP|OD2|16.579|47.047|22.291|183|PHE|C|10.359|41.795|29.380|
|174|ASP|C|19.794|44.258|21.834|183|PHE|O|9.889|41.025|30.246|
|175|ASP|O|20.844|44.480|22.440|184|SER|N|11.615|42.247|29.427|
|176|GLN|N|19.724|44.498|20.516|184|SER|CA|12.551|41.670|30.410|
|176|GLN|CA|20.938|44.742|19.737|184|SER|CB|13.998|42.030|30.045|
|176|GLN|CB|20.702|44.722|18.237|184|SER|OG|14.926|41.420|30.947|
|176|GLN|CG|20.123|43.400|17.797|184|SER|C|12.281|42.125|31.843|
|176|GLN|CD|18.592|43.272|17.887|184|SER|O|12.450|43.331|32.137|
|176|GLN|OE1|17.837|44.022|18.543|185|GLN|N|11.911|41.197|32.727|
|176|GLN|NE2|18.083|42.254|17.196|185|GLN|CA|11.652|41.622|34.089|
|176|GLN|C|21.534|46.084|20.056|185|GLN|CB|11.034|40.489|34.904|
|176|GLN|O|22.690|46.302|19.783|185|GLN|CG|9.595|40.335|34.482|
|177|ASN|N|20.836|46.989|20.719|185|GLN|CD|8.912|39.174|35.165|
|177|ASN|CA|21.382|48.288|21.098|185|GLN|OE1|8.817|39.005|36.377|
|177|ASN|CB|20.321|49.300|20.975|185|GLN|NE2|8.397|38.320|34.331|
|177|ASN|CG|19.832|49.550|19.587|185|GLN|C|12.960|42.075|34.773|
|177|ASN|OD1|20.577|49.605|18.631|185|GLN|O|14.066|41.606|34.458|
|177|ASN|ND2|18.526|49.678|19.484|186|TYR|N|12.871|43.046|35.676|
|177|ASN|C|21.895|48.299|22.521|186|TYR|CA|14.048|43.618|36.349|
|177|ASN|O|22.380|49.322|23.026|186|TYR|CB|14.488|44.924|35.634|
|178|ASN|N|21.875|47.139|23.202|186|TYR|CG|13.385|45.992|35.576|
|178|ASN|CA|22.256|47.033|24.623|186|TYR|CD1|12.362|45.872|34.635|
|178|ASN|CB|23.735|47.479|24.896|186|TYR|CE1|11.347|46.805|34.553|
|178|ASN|CG|24.734|46.515|24.314|186|TYR|CD2|13.385|47.049|36.468|
|178|ASN|OD1|24.433|45.324|24.210|186|TYR|CE2|12.386|47.988|36.396|
|178|ASN|ND2|25.920|46.928|23.917|186|TYR|CZ|11.376|47.855|35.450|
|178|ASN|C|21.345|47.835|25.547|186|TYR|OH|10.418|48.846|35.328|
|178|ASN|O|21.747|48.392|26.576|186|TYR|C|13.735|43.925|37.819|
|179|ASN|N|20.081|47.806|25.174|186|TYR|O|12.616|43.620|38.262|
|179|ASN|CA|19.000|48.319|26.009|186|GLY|N|14.620|44.547|38.575|
|179|ASN|CB|18.044|49.165|25.243|187|GLY|CA|14.330|44.849|39.958|
|179|ASN|CG|18.566|50.593|25.088|187|GLY|C|15.232|44.062|40.892|
|179|ASN|OD1|19.289|51.155|25.949|187|GLY|O|16.318|43.548|40.541|
|179|ASN|ND2|18.250|51.181|23.925|188|ALA|N|14.782|43.915|42.140|
|179|ASN|C|18.230|47.101|26.490|188|ALA|CA|15.616|43.340|43.172|
|179|ASN|O|18.246|46.016|25.872|188|ALA|CB|14.891|43.435|44.515|
|180|ARG|N|17.579|47.276|27.645|188|ALA|C|15.973|41.884|42.894|
|180|ARG|CA|16.734|46.241|28.230|188|ALA|O|15.134|41.065|42.549|
|180|ARG|CB|16.050|46.746|29.525|189|GLY|N|17.263|41.594|42.986|
|180|ARG|CG|15.269|45.653|30.233|189|GLY|CA|17.747|40.223|42.778|
|180|ARG|CD|14.562|46.201|31.492|189|GLY|C|18.299|39.938|41.358|
|180|ARG|NE|13.537|47.146|31.076|189|GLY|O|18.911|38.873|41.139|
|180|ARG|CZ|12.271|46.850|30.720|190|LEU|N|18.128|40.857|40.397|
|180|ARG|NH1|11.476|47.846|30.339|190|LEU|CA|18.646|40.601|39.064|
|180|ARG|NH2|11.709|45.650|30.752|190|LEU|CB|18.023|41.621|38.094|
|180|ARG|C|15.639|45.909|27.213|190|LEU|CG|18.302|41.454|36.607|
|180|ARG|O|14.991|46.855|26.715|190|LEU|CD1|17.688|40.163|36.140|
|181|ALA|N|15.377|44.644|26.848|190|LEU|CD2|17.844|42.716|35.848|
|181|ALA|CA|14.225|44.338|26.002|190|LEU|C|20.169|40.671|39.079|
|181|ALA|CB|14.266|42.883|25.663|190|LEU|O|20.776|41.624|39.589|
|181|ALA|C|12.942|44.677|26.771|191|ASP|N|20.847|39.677|38.505|
|181|ALA|O|12.873|44.495|28.009|191|ASP|CA|22.285|39.597|38.558|
|182|SER|N|11.894|45.172|26.133|191|ASP|CB|22.732|38.168|38.777|
|182|SER|CA|10.757|45.650|26.927|191|ASP|CG|22.428|37.668|40.182|

FIG.1J

| | | | | | | | | | | |
|---|---|---|---|---|---|---|---|---|---|---|
|191|ASP|OD1|22.903|38.250|41.148|201|SER|CA|19.476|28.584|17.356|
|191|ASP|OD2|21.685|36.717|40.309|201|SER|CB|19.283|28.528|18.891|
|191|ASP|C|23.037|40.095|37.355|201|SER|OG|20.089|27.563|19.530|
|191|ASP|O|24.122|40.674|37.449|201|SER|C|18.875|27.346|16.701|
|192|ILE|N|22.464|39.842|36.171|201|SER|O|18.062|27.448|15.779|
|192|ILE|CA|23.192|40.070|34.908|202|THR|N|19.318|26.189|17.171|
|192|ILE|CB|24.291|38.919|34.852|202|THR|CA|18.879|24.880|16.747|
|192|ILE|CG2|23.628|37.619|34.325|202|THR|CB|19.769|23.760|17.461|
|192|ILE|CG1|25.513|39.314|34.012|202|THR|OG1|19.869|24.043|18.866|
|192|ILE|CD|26.686|38.323|34.226|202|THR|CG2|21.204|23.712|16.888|
|192|ILE|C|22.176|40.008|33.774|202|THR|C|17.412|24.706|17.082|
|192|ILE|O|21.020|39.545|33.967|202|THR|O|16.901|25.159|18.115|
|193|VAL|N|22.644|40.477|32.608|203|TYR|N|16.712|23.986|16.227|
|193|VAL|CA|21.847|40.379|31.392|203|TYR|CA|15.286|23.728|16.398|
|193|VAL|CB|21.246|41.745|30.945|203|TYR|CB|14.508|24.820|15.615|
|193|VAL|CG1|20.189|42.187|31.967|203|TYR|CG|13.165|25.140|16.239|
|193|VAL|CG2|22.326|42.772|30.755|203|TYR|CD1|13.129|25.884|17.421|
|193|VAL|C|22.653|39.820|30.203|203|TYR|CE1|11.918|26.223|17.992|
|193|VAL|O|23.885|39.799|30.174|203|TYR|CD2|11.996|24.708|15.619|
|194|ALA|N|21.891|39.376|29.204|203|TYR|CE2|10.770|25.044|16.193|
|194|ALA|CA|22.453|38.810|28.000|203|TYR|CZ|10.757|25.798|17.369|
|194|ALA|CB|22.770|37.303|28.253|203|TYR|OH|9.560|26.166|17.949|
|194|ALA|C|21.446|38.965|26.837|203|TYR|C|14.941|22.322|15.901|
|194|ALA|O|20.264|39.273|27.044|203|TYR|O|15.658|21.779|15.040|
|195|PRO|N|21.872|38.794|25.576|204|PRO|N|13.905|21.662|16.450|
|195|PRO|CD|23.294|38.583|25.188|204|PRO|CD|13.057|22.111|17.596|
|195|PRO|CA|21.018|38.880|24.377|204|PRO|CA|13.468|20.319|15.980|
|195|PRO|CB|21.899|38.465|23.180|204|PRO|CB|12.178|20.026|16.797|
|195|PRO|CG|23.321|38.854|23.643|204|PRO|CG|12.414|20.819|18.098|
|195|PRO|C|19.802|38.002|24.479|204|PRO|C|13.249|20.306|14.463|
|195|PRO|O|19.931|36.816|24.761|204|PRO|O|12.965|21.337|13.825|
|196|GLY|N|18.648|38.574|24.192|205|GLY|N|13.473|19.119|13.895|
|196|GLY|CA|17.403|37.833|24.257|205|GLY|CA|13.358|18.927|12.435|
|196|GLY|C|16.401|38.217|23.175|205|GLY|C|14.643|19.310|11.724|
|196|GLY|O|15.214|37.925|23.303|205|GLY|O|14.632|19.630|10.535|
|197|VAL|N|16.829|38.890|22.088|206|SER|N|15.770|19.252|12.442|
|197|VAL|CA|15.888|39.285|21.035|206|SER|CA|17.067|19.586|11.924|
|197|VAL|CB|15.690|40.877|21.010|206|SER|CB|17.523|18.417|11.036|
|197|VAL|CG1|14.919|41.323|19.738|206|SER|OG|17.461|17.216|11.797|
|197|VAL|CG2|15.038|41.327|22.327|206|SER|C|17.098|20.931|11.175|
|197|VAL|C|16.483|38.785|19.727|206|SER|O|17.591|21.045|10.047|
|197|VAL|O|17.672|38.897|19.432|207|THR|N|16.566|21.968|11.842|
|198|ASN|N|15.627|38.173|18.937|207|THR|CA|16.518|23.294|11.258|
|198|ASN|CA|15.957|37.626|17.630|207|THR|CB|15.070|23.518|10.667|
|198|ASN|CB|16.220|38.703|16.520|207|THR|OG1|15.190|24.695|9.866|
|198|ASN|CG|15.814|38.095|15.160|207|THR|CG2|13.924|23.606|11.700|
|198|ASN|OD1|15.010|37.149|15.093|207|THR|C|16.928|24.275|12.354|
|198|ASN|ND2|16.255|38.621|14.013|207|THR|O|17.600|23.908|13.342|
|198|ASN|C|17.160|36.718|17.695|208|TYR|N|16.632|25.546|12.113|
|198|ASN|O|18.147|36.910|16.978|208|TYR|CA|17.071|26.693|12.914|
|199|VAL|N|17.039|35.746|18.605|208|TYR|CB|18.333|27.321|12.307|
|199|VAL|CA|18.096|34.791|18.849|208|TYR|CG|19.364|26.245|12.061|
|199|VAL|CB|18.135|34.490|20.377|208|TYR|CD1|19.428|25.565|10.842|
|199|VAL|CG1|19.303|33.623|20.702|208|TYR|CE1|20.274|24.513|10.648|
|199|VAL|CG2|18.493|35.732|21.205|208|TYR|CD2|20.152|25.869|13.110|
|199|VAL|C|17.872|33.522|18.017|208|TYR|CE2|20.978|24.825|12.917|
|199|VAL|O|16.912|32.776|18.194|208|TYR|CZ|21.039|24.151|11.713|
|200|GLN|N|18.706|33.324|17.005|208|TYR|OH|21.935|23.103|11.601|
|200|GLN|CA|18.771|32.144|16.138|208|TYR|C|15.936|27.689|12.911|
|200|GLN|CB|19.584|32.515|14.908|208|TYR|O|15.224|27.863|11.906|
|200|GLN|CG|19.819|31.348|13.964|209|ALA|N|15.728|28.316|14.076|
|200|GLN|CD|20.240|31.677|12.544|209|ALA|CA|14.653|29.234|14.266|
|200|GLN|OE1|21.324|32.176|12.338|209|ALA|CB|13.489|28.384|14.707|
|200|GLN|NE2|19.592|31.494|11.476|209|ALA|C|15.041|30.312|15.266|
|200|GLN|C|19.433|30.946|16.796|209|ALA|O|16.021|30.178|16.019|
|200|GLN|O|20.567|31.114|17.277|210|SER|N|14.378|31.450|15.089|
|201|SER|N|18.810|29.768|16.799|210|SER|CA|14.567|32.642|15.914|

FIG.1K

```
210 SER  CB   14.614 33.893 15.065    220 HIS  CG   23.307 34.345 25.237
210 SER  OG   15.788 33.756 14.342    220 HIS  CD2  24.010 34.501 24.048
210 SER  C    13.456 32.819 16.920    220 HIS  ND1  21.999 34.359 24.936
210 SER  O    12.255 32.689 16.610    220 HIS  CE1  21.849 34.518 23.642
211 SER  N    13.895 33.079 18.152    220 HIS  NE2  23.064 34.607 23.115
211 LEU  CA   12.990 33.304 19.244    220 HIS  C    25.048 32.824 28.410
211 LEU  CB   12.963 32.089 20.118    220 HIS  O    26.276 32.626 28.383
211 LEU  CG   12.368 30.848 19.535    221 VAL  N    24.370 32.933 29.566
211 LEU  CD1  12.346 29.857 20.657    221 VAL  CA   25.084 32.989 30.830
211 LEU  CD2  10.940 31.056 19.033    221 VAL  CB   24.180 33.727 31.843
211 LEU  C    13.372 34.503 20.110    221 VAL  CG1  24.746 33.674 33.267
211 LEU  O    14.547 34.927 20.110    221 VAL  CG2  24.119 35.194 31.366
212 ASN  N    12.439 35.024 20.912    221 VAL  C    25.477 31.606 31.299
212 ASN  CA   12.734 36.191 21.741    221 VAL  O    26.612 31.424 31.734
212 ASN  CB   11.883 37.403 21.413    222 ALA  N    24.617 30.614 31.120
212 ASN  CG   11.961 37.853 19.972    222 ALA  CA   24.981 29.223 31.421
212 ASN  OD1  12.979 38.246 19.415    222 ALA  CB   23.871 28.283 31.032
212 ASN  ND2  10.841 37.797 19.283    222 ALA  C    26.229 28.786 30.670
212 ASN  C    12.354 35.787 23.156    222 ALA  O    27.129 28.121 31.204
212 ASN  O    11.336 35.119 23.350    223 GLY  N    26.258 29.180 29.388
213 GLY  N    13.070 36.197 24.217    223 GLY  CA   27.463 28.928 28.649
213 GLY  CA   12.648 35.928 25.599    223 GLY  C    28.715 29.661 29.070
213 GLY  C    13.834 35.974 26.520    223 GLY  O    29.806 29.064 29.098
213 GLY  O    14.990 35.843 26.099    224 ALA  N    28.557 30.955 29.357
214 THR  N    13.583 36.141 27.832    224 ALA  CA   29.708 31.677 29.842
214 THR  CA   14.658 36.016 28.829    224 ALA  CB   29.313 33.106 30.058
214 THR  CB   14.204 36.523 30.242    224 ALA  C    30.261 31.051 31.147
214 THR  OG1  12.998 35.812 30.594    224 ALA  O    31.463 30.894 31.314
214 THR  CG2  14.014 38.055 30.271    225 ALA  N    29.387 30.580 32.016
214 THR  C    15.128 34.527 28.894    225 ALA  CA   29.771 29.836 33.221
214 THR  O    16.253 34.214 29.302    225 ALA  CB   28.560 29.321 34.020
215 SER  N    14.304 33.607 28.380    225 ALA  C    30.593 28.603 32.864
215 SER  CA   14.663 32.187 28.217    225 ALA  O    31.630 28.374 33.487
215 SER  CB   13.425 31.449 27.696    226 ALA  N    30.248 27.816 31.843
215 SER  OG   12.324 31.235 28.564    226 ALA  CA   31.033 26.664 31.490
215 SER  C    15.860 31.981 27.237    226 ALA  CB   30.292 25.958 30.380
215 SER  O    16.588 30.993 27.305    226 ALA  C    32.446 27.078 31.054
216 MET  N    16.039 32.907 26.272    226 ALA  O    33.421 26.381 31.370
216 MET  CA   17.165 32.901 25.324    227 LEU  N    32.587 28.209 30.328
216 MET  CB   16.776 33.575 24.055    227 LEU  CA   33.888 28.734 29.901
216 MET  CG   15.843 32.791 23.121    227 LEU  CB   33.691 29.983 28.955
216 MET  SD   14.133 32.519 23.660    227 LEU  CG   32.901 29.762 27.666
216 MET  CE   14.311 30.783 23.925    227 LEU  CD1  32.816 31.015 26.813
216 MET  C    18.372 33.638 25.885    227 LEU  CD2  33.598 28.704 26.902
216 MET  O    19.506 33.386 25.460    227 LEU  C    34.782 29.060 31.088
217 ALA  N    18.136 34.558 26.845    227 LEU  O    35.954 28.623 31.131
217 ALA  CA   19.249 35.257 27.465    228 VAL  N    34.176 29.711 32.105
217 ALA  CB   18.739 36.485 28.240    228 VAL  CA   34.951 30.076 33.286
217 ALA  C    19.991 34.343 28.432    228 VAL  CB   34.114 31.094 34.168
217 ALA  O    21.223 34.249 28.386    228 VAL  CG1  34.822 31.451 35.502
218 THR  N    19.211 33.574 29.199    228 VAL  CG2  33.950 32.402 33.362
218 THR  CA   19.756 32.657 30.231    228 VAL  C    35.340 28.814 34.074
218 THR  CB   18.587 31.860 30.888    228 VAL  O    36.468 28.777 34.573
218 THR  OG1  17.719 32.837 31.429    229 LYS  N    34.502 27.781 34.115
218 THR  CG2  19.040 30.887 31.979    229 LYS  CA   34.817 26.566 34.865
218 THR  C    20.824 31.704 29.700    229 LYS  CB   33.575 25.679 34.978
218 THR  O    21.912 31.648 30.275    229 LYS  CG   33.758 24.324 35.713
219 PRO  N    20.683 31.008 28.586    229 LYS  CD   34.180 24.479 37.170
219 PRO  CD   19.479 30.843 27.793    229 LYS  CE   34.230 23.097 37.844
219 PRO  CA   21.708 30.099 28.089    229 LYS  NZ   34.394 23.211 39.298
219 PRO  CB   21.074 29.384 26.909    229 LYS  C    35.919 25.792 34.170
219 PRO  CG   19.943 30.268 26.471    229 LYS  O    36.804 25.233 34.841
219 PRO  C    23.027 30.765 27.704    230 GLN  N    35.915 25.679 32.835
219 PRO  O    24.060 30.108 27.745    230 GLN  CA   37.001 24.957 32.188
220 HIS  N    22.994 32.051 27.346    230 GLN  CB   36.692 24.852 30.683
220 HIS  CA   24.239 32.770 27.094    230 GLN  CG   37.819 24.181 29.916
220 HIS  CB   23.997 34.219 26.600    230 GLN  CD   37.806 24.343 28.410
```

FIG.1L

| 230 | GLN | OE1 | 36.941 | 24.907 | 27.731 | 238 | VAL | C   | 30.741 | 31.770 | 43.322 |
| 230 | GLN | NE2 | 38.866 | 23.779 | 27.864 | 238 | VAL | O   | 30.584 | 32.955 | 42.971 |
| 230 | GLN | C   | 38.324 | 25.710 | 32.453 | 239 | GLN | N   | 31.903 | 31.146 | 43.181 |
| 230 | GLN | O   | 39.365 | 25.106 | 32.722 | 239 | GLN | CA  | 33.058 | 31.865 | 42.654 |
| 231 | LYS | N   | 38.320 | 27.043 | 32.369 | 239 | GLN | CB  | 34.348 | 31.007 | 42.712 |
| 231 | LYS | CA  | 39.482 | 27.877 | 32.678 | 239 | GLN | CG  | 34.787 | 30.771 | 44.165 |
| 231 | LYS | CB  | 39.085 | 29.347 | 32.389 | 239 | GLN | CD  | 36.001 | 29.847 | 44.293 |
| 231 | LYS | CG  | 40.041 | 30.518 | 32.637 | 239 | GLN | OE1 | 35.946 | 28.629 | 44.354 |
| 231 | LYS | CD  | 41.380 | 30.478 | 31.945 | 239 | GLN | NE2 | 37.174 | 30.441 | 44.326 |
| 231 | LYS | CE  | 42.078 | 31.872 | 31.997 | 239 | GLN | C   | 32.811 | 32.264 | 41.203 |
| 231 | LYS | NZ  | 42.377 | 32.352 | 33.343 | 239 | GLN | O   | 33.124 | 33.398 | 40.784 |
| 231 | LYS | C   | 39.970 | 27.715 | 34.142 | 240 | ILE | N   | 32.261 | 31.291 | 40.463 |
| 231 | LYS | O   | 41.173 | 27.658 | 34.409 | 240 | ILE | CA  | 31.950 | 31.500 | 39.047 |
| 232 | ASN | N   | 39.023 | 27.635 | 35.097 | 240 | ILE | CB  | 31.410 | 30.186 | 38.368 |
| 232 | ASN | CA  | 39.292 | 27.588 | 36.520 | 240 | ILE | CG2 | 31.025 | 30.399 | 36.876 |
| 232 | ASN | CB  | 38.801 | 28.848 | 37.227 | 240 | ILE | CG1 | 32.503 | 29.161 | 38.463 |
| 232 | ASN | CG  | 39.339 | 30.115 | 36.617 | 240 | ILE | CD  | 32.041 | 27.775 | 37.973 |
| 232 | ASN | OD1 | 40.486 | 30.464 | 36.859 | 240 | ILE | C   | 30.902 | 32.584 | 38.896 |
| 232 | ASN | ND2 | 38.537 | 30.834 | 35.845 | 240 | ILE | O   | 31.087 | 33.511 | 38.104 |
| 232 | ASN | C   | 38.595 | 26.402 | 37.158 | 241 | ARG | N   | 29.819 | 32.484 | 39.667 |
| 232 | ASN | O   | 37.635 | 26.555 | 37.907 | 251 | ARG | CA  | 28.769 | 33.495 | 39.638 |
| 233 | PRO | N   | 39.057 | 25.173 | 36.945 | 241 | ARG | CB  | 27.701 | 33.092 | 40.655 |
| 233 | PRO | CD  | 40.245 | 24.847 | 36.150 | 241 | ARG | CG  | 26.634 | 34.192 | 40.895 |
| 233 | PRO | CA  | 38.320 | 23.978 | 37.376 | 241 | ARG | CD  | 25.462 | 33.692 | 41.771 |
| 233 | PRO | CB  | 39.053 | 22.819 | 36.729 | 241 | ARG | NE  | 24.364 | 34.639 | 41.945 |
| 233 | PRO | CG  | 40.441 | 23.367 | 36.519 | 241 | ARG | CZ  | 23.323 | 34.340 | 42.749 |
| 233 | PRO | C   | 38.155 | 23.820 | 38.863 | 241 | ARG | NH1 | 22.325 | 35.215 | 42.920 |
| 233 | PRO | O   | 37.266 | 23.094 | 39.274 | 241 | ARG | NH2 | 23.252 | 33.149 | 43.371 |
| 234 | SER | N   | 38.962 | 24.489 | 39.675 | 241 | ARG | C   | 29.313 | 34.923 | 39.937 |
| 234 | SER | CA  | 38.725 | 24.374 | 41.124 | 241 | ARG | O   | 29.037 | 35.874 | 39.200 |
| 234 | SER | CB  | 40.005 | 24.643 | 41.961 | 242 | ASN | N   | 30.153 | 35.073 | 40.959 |
| 234 | SER | OG  | 40.378 | 26.007 | 41.847 | 242 | ASN | CA  | 30.649 | 36.413 | 41.277 |
| 234 | SER | C   | 37.635 | 25.309 | 41.680 | 242 | ASN | CB  | 31.391 | 36.455 | 42.609 |
| 234 | SER | O   | 37.203 | 25.124 | 42.824 | 242 | ASN | CG  | 30.386 | 36.371 | 43.746 |
| 235 | TRP | N   | 37.151 | 26.270 | 40.878 | 242 | ASN | OD1 | 29.177 | 36.652 | 43.659 |
| 235 | TRP | CA  | 36.213 | 27.246 | 41.393 | 242 | ASN | ND2 | 30.877 | 35.881 | 44.877 |
| 235 | TRP | CB  | 36.022 | 28.366 | 40.435 | 242 | ASN | C   | 31.591 | 36.931 | 40.225 |
| 235 | TRP | CG  | 37.165 | 29.323 | 40.391 | 242 | ASN | O   | 31.631 | 38.152 | 39.938 |
| 235 | TRP | CD2 | 37.103 | 30.539 | 39.761 | 243 | HIS | N   | 32.330 | 36.012 | 39.584 |
| 235 | TRP | CE2 | 38.384 | 31.011 | 39.929 | 243 | HIS | CA  | 33.284 | 36.451 | 38.593 |
| 235 | TRP | CE3 | 36.167 | 31.261 | 39.083 | 243 | HIS | CB  | 34.183 | 35.327 | 38.178 |
| 235 | TRP | CD1 | 38.405 | 29.059 | 40.930 | 243 | HIS | CG  | 35.409 | 35.790 | 37.413 |
| 235 | TRP | NE1 | 39.136 | 30.109 | 40.623 | 243 | HIS | CD2 | 36.367 | 36.638 | 37.902 |
| 235 | TRP | CZ2 | 38.726 | 32.237 | 39.404 | 243 | HIS | ND1 | 35.770 | 35.447 | 36.181 |
| 235 | TRP | CZ3 | 36.502 | 32.474 | 38.559 | 243 | HIS | CE1 | 36.908 | 36.044 | 35.892 |
| 235 | TRP | CH2 | 37.775 | 32.956 | 38.720 | 243 | HIS | NE2 | 37.250 | 36.757 | 36.945 |
| 235 | TRP | C   | 34.862 | 26.643 | 41.637 | 243 | HIS | C   | 32.559 | 36.966 | 37.370 |
| 235 | TRP | O   | 34.427 | 25.726 | 40.941 | 243 | HIS | O   | 32.988 | 37.984 | 36.820 |
| 236 | SER | N   | 34.206 | 27.137 | 42.669 | 244 | LEU | N   | 31.473 | 36.265 | 36.963 |
| 236 | SER | CA  | 32.884 | 26.712 | 43.011 | 244 | LEU | CA  | 30.709 | 36.649 | 35.801 |
| 236 | SER | CB  | 32.771 | 26.915 | 44.541 | 244 | LEU | CB  | 29.576 | 35.636 | 35.501 |
| 236 | SER | OG  | 32.691 | 28.301 | 44.902 | 244 | LEU | CG  | 29.971 | 34.234 | 34.958 |
| 236 | SER | C   | 31.891 | 27.549 | 42.200 | 244 | LEU | CD1 | 28.719 | 33.367 | 34.841 |
| 236 | SER | O   | 32.195 | 28.606 | 41.637 | 244 | LEU | CD2 | 30.649 | 34.360 | 33.602 |
| 237 | ASN | N   | 30.645 | 27.084 | 42.278 | 244 | LEU | C   | 30.147 | 38.007 | 36.104 |
| 237 | ASN | CA  | 29.495 | 27.743 | 41.705 | 244 | LEU | O   | 30.189 | 38.853 | 35.217 |
| 237 | ASN | CB  | 28.255 | 26.923 | 42.112 | 245 | LYS | N   | 29.690 | 38.289 | 37.328 |
| 237 | ASN | CG  | 27.966 | 26.679 | 43.605 | 245 | LYS | CA  | 29.178 | 39.632 | 37.654 |
| 237 | ASN | OD1 | 28.706 | 27.112 | 44.495 | 245 | LYS | CB  | 28.452 | 39.593 | 38.993 |
| 237 | ASN | ND2 | 26.851 | 26.017 | 43.928 | 245 | LYS | CG  | 27.193 | 38.687 | 38.928 |
| 237 | ASN | C   | 29.388 | 29.219 | 42.117 | 245 | LYS | CD  | 26.536 | 38.412 | 40.289 |
| 237 | ASN | O   | 29.255 | 30.109 | 41.266 | 245 | LYS | CE  | 25.811 | 39.677 | 40.573 |
| 238 | VAL | N   | 29.592 | 29.555 | 43.414 | 245 | LYS | NZ  | 25.221 | 39.607 | 41.886 |
| 238 | VAL | CA  | 29.576 | 30.945 | 43.876 | 245 | LYS | C   | 30.300 | 40.665 | 37.714 |
| 238 | VAL | CB  | 29.553 | 30.919 | 45.442 | 245 | LYS | O   | 30.125 | 41.805 | 37.257 |
| 238 | VAL | CG1 | 29.767 | 32.294 | 46.097 | 246 | ASN | N   | 31.462 | 40.279 | 38.199 |
| 238 | VAL | CG2 | 28.199 | 30.344 | 45.805 | 246 | ASN | CA  | 32.579 | 41.194 | 38.352 |

FIG.1M

| | | | | | | | | | | |
|---|---|---|---|---|---|---|---|---|---|---|
|246|ASN|CB|33.697|40.568|39.196|256|LEU|CG|16.565|49.634|34.134|
|246|ASN|CG|33.286|40.502|40.651|256|LEU|CD1|16.919|50.482|32.887|
|246|ASN|OD1|32.445|41.245|41.165|256|LEU|CD2|15.095|49.321|34.182|
|246|ASN|ND2|33.814|39.538|41.375|256|LEU|C|18.284|46.162|34.546|
|246|ASN|C|33.188|41.620|37.046|256|LEU|O|17.798|45.300|33.803|
|246|ASN|O|33.819|42.686|36.960|257|TYR|N|19.566|46.246|34.888|
|247|THR|N|33.020|40.781|36.033|257|TYR|CA|20.590|45.390|34.268|
|247|THR|CA|33.574|41.115|34.734|257|TYR|CB|21.608|46.225|33.447|
|247|THR|CB|34.386|39.916|34.179|257|TYR|CG|20.957|47.106|32.389|
|247|THR|OG1|33.492|38.818|34.055|257|TYR|CD1|20.349|46.459|31.337|
|247|THR|CG2|35.608|39.565|35.059|257|TYR|CE1|19.733|47.179|30.384|
|247|THR|C|32.516|41.547|33.737|257|TYR|CD2|20.951|48.503|32.449|
|247|THR|O|32.865|41.792|32.575|257|TYR|CE2|20.330|49.219|31.446|
|248|ALA|N|31.252|41.714|34.123|257|TYR|CZ|19.731|48.536|30.426|
|248|ALA|CA|30.213|42.085|33.162|257|TYR|OH|19.142|49.131|29.335|
|248|ALA|CB|28.829|41.914|33.800|257|TYR|C|21.424|44.557|35.226|
|248|ALA|C|30.385|43.558|32.731|257|TYR|O|22.226|43.739|34.776|
|248|ALA|O|30.961|44.395|33.440|258|GLY|N|21.305|44.756|36.542|
|249|THR|N|29.950|43.949|31.551|258|GLY|CA|22.222|44.130|37.496|
|249|THR|CA|30.001|45.323|31.096|258|GLY|C|23.630|44.552|37.201|
|249|THR|CB|29.955|45.301|29.552|258|GLY|O|23.896|45.710|36.877|
|249|THR|OG1|31.151|44.706|29.080|259|SER|N|24.511|43.586|37.273|
|249|THR|CG2|29.830|46.690|28.965|259|SER|CA|25.897|43.856|36.955|
|249|THR|C|28.830|46.105|31.676|259|SER|CB|26.747|42.633|37.239|
|249|THR|O|27.664|45.760|31.425|259|SER|OG|26.779|42.518|38.660|
|250|SER|N|29.067|47.214|32.412|259|SER|C|26.153|44.278|35.527|
|250|SER|CA|27.941|47.994|32.947|259|SER|O|27.225|44.856|35.285|
|250|SER|CB|28.405|49.102|33.875|260|GLY|N|25.225|44.013|34.600|
|250|SER|OG|27.267|49.862|34.279|260|GLY|CA|25.413|44.431|33.222|
|250|SER|C|27.136|48.631|31.822|260|GLY|C|25.476|43.210|32.331|
|250|SER|O|27.687|49.164|30.857|260|GLY|O|24.999|42.106|32.672|
|251|LEU|N|25.824|48.523|31.929|261|LEU|N|26.036|43.461|31.151|
|251|LEU|CA|24.949|49.115|30.934|261|LEU|CA|26.105|42.461|30.087|
|251|LEU|CB|24.067|48.019|30.342|261|LEU|CB|26.274|43.195|28.721|
|251|LEU|CG|24.737|46.908|29.627|261|LEU|CG|26.349|42.381|27.424|
|251|LEU|CD1|23.663|46.020|29.043|261|LEU|CD1|25.064|41.598|27.191|
|251|LEU|CD2|25.595|47.430|28.481|261|LEU|CD2|26.675|43.372|26.282|
|251|LEU|C|24.069|50.231|31.462|261|LEU|C|27.234|41.470|30.309|
|251|LEU|O|23.214|50.787|30.769|261|LEU|O|28.410|41.842|30.426|
|252|GLY|N|24.239|50.606|32.703|262|VAL|N|26.851|40.192|30.263|
|252|GLY|CA|23.317|51.538|33.279|262|VAL|CA|27.872|39.161|30.432|
|252|GLY|C|22.880|50.976|34.613|262|VAL|CB|27.227|37.754|30.407|
|252|GLY|O|23.651|50.372|35.376|262|VAL|CG1|26.633|37.448|29.036|
|253|SER|N|21.614|51.241|34.872|262|VAL|CG2|28.305|36.734|30.824|
|253|SER|CA|20.958|50.918|36.106|262|VAL|C|28.935|39.300|29.331|
|253|SER|CB|19.470|51.165|35.891|262|VAL|O|28.661|39.699|28.193|
|253|SER|OG|18.813|51.273|37.150|263|ASN|N|30.181|39.070|29.700|
|253|SER|C|21.195|49.492|36.567|263|ASN|CA|31.271|39.216|28.755|
|253|SER|O|20.900|48.587|35.786|263|ASN|CB|31.866|40.599|28.993|
|254|THR|N|21.694|49.321|37.796|263|ASN|CG|33.072|40.880|28.136|
|254|THR|CA|21.773|48.021|38.431|263|ASN|OD1|33.666|40.009|27.502|
|254|THR|CB|22.417|48.071|39.869|263|ASN|ND2|33.498|42.124|28.143|
|254|THR|OG1|23.694|48.691|39.803|263|ASN|C|32.250|38.068|28.945|
|254|THR|CG2|22.671|46.670|40.414|263|ASN|O|33.119|37.994|29.826|
|254|THR|C|20.311|47.594|38.557|264|ALA|N|32.136|37.126|28.030|
|254|THR|O|20.041|46.419|38.445|264|ALA|CA|32.947|35.931|28.088|
|255|ASN|N|19.316|48.480|38.694|264|ALA|CB|32.528|34.857|27.080|
|255|ASN|CA|17.930|48.038|38.783|264|ALA|C|34.404|36.250|27.801|
|255|ASN|CB|17.061|49.253|39.031|264|ALA|O|35.259|35.517|28.331|
|255|ASN|CG|15.600|48.927|39.271|265|GLU|N|34.752|37.304|27.054|
|255|ASN|OD1|15.191|48.158|40.157|265|GLU|CA|36.169|37.625|26.884|
|255|ASN|ND2|14.771|49.580|38.459|265|GLU|CB|36.346|38.768|25.842|
|255|ASN|C|17.441|47.296|37.526|265|GLU|CG|37.790|39.302|25.597|
|255|ASN|O|16.752|46.279|37.550|265|GLU|CD|38.470|40.138|26.723|
|256|LEU|N|17.889|47.805|36.389|265|GLU|OE1|39.623|39.854|27.100|
|256|LEU|CA|17.437|47.297|35.108|265|GLU|OE2|37.835|41.060|27.255|
|256|LEU|CB|17.435|48.386|34.041|265|GLU|C|36.745|38.057|28.227|

FIG.1N

| 265 | GLU | O   | 37.766 | 37.524 | 28.689 | 307 | H2O | OH2 | 26.065 | 37.253 | 43.741 |
| --- | --- | --- | ------ | ------ | ------ | --- | --- | --- | ------ | ------ | ------ |
| 266 | ALA | N   | 36.098 | 39.020 | 28.897 | 308 | H2O | OH2 | 11.945 | 45.684 | 23.380 |
| 266 | ALA | CA  | 36.698 | 39.536 | 30.109 | 309 | H2O | OH2 | 19.643 | 10.507 | 40.112 |
| 266 | ALA | CB  | 35.959 | 40.800 | 30.534 | 310 | H2O | OH2 | 38.430 | 41.954 | 36.077 |
| 266 | ALA | C   | 36.677 | 38.485 | 31.228 | 311 | H2O | OH2 | 13.501 | 39.873 | 16.866 |
| 266 | ALA | O   | 37.562 | 38.418 | 32.099 | 312 | H2O | OH2 | 16.785 | 49.578 | 21.745 |
| 267 | ALA | N   | 35.677 | 37.593 | 31.161 | 313 | H2O | OH2 | 28.911 | 19.876 | 22.976 |
| 267 | ALA | CA  | 35.566 | 36.560 | 32.179 | 314 | H2O | OH2 | 29.797 | 51.940 | 35.038 |
| 267 | ALA | CB  | 34.165 | 35.963 | 32.078 | 315 | H2O | OH2 | 8.968  | 16.983 | 43.770 |
| 267 | ALA | C   | 36.616 | 35.454 | 32.087 | 316 | H2O | OH2 | 21.830 | 26.021 | 49.724 |
| 267 | ALA | O   | 36.811 | 34.737 | 33.081 | 317 | H2O | OH2 | 18.231 | 35.980 | 44.119 |
| 268 | THR | N   | 37.257 | 35.279 | 30.927 | 318 | H2O | OH2 | 17.725 | 35.088 | 15.203 |
| 268 | THR | CA  | 38.227 | 34.187 | 30.751 | 319 | H2O | OH2 | 34.481 | 23.007 | 20.146 |
| 268 | THR | CB  | 37.888 | 33.276 | 29.515 | 320 | H2O | OH2 | 19.764 | 37.086 | 46.005 |
| 268 | THR | OG1 | 37.799 | 34.092 | 28.362 | 321 | H2O | OH2 | 13.211 | 26.583 | 10.242 |
| 268 | THR | CG2 | 36.575 | 32.530 | 29.710 | 322 | H2O | OH2 | 10.729 | 31.502 | 26.207 |
| 268 | THR | C   | 39.617 | 34.741 | 30.576 | 323 | H2O | OH2 | 22.023 | 36.663 | 14.105 |
| 268 | THR | O   | 40.534 | 33.996 | 30.218 | 324 | H2O | OH2 | 26.324 | 19.922 | 21.851 |
| 269 | THR | N   | 39.728 | 36.045 | 30.801 | 325 | H2O | OH2 | 30.661 | 17.697 | 22.182 |
| 269 | ARG | CA  | 41.008 | 36.690 | 30.810 | 326 | H2O | OH2 | 8.433  | 17.883 | 24.882 |
| 269 | ARG | CB  | 40.656 | 38.156 | 30.839 | 327 | H2O | OH2 | 32.021 | 21.783 | 19.092 |
| 269 | ARG | CG  | 41.824 | 39.000 | 30.472 | 328 | H2O | OH2 | 32.606 | 20.038 | 14.623 |
| 269 | ARG | CD  | 41.544 | 40.401 | 29.949 | 329 | H2O | OH2 | 27.918 | 17.370 | 24.830 |
| 269 | ARG | NE  | 42.811 | 40.930 | 29.432 | 330 | H2O | OH2 | 17.445 | 14.094 | 24.149 |
| 269 | ARG | CZ  | 43.324 | 42.136 | 29.787 | 331 | H2O | OH2 | 16.527 | 18.554 | 15.250 |
| 269 | ARG | NH1 | 44.518 | 43.533 | 29.265 | 332 | H2O | OH2 | 15.380 | 14.546 | 15.873 |
| 269 | ARG | NH2 | 42.681 | 42.951 | 30.667 | 333 | H2O | OH2 | 12.129 | 16.040 | 17.903 |
| 269 | ARG | C   | 41.844 | 36.161 | 32.014 | 334 | H2O | OH2 | 13.873 | 16.685 | 15.209 |
| 269 | ARG | OT1 | 41.328 | 35.597 | 32.990 | 335 | H2O | OH2 | 6.048  | 18.751 | 34.243 |
| 269 | ARG | OT2 | 43.070 | 36.206 | 31.952 | 336 | H2O | OH2 | 4.411  | 16.951 | 35.536 |
| 270 | CM  | CM  | 27.629 | 24.423 | 14.043 | 337 | H2O | OH2 | 6.528  | 15.046 | 39.508 |
| 271 | CM  | CM  | 18.482 | 35.001 | 42.551 | 338 | H2O | OH2 | 4.188  | 15.102 | 37.754 |
| 272 | H2O | OH2 | 35.625 | 16.277 | 36.682 | 339 | H2O | OH2 | 7.267  | 13.144 | 37.517 |
| 273 | H2O | OH2 | 19.773 | 36.339 | 42.049 | 340 | H2O | OH2 | 7.231  | 10.169 | 35.676 |
| 274 | H2O | OH2 | 28.438 | 25.352 | 47.303 | 341 | H2O | OH2 | 9.229  | 11.210 | 38.524 |
| 275 | H2O | OH2 | 25.023 | 30.639 | 43.381 | 342 | H2O | OH2 | 13.492 | 9.745  | 35.358 |
| 276 | H2O | OH2 | 23.352 | 28.163 | 42.310 | 343 | H2O | OH2 | 12.026 | 44.524 | 42.622 |
| 277 | H2O | OH2 | 21.594 | 35.893 | 18.729 | 344 | H2O | OH2 | 11.004 | 41.120 | 45.663 |
| 278 | H2O | OH2 | 22.058 | 31.111 | 19.688 | 345 | H2O | OH2 | 10.220 | 39.693 | 42.722 |
| 279 | H2O | OH2 | 18.752 | 45.063 | 40.645 | 346 | H2O | OH2 | 12.059 | 47.753 | 40.959 |
| 280 | H2O | OH2 | 18.039 | 30.216 | 23.124 | 347 | H2O | OH2 | 9.164  | 48.300 | 42.769 |
| 281 | H2O | OH2 | 14.078 | 9.380  | 32.356 | 348 | H2O | OH2 | 11.958 | 43.338 | 44.851 |
| 282 | H2O | OH2 | 15.449 | 19.938 | 28.355 | 349 | H2O | OH2 | 11.239 | 46.641 | 44.371 |
| 283 | H2O | OH2 | 15.927 | 25.605 | 30.476 | 350 | H2O | OH2 | 4.931  | 44.533 | 41.923 |
| 284 | H2O | OH2 | 12.858 | 32.346 | 37.185 | 351 | H2O | OH2 | 6.403  | 36.291 | 34.865 |
| 285 | H2O | OH2 | 11.544 | 33.624 | 27.713 | 352 | H2O | OH2 | 5.564  | 39.764 | 36.611 |
| 286 | H2O | OH2 | 11.580 | 8.103  | 31.642 | 353 | H2O | OH2 | 8.066  | 29.304 | 32.467 |
| 287 | H2O | OH2 | 42.076 | 35.854 | 14.697 | 401 | H2O | OH2 | 23.985 | 29.300 | 19.050 |
| 288 | H2O | OH2 | 8.591  | 11.660 | 25.062 | 402 | H2O | OH2 | 22.840 | 42.988 | 23.949 |
| 289 | H2O | OH2 | 34.301 | 29.140 | 15.200 | 403 | H2O | OH2 | 24.648 | 47.653 | 34.651 |
| 290 | H2O | OH2 | 30.440 | 24.492 | 43.369 | 404 | H2O | OH2 | 22.155 | 15.174 | 18.497 |
| 291 | H2O | OH2 | 35.793 | 42.916 | 26.272 | 405 | H2O | OH2 | 22.394 | 50.724 | 27.973 |
| 292 | H2O | OH2 | 30.881 | 38.720 | 32.534 | 406 | H2O | OH2 | 25.205 | 15.404 | 16.200 |
| 293 | H2O | OH2 | 29.323 | 24.894 | 39.464 | 407 | H2O | OH2 | 16.769 | 30.931 | 11.057 |
| 294 | H2O | OH2 | 30.053 | 41.242 | 26.124 | 408 | H2O | OH2 | 6.421  | 46.954 | 36.986 |
| 295 | H2O | OH2 | 26.029 | 30.946 | 34.554 | 409 | H2O | OH2 | 39.155 | 36.951 | 34.253 |
| 296 | H2O | OH2 | 23.950 | 42.830 | 40.424 | 410 | H2O | OH2 | 30.425 | 43.985 | 26.477 |
| 297 | H2O | OH2 | 22.857 | 33.906 | 20.288 | 411 | H2O | OH2 | 15.991 | 34.160 | 48.706 |
| 298 | H2O | OH2 | 29.750 | 12.657 | 20.465 | 412 | H2O | OH2 | 33.843 | 20.940 | 9.231  |
| 299 | H2O | OH2 | 16.182 | 42.867 | 32.920 | 413 | H2O | OH2 | 16.995 | 50.196 | 28.127 |
| 300 | H2O | OH2 | 20.509 | 35.549 | 16.195 | 415 | H2O | OH2 | 38.899 | 33.531 | 34.689 |
| 301 | H2O | OH2 | 21.065 | 41.688 | 15.225 | 416 | H2O | OH2 | 17.892 | 19.864 | 44.040 |
| 302 | H2O | OH2 | 12.353 | 41.495 | 42.254 | 417 | H2O | OH2 | 34.568 | 30.498 | 17.440 |
| 303 | H2O | OH2 | 11.733 | 34.741 | 14.055 | 419 | H2O | OH2 | 35.622 | 20.284 | 42.959 |
| 304 | H2O | OH2 | 7.156  | 35.456 | 31.880 | 420 | H2O | OH2 | 0.206  | 12.428 | 34.387 |
| 305 | H2O | OH2 | 7.914  | 47.871 | 34.970 | 421 | H2O | OH2 | 38.833 | 23.281 | 24.721 |
| 306 | H2O | OH2 | 5.154  | 42.915 | 39.674 | 422 | H2O | OH2 | 27.524 | 37.611 | 14.941 |

FIG.10

| | | | | | | | | | | |
|---|---|---|---|---|---|---|---|---|---|---|
| 423 | H2O | OH2 | 33.375 | 39.759 | 31.397 | 474 | H2O | OH2 | 33.485 | 27.966 | 24.079 |
| 425 | H2O | OH2 | 10.662 | 51.211 | 37.076 | 475 | H2O | OH2 | 16.400 | 18.715 | 49.507 |
| 426 | H2O | OH2 | 28.400 | 26.227 | 22.233 | 476 | H2O | OH2 | 34.584 | 26.355 | 28.896 |
| 427 | H2O | OH2 | 37.069 | 31.271 | 18.172 | 477 | H2O | OH2 | 18.844 | 26.392 | 36.213 |
| 428 | H2O | OH2 | 35.149 | 22.967 | 42.892 | 478 | H2O | OH2 | 17.595 | 33.022 | 12.700 |
| 429 | H2O | OH2 | 14.410 | 35.423 | 17.549 | 479 | H2O | OH2 | 19.970 | 49.821 | 15.851 |
| 430 | H2O | OH2 | 34.593 | 37.589 | 20.470 | 480 | H2O | OH2 | 29.931 | 22.624 | 47.074 |
| 431 | H2O | OH2 | 33.293 | 43.729 | 30.636 | 481 | H2O | OH2 | 28.764 | 29.952 | 13.997 |
| 432 | H2O | OH2 | 18.935 | 12.276 | 22.731 | 482 | H2O | OH2 | 24.923 | 29.997 | 46.055 |
| 433 | H2O | OH2 | 36.502 | 38.642 | 39.753 | 483 | H2O | OH2 | 4.494 | 34.569 | 48.325 |
| 434 | H2O | OH2 | 30.888 | 44.367 | 36.634 | 484 | H2O | OH2 | 25.927 | 28.389 | 42.632 |
| 435 | H2O | OH2 | 6.433 | 14.502 | 42.412 | 485 | H2O | OH2 | 19.179 | 31.050 | 19.865 |
| 436 | H2O | OH2 | 23.735 | 32.721 | 13.204 | 486 | H2O | OH2 | 33.544 | 35.859 | 34.951 |
| 437 | H2O | OH2 | 30.269 | 39.336 | 42.632 | 489 | H2O | OH2 | 7.275 | 28.059 | 36.209 |
| 438 | H2O | OH2 | 6.916 | 37.376 | 38.041 | 490 | H2O | OH2 | 18.187 | 52.286 | 20.471 |
| 439 | H2O | OH2 | 31.535 | 45.230 | 24.294 | 491 | H2O | OH2 | 14.703 | 47.608 | 24.076 |
| 440 | H2O | OH2 | 21.133 | 38.497 | 43.405 | 492 | H2O | OH2 | 14.414 | 29.083 | 26.931 |
| 441 | H2O | OH2 | 26.156 | 30.548 | 26.735 | 493 | H2O | OH2 | 20.741 | 38.573 | 12.784 |
| 442 | H2O | OH2 | 20.961 | 41.888 | 36.136 | 494 | H2O | OH2 | 32.484 | 22.352 | 42.540 |
| 443 | H2O | OH2 | 10.366 | 9.353 | 42.909 | 495 | H2O | OH2 | 11.669 | 32.823 | 30.485 |
| 444 | H2O | OH2 | 15.664 | 13.252 | 41.086 | 496 | H2O | OH2 | 25.506 | 21.376 | 19.908 |
| 445 | H2O | OH2 | 15.488 | 35.603 | 22.544 | 498 | H2O | OH2 | 14.394 | 49.504 | 27.686 |
| 446 | H2O | OH2 | 8.523 | 29.548 | 42.831 | 499 | H2O | OH2 | 39.498 | 21.926 | 32.920 |
| 448 | H2O | OH2 | 6.347 | 42.537 | 28.354 | 500 | H2O | OH2 | 20.574 | 46.516 | 27.909 |
| 449 | H2O | OH2 | 20.408 | 28.429 | 14.479 | 501 | H2O | OH2 | 41.254 | 36.175 | 22.038 |
| 451 | H2O | OH2 | 9.986 | 37.579 | 24.768 | 502 | H2O | OH2 | 18.615 | 23.589 | 42.251 |
| 452 | H2O | OH2 | 34.820 | 21.034 | 34.828 | 503 | H2O | OH2 | 23.238 | 48.249 | 18.498 |
| 453 | H2O | OH2 | 17.186 | 30.632 | 13.537 | 504 | H2O | OH2 | 11.027 | 27.025 | 49.749 |
| 454 | H2O | OH2 | 12.491 | 19.964 | 46.613 | 505 | H2O | OH2 | 6.051 | 28.870 | 41.533 |
| 455 | H2O | OH2 | 31.523 | 29.927 | 11.890 | 506 | H2O | OH2 | 20.329 | 51.097 | 40.041 |
| 456 | H2O | OH2 | 12.628 | 27.138 | 21.026 | 507 | H2O | OH2 | 34.042 | 46.991 | 33.740 |
| 457 | H2O | OH2 | 33.466 | 44.288 | 34.479 | 508 | H2O | OH2 | 18.800 | 14.484 | 12.899 |
| 458 | H2O | OH2 | 19.599 | 43.860 | 38.560 | 509 | H2O | OH2 | 23.984 | 14.515 | 28.480 |
| 459 | H2O | OH2 | 16.152 | 29.460 | 52.727 | 510 | H2O | OH2 | 14.955 | 20.395 | 22.995 |
| 460 | H2O | OH2 | 12.458 | 29.430 | 17.126 | 511 | H2O | OH2 | 31.742 | 13.971 | 22.917 |
| 461 | H2O | OH2 | 37.639 | 14.784 | 37.217 | 512 | H2O | OH2 | 13.014 | 49.698 | 46.176 |
| 462 | H2O | OH2 | 9.851 | 34.465 | 20.032 | 513 | H2O | OH2 | 3.857 | 17.317 | 43.260 |
| 463 | H2O | OH2 | 33.545 | 17.795 | 26.313 | 514 | H2O | OH2 | 8.348 | 35.692 | 23.895 |
| 464 | H2O | OH2 | 9.256 | 16.911 | 34.260 | 515 | H2O | OH2 | 9.871 | 28.970 | 29.151 |
| 465 | H2O | OH2 | 35.476 | 39.839 | 21.547 | 516 | H2O | OH2 | 18.301 | 41.737 | 20.959 |
| 467 | H2O | OH2 | 23.365 | 24.048 | 13.490 | 517 | H2O | OH2 | 10.419 | 21.355 | 11.387 |
| 468 | H2O | OH2 | 11.732 | 35.837 | 17.577 | 518 | H2O | OH2 | 11.150 | 32.989 | 33.268 |
| 469 | H2O | OH2 | 30.073 | 50.380 | 31.035 | 519 | H2O | OH2 | 43.085 | 38.642 | 27.705 |
| 471 | H2O | OH2 | 16.204 | 22.887 | 7.809 | 520 | H2O | OH2 | 20.416 | 57.764 | 27.758 |
| 472 | H2O | OH2 | 27.601 | 27.623 | 26.352 | 521 | H2O | OH2 | 40.300 | 29.469 | 52.597 |
| 473 | H2O | OH2 | 2.443 | 14.804 | 32.338 | | | | | | |

FIG. 1P

SEQUENCE LISTING (1) GENERAL INFORMATION:

(iii) NUMBER OF SEQUENCES: 104

(2) INFORMATION FOR SEQ ID NO:1:

(i) SEQUENCE CHARACTERISTICS:
      (A) LENGTH: 269 amino acids
      (B) TYPE: amino acid
      (D) TOPOLOGY: unknown (ii) MOLECULE TYPE: protein (iii) HYPOTHETICAL: NO (iv) ANTI-SENSE: NO (vi) ORIGINAL SOURCE:
      (A) ORGANISM: Serine Protease
      (B) STRAIN: Bacillus lentus DSM 5843

(vii) IMMEDIATE SOURCE:
      (B) CLONE: S3T, V4I, A188P, V193M, V199I (xi) SEQUENCE DESCRIPTION: SEQ ID NO:1:

```
Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140
```

```
Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
                180                 185                 190

Met Ala Pro Gly Val Asn Ile Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:2:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S3T, A188P, V193M, V199I (xi) SEQUENCE DESCRIPTION: SEQ ID NO:2:

```
Ala Gln Thr Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Thr Ser Arg Gly
                130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

(2) INFORMATION FOR SEQ ID NO:3:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: V4I, A188P, V193M, V199I (xi) SEQUENCE DESCRIPTION: SEQ ID NO:3:

```
Ala Gln Ser Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
            195                 200                 205
```

```
Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:4:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S139Y, A188P, V193M, V199I (xi) SEQUENCE DESCRIPTION: SEQ ID NO:4:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Tyr Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
            195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240
```

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:5:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S130T, S139Y, A188P, V193M, V199I (xi) SEQUENCE DESCRIPTION: SEQ ID NO:5:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Thr Ala Thr Leu Glu Gln Ala Val Asn Tyr Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
                180                 185                 190

Met Ala Pro Gly Val Asn Ile Gln Ser Thr Tyr Pro Gly Ser Thr Tyr
    195                 200                 205

Ala Ser Leu Asn Gly Thr Ser Met Ala Thr Pro His Val Ala Gly Ala
                210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:6:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: A188P, V193M, V199I (xi) SEQUENCE DESCRIPTION: SEQ ID NO:6:

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:7:

(i) SEQUENCE CHARACTERISTICS:
        (A) LENGTH: 269 amino acids
        (B) TYPE: amino acid (D) TOPOLOGY: unknown (ii) MOLECULE TYPE: protein (iii) HYPOTHETICAL: NO (iv) ANTI-SENSE: NO (vi) ORIGINAL SOURCE:
         (A) ORGANISM: Serine Protease
         (B) STRAIN: Bacillus lentus  DSM 5843

(vii) IMMEDIATE SOURCE:
         (B) CLONE: S3T, A188P, V193M (xi) SEQUENCE DESCRIPTION: SEQ ID NO:7:

Ala Gln Thr Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:8:

(i) SEQUENCE CHARACTERISTICS:
         (A) LENGTH: 269 amino acids
         (B) TYPE: amino acid
         (D) TOPOLOGY: unknown (ii) MOLECULE TYPE: protein (iii) HYPOTHETICAL: NO

```
        (iv) ANTI-SENSE: NO (vi) ORIGINAL SOURCE:
             (A) ORGANISM: Serine Protease
             (B) STRAIN: Bacillus lentus  DSM 5843

(vii) IMMEDIATE SOURCE:
             (B) CLONE: S157T (xi) SEQUENCE DESCRIPTION: SEQ ID NO:8:

Ala Gln Ser Val Pro Trp Gly Ile Ser Arg Val Gln Ala Pro Ala Ala
1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
         35                  40                  45

Phe Val Pro Gly Glu Pro Ser Thr Gln Asp Gly Asn Gly His Gly Thr
     50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
             100                 105                 110

Gly Asn Asn Gly Met His Val Ala Asn Leu Ser Leu Gly Ser Pro Ser
         115                 120                 125

Pro Ser Ala Thr Leu Glu Gln Ala Val Asn Ser Ala Thr Ser Arg Gly
     130                 135                 140

Val Leu Val Val Ala Ala Ser Gly Asn Ser Gly Ala Thr Ser Ile Ser
145                 150                 155                 160

Tyr Pro Ala Arg Tyr Ala Asn Ala Met Ala Val Gly Ala Thr Asp Gln
                 165                 170                 175

Asn Asn Asn Arg Ala Ser Phe Ser Gln Tyr Gly Ala Gly Leu Asp Ile
             180                 185                 190

Val Ala Pro Gly Val Asn Val Gln Ser Thr Tyr Pro Gly Ser Thr Tyr
         195                 200                 205

Ala Ser Leu Asn Gly Thr Ser Met Ala Thr Pro His Val Ala Gly Ala
     210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                 245                 250                 255

Tyr Gly Ser Gly Leu Val Asn Ala Glu Ala Ala Thr Arg
             260                 265

(2) INFORMATION FOR SEQ ID NO:9:

(i) SEQUENCE CHARACTERISTICS:
         (A) LENGTH: 269 amino acids
         (B) TYPE: amino acid
         (D) TOPOLOGY: unknown (ii) MOLECULE TYPE: protein (iii) HYPOTHETICAL: NO (iv) ANTI-SENSE: NO (vi) ORIGINAL SOURCE:
         (A) ORGANISM: Serine Protease
         (B) STRAIN: Bacillus lentus  DSM 5843
```

(vii) IMMEDIATE SOURCE:
    (B) CLONE: A188P, V193M (xi) SEQUENCE DESCRIPTION: SEQ ID NO:9:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65              70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:10:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: A188P (xi) SEQUENCE DESCRIPTION: SEQ ID NO:10:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Pro Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

(2) INFORMATION FOR SEQ ID NO:11:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S3T, V4I, A188P, V193M (xi) SEQUENCE DESCRIPTION: SEQ ID NO:11:

```
Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30
```

```
Thr Gly Ile Ser Thr His Pro Asp Leu Asn Ile Arg Gly Gly Ala Ser
         35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
             100                 105                 110

Gly Asn Asn Gly Met His Val Ala Asn Leu Ser Leu Gly Ser Pro Ser
         115                 120                 125

Pro Ser Ala Thr Leu Glu Gln Ala Val Asn Ser Ala Thr Ser Arg Gly
         130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                 165                 170                 175

Asn Asn Asn Arg Ala Ser Phe Ser Gln Tyr Gly Pro Gly Leu Asp Ile
             180                 185                 190

Met Ala Pro Gly Val Asn Val Gln Ser Thr Tyr Pro Gly Ser Thr Tyr
         195                 200                 205

Ala Ser Leu Asn Gly Thr Ser Met Ala Thr Pro His Val Ala Gly Ala
         210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                 245                 250                 255

Tyr Gly Ser Gly Leu Val Asn Ala Glu Ala Ala Thr Arg
             260                 265

(2) INFORMATION FOR SEQ ID NO:12:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
         (A) ORGANISM: Serine Protease
         (B) STRAIN: Bacillus lentus  DSM 5843

(vii) IMMEDIATE SOURCE:
          (B) CLONE: V193M (xi) SEQUENCE DESCRIPTION: SEQ ID NO:12:

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
         35                  40                  45

Phe Val Pro Gly Glu Pro Ser Thr Gln Asp Gly Asn Gly His Gly Thr
 50                  55                  60
```

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Met Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:13:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S104T (xi) SEQUENCE DESCRIPTION: SEQ ID NO:13:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

```
Asp Gly Arg Gly Ala Ile Ser Thr Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:14:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: T69V (xi) SEQUENCE DESCRIPTION: SEQ ID NO:14:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Val Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125
```

```
Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:15:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: V4I, A188P, V193M (xi) SEQUENCE DESCRIPTION: SEQ ID NO:15:

Ala Gln Ser Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160
```

```
Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Pro Gly Leu Asp Ile
            180                 185                 190

Met Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225             230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

(2) INFORMATION FOR SEQ ID NO:16:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: A224V (xi) SEQUENCE DESCRIPTION: SEQ ID NO:16:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190
```

-continued

```
Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Val
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:17:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: V199I (xi) SEQUENCE DESCRIPTION: SEQ ID NO:17:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
    195                 200                 205

Ala Ser Leu Asn Gly Thr Ser Met Ala Thr Pro His Val Ala Gly Ala
210                 215                 220
```

```
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:18:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: V4I (xi) SEQUENCE DESCRIPTION: SEQ ID NO:18:

```
Ala Gln Ser Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255
```

Tyr Gly Ser Gly Leu Val Asn Ala Glu Ala Ala Thr Arg
            260                 265

(2) INFORMATION FOR SEQ ID NO:19:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S3T (xi) SEQUENCE DESCRIPTION: SEQ ID NO:19:

Ala Gln Thr Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:20:

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine Protease
    (B) STRAIN: Bacillus lentus DSM 5843

(vii) IMMEDIATE SOURCE:
    (B) CLONE: S139Y (xi) SEQUENCE DESCRIPTION: SEQ ID NO:20:

```
Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
        35                  40                  45
Phe Val Pro Gly Glu Pro Ser Thr Gln Asp Gly Asn Gly His Gly Thr
50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Asp Gly Arg Gly Ala Ile Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Tyr Ala Thr Ser Arg Gly
130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265
```

(2) INFORMATION FOR SEQ ID NO:21:

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine Protease
    (B) STRAIN: Bacillus lentus DSM 5843

(vii) IMMEDIATE SOURCE:
    (B) CLONE: N242A (xi) SEQUENCE DESCRIPTION: SEQ ID NO:21:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Ala His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:22:

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:

(A) ORGANISM: Serine Protease
(B) STRAIN: Bacillus lentus DSM 5843

(vii) IMMEDIATE SOURCE:
(B) CLONE: S236T (xi) SEQUENCE DESCRIPTION: SEQ ID NO:22:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Thr Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:23:

(i) SEQUENCE CHARACTERISTICS:
(A) LENGTH: 269 amino acids
(B) TYPE: amino acid
(D) TOPOLOGY: unknown (ii) MOLECULE TYPE: protein (iii) HYPOTHETICAL: NO (iv) ANTI-SENSE: NO (vi) ORIGINAL SOURCE:
(A) ORGANISM: Serine Protease
(B) STRAIN: Bacillus lentus DSM 5843

(vii) IMMEDIATE SOURCE:
(B) CLONE: S36A (xi) SEQUENCE DESCRIPTION: SEQ ID NO:23:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ala Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:24:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: H243A (xi) SEQUENCE DESCRIPTION: SEQ ID NO:24:

Ala Gln Ser Val Pro Trp Gly Ile Ser Arg Val Gln Ala Pro Ala Ala
1               5                   10                  15

-continued

```
His Asn Arg Gly Leu Thr Gly Ser Gly Val Lys Val Ala Val Leu Asp
         20                  25                  30

Thr Gly Ile Ser Thr His Pro Asp Leu Asn Ile Arg Gly Gly Ala Ser
         35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
             115                 120                 125

Pro Ser Ala Thr Leu Glu Gln Ala Val Asn Ser Ala Thr Ser Arg Gly
 130                 135                 140

Val Leu Val Val Ala Ala Ser Gly Asn Ser Gly Ala Ser Ser Ile Ser
 145                 150                 155                 160

Tyr Pro Ala Arg Tyr Ala Asn Ala Met Ala Val Gly Ala Thr Asp Gln
                 165                 170                 175

Asn Asn Asn Arg Ala Ser Phe Ser Gln Tyr Gly Ala Gly Leu Asp Ile
                 180                 185                 190

Val Ala Pro Gly Val Asn Val Gln Ser Thr Tyr Pro Gly Ser Thr Tyr
             195                 200                 205

Ala Ser Leu Asn Gly Thr Ser Met Ala Thr Pro His Val Ala Gly Ala
         210                 215                 220

Ala Ala Leu Val Lys Gln Lys Asn Pro Ser Trp Ser Asn Val Gln Ile
225                 230                 235                 240

Arg Asn Ala Leu Lys Asn Thr Ala Thr Ser Leu Gly Ser Thr Asn Leu
                 245                 250                 255

Tyr Gly Ser Gly Leu Val Asn Ala Glu Ala Ala Thr Arg
                 260                 265
```

(2) INFORMATION FOR SEQ ID NO:25:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: A101T (xi) SEQUENCE DESCRIPTION: SEQ ID NO:25:

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
         35                  40                  45
```

```
Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Thr Ile Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:26:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S236A (xi) SEQUENCE DESCRIPTION: SEQ ID NO:26:

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
                 35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80
```

```
Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ala Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:27:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: E87R (xi) SEQUENCE DESCRIPTION: SEQ ID NO:27:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Arg Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110
```

```
Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:28:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: N114S (xi) SEQUENCE DESCRIPTION: SEQ ID NO:28:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Ser Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140
```

```
Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:29:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: A47W (xi) SEQUENCE DESCRIPTION: SEQ ID NO:29:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Trp Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

(2) INFORMATION FOR SEQ ID NO:30:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: A120S (xi) SEQUENCE DESCRIPTION: SEQ ID NO:30:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
            50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ser Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205
```

```
Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:31:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: T56V (xi) SEQUENCE DESCRIPTION: SEQ ID NO:31:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Val Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
    195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240
```

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:32:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: A120V (xi) SEQUENCE DESCRIPTION: SEQ ID NO:32:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Val Asn Leu Ser Leu Gly Ser Pro Ser
                115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:33:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: G205V (xi) SEQUENCE DESCRIPTION: SEQ ID NO:33:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Val Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:34:

(i) SEQUENCE CHARACTERISTICS:
        (A) LENGTH: 269 amino acids
        (B) TYPE: amino acid (D) TOPOLOGY: unknown (ii) MOLECULE TYPE: protein (iii) HYPOTHETICAL: NO (iv) ANTI-SENSE: NO (vi) ORIGINAL SOURCE:
  (A) ORGANISM: Serine Protease
  (B) STRAIN: Bacillus lentus  DSM 5843

(vii) IMMEDIATE SOURCE:
  (B) CLONE: S130A (xi) SEQUENCE DESCRIPTION: SEQ ID NO:34:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ala Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:35:

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S130T (xi) SEQUENCE DESCRIPTION: SEQ ID NO:35:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Thr Ala Thr Leu Glu Gln Ala Val Asn Ser Ala Thr Ser Arg Gly
                130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
                210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:36:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
    (B) CLONE: A96I (xi) SEQUENCE DESCRIPTION: SEQ ID NO:36:

| Ala | Gln | Ser | Val | Pro | Trp | Gly | Ile | Ser | Arg | Val | Gln | Ala | Pro | Ala | Ala |
|---|---|---|---|---|---|---|---|---|---|---|---|---|---|---|---|
| 1 | | | | 5 | | | | | 10 | | | | | 15 | |

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                      55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ile
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:37:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S104T, S139Y, A224V (xi) SEQUENCE DESCRIPTION: SEQ ID NO:37:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Thr Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Tyr Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Val
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:38:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S139A (xi) SEQUENCE DESCRIPTION: SEQ ID NO:38:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30
```

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ala Ala Thr Ser Arg Gly
 130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
 210                 215                 220

Ala Ala Leu Val Lys Gln Lys Asn Pro Ser Trp Ser Asn Val Gln Ile
 225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265

(2) INFORMATION FOR SEQ ID NO:39:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S142T (xi) SEQUENCE DESCRIPTION: SEQ ID NO:39:

Ala Gln Ser Val Pro Trp Gly Ile Ser Arg Val Gln Ala Pro Ala Ala
 1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
 50                  55                  60

-continued

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Thr Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:40:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S139T (xi) SEQUENCE DESCRIPTION: SEQ ID NO:40:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

```
Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Thr Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:41:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: I102W (xi) SEQUENCE DESCRIPTION: SEQ ID NO:41:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Trp Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125
```

-continued

```
Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:42:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: A96N (xi) SEQUENCE DESCRIPTION: SEQ ID NO:42:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Asn
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160
```

```
Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

(2) INFORMATION FOR SEQ ID NO:43:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: N42F (xi) SEQUENCE DESCRIPTION: SEQ ID NO:43:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Phe Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190
```

```
Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

(2) INFORMATION FOR SEQ ID NO:44:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: S142A (xi) SEQUENCE DESCRIPTION: SEQ ID NO:44:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ala Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220
```

```
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:45:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: H118F (xi) SEQUENCE DESCRIPTION: SEQ ID NO:45:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met Phe Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255
```

Tyr Gly Ser Gly Leu Val Asn Ala Glu Ala Ala Thr Arg
            260                 265

(2) INFORMATION FOR SEQ ID NO:46:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: N237A (xi) SEQUENCE DESCRIPTION: SEQ ID NO:46:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Ala Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:47:

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine Protease
    (B) STRAIN: Bacillus lentus DSM 5843

(vii) IMMEDIATE SOURCE:
    (B) CLONE: N255P (xi) SEQUENCE DESCRIPTION: SEQ ID NO:47:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Pro Leu
                245                 250                 255

Tyr Gly Ser Gly Leu Val Asn Ala Glu Ala Ala Thr Arg
            260                 265
```

(2) INFORMATION FOR SEQ ID NO:48:

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine Protease
    (B) STRAIN: Bacillus lentus DSM 5843

(vii) IMMEDIATE SOURCE:
    (B) CLONE: T141W, N237A (xi) SEQUENCE DESCRIPTION: SEQ ID NO:48:

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Trp Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Ala Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:49:

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:

(A) ORGANISM: Serine Protease
            (B) STRAIN: Bacillus lentus  DSM 5843

(vii) IMMEDIATE SOURCE:
            (B) CLONE: T268V (xi) SEQUENCE DESCRIPTION: SEQ ID NO:49:

Ala Gln Ser Val Pro Trp Gly Ile Ser Arg Val Gln Ala Pro Ala Ala
1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Val Arg
            260                 265

(2) INFORMATION FOR SEQ ID NO:50:

(i) SEQUENCE CHARACTERISTICS:
            (A) LENGTH: 269 amino acids
            (B) TYPE: amino acid
            (D) TOPOLOGY: unknown (ii) MOLECULE TYPE: protein (iii) HYPOTHETICAL: NO (iv) ANTI-SENSE: NO (vi) ORIGINAL SOURCE:
            (A) ORGANISM: Serine Protease
            (B) STRAIN: Bacillus lentus  DSM 5843

(vii) IMMEDIATE SOURCE:
            (B) CLONE: K229W (xi) SEQUENCE DESCRIPTION: SEQ ID NO:50:

| Ala | Gln | Ser | Val | Pro | Trp | Gly | Ile | Ser | Arg | Val | Gln | Ala | Pro | Ala | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Trp Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:51:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: T141W (xi) SEQUENCE DESCRIPTION: SEQ ID NO:51:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
            50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Trp Ser Arg Gly
            130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265

(2) INFORMATION FOR SEQ ID NO:52:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus  DSM 5843

(vii) IMMEDIATE SOURCE:
        (B) CLONE: wildtype (xi) SEQUENCE DESCRIPTION: SEQ ID NO:52:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

```
Phe Val Pro Gly Glu Pro Ser Thr Gln Asp Gly Asn Gly His Gly Thr
 50                  55                  60
His Val Ala Gly Thr Ile Ala Ala Leu Asn Asn Ser Ile Gly Val Leu
 65                  70                  75                  80
Gly Val Ala Pro Ser Ala Glu Leu Tyr Ala Val Lys Val Leu Gly Ala
                 85                  90                  95
Asp Gly Arg Gly Ala Ile Ser Ser Ile Ala Gln Gly Leu Glu Trp Ala
             100                 105                 110
Gly Asn Asn Gly Met His Val Ala Asn Leu Ser Leu Gly Ser Pro Ser
             115                 120                 125
Pro Ser Ala Thr Leu Glu Gln Ala Val Asn Ser Ala Thr Ser Arg Gly
 130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
                180                 185                 190
Val Ala Pro Gly Val Asn Val Gln Ser Thr Tyr Pro Gly Ser Thr Tyr
                195                 200                 205
Ala Ser Leu Asn Gly Thr Ser Met Ala Thr Pro His Val Ala Gly Ala
 210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
                260                 265

(2) INFORMATION FOR SEQ ID NO:53:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S3T, V4I, A188P, V193M, V199I (xi) SEQUENCE DESCRIPTION: SEQ ID NO:53:

GCGCAAACAA TCCCATGGGG AATTAGCCGT GTGCAAGCCC CGGCTGCCCA TAACCGTGGA    60

TTGACAGGTT CTGGTGTAAA AGTTGCTGTC CTCGATACAG GTATTTCCAC TCATCCAGAC   120

TTAAATATTC GTGGTGGCGC TAGCTTTGTA CCAGGGGAAC CATCCACTCA AGATGGGAAT   180

GGGCATGGCA CGCATGTGGC CGGGACGATT GCTGCTTTAA ACAATTCGAT TGGCGTTCTT   240

GGCGTAGCGC CTAGTGCGGA ACTATACGCT GTTAAAGTTT TAGGAGCCGA CGGTAGAGGT   300

GCAATCAGCT CGATTGCCCA AGGGTTGGAA TGGGCAGGGA ACAATGGCAT GCACGTTGCT   360

AATTTGAGTT TAGGAAGCCC TTCGCCAAGT GCCACACTTG AGCAAGCTGT TAATAGCGCG   420

ACTTCTAGAG GCGTTCTTGT TGTAGCGGCA TCTGGGAATT CAGGTGCAAG CTCAATCAGC   480
```

| | |
|---|---|
| TATCCGGCCC GTTATGCGAA CGCAATGGCA GTCGGAGCTA CTGACCAAAA CAACAACCGC | 540 |
| GCCAGCTTTT CACAGTATGG CCCAGGGCTT GACATTATGG CACCAGGGGT AAACATTCAG | 600 |
| AGCACATACC CAGGTTCAAC GTATGCCAGC TTAAACGGTA CATCGATGGC TACTCCTCAT | 660 |
| GTTGCAGGTG CAGCAGCCCT TGTTAAACAA AAGAACCCAT CTTGGTCCAA TGTACAAATC | 720 |
| CGCAACCATC TAAAGAATAC GGCAACGAGC TTAGGAAGCA CGAACTTGTA TGGAAGCGGA | 780 |
| CTTGTCAATG CAGAAGCGGC AACACGC | 807 |

(2) INFORMATION FOR SEQ ID NO:54:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S3T, A188P, V193M, V199I (xi) SEQUENCE DESCRIPTION: SEQ ID NO:54:

| | |
|---|---|
| GCGCAAACAG TGCCATGGGG AATTAGCCGT GTGCAAGCCC CGGCTGCCCA TAACCGTGGA | 60 |
| TTGACAGGTT CTGGTGTAAA AGTTGCTGTC CTCGATACAG GTATTTCCAC TCATCCAGAC | 120 |
| TTAAATATTC GTGGTGGCGC TAGCTTTGTA CCAGGGGAAC CATCCACTCA AGATGGGAAT | 180 |
| GGGCATGGCA CGCATGTGGC CGGGACGATT GCTGCTTTAA ACAATTCGAT TGGCGTTCTT | 240 |
| GGCGTAGCGC CTAGTGCGGA ACTATACGCT GTTAAAGTTT TAGGAGCCGA CGGTAGAGGT | 300 |
| GCAATCAGCT CGATTGCCCA AGGGTTGGAA TGGGCAGGGA ACAATGGCAT GCACGTTGCT | 360 |
| AATTTGAGTT TAGGAAGCCC TTCGCCAAGT GCCACACTTG AGCAAGCTGT TAATAGCGCG | 420 |
| ACTTCTAGAG GCGTTCTTGT TGTAGCGGCA TCTGGGAATT CAGGTGCAAG CTCAATCAGC | 480 |
| TATCCGGCCC GTTATGCGAA CGCAATGGCA GTCGGAGCTA CTGACCAAAA CAACAACCGC | 540 |
| GCCAGCTTTT CACAGTATGG CCCAGGGCTT GACATTATGG CACCAGGGGT AAACATTCAG | 600 |
| AGCACATACC CAGGTTCAAC GTATGCCAGC TTAAACGGTA CATCGATGGC TACTCCTCAT | 660 |
| GTTGCAGGTG CAGCAGCCCT TGTTAAACAA AAGAACCCAT CTTGGTCCAA TGTACAAATC | 720 |
| CGCAACCATC TAAAGAATAC GGCAACGAGC TTAGGAAGCA CGAACTTGTA TGGAAGCGGA | 780 |
| CTTGTCAATG CAGAAGCGGC AACACGC | 807 |

(2) INFORMATION FOR SEQ ID NO:55:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:

(B) STRAIN: Bacillus lentus DSM 5483

(vii) IMMEDIATE SOURCE:
        (B) CLONE: V4I, A188P, V193M, V199I (xi) SEQUENCE DESCRIPTION: SEQ ID NO:55:

GCGCAATCAA TCCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATAGCGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CCCAGGGCTT GACATTATGG CACCAGGGGT AAACATTCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AAGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                       807

(2) INFORMATION FOR SEQ ID NO:56:

(i) SEQUENCE CHARACTERISTICS:
         (A) LENGTH: 807 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (B) STRAIN: Bacillus lentus DSM 5483

(vii) IMMEDIATE SOURCE:
         (B) CLONE: S139Y, A188P, V193M, V199I (xi) SEQUENCE DESCRIPTION: SEQ ID NO:56:

GCGCAATCAG TGCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATTATGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CCCAGGGCTT GACATTATGG CACCAGGGGT AAACATTCAG    600

AGCACATACC CAGGTTCAAC GTATGCCAGC TTAAACGGTA CATCGATGGC TACTCCTCAT    660

| | | |
|---|---|---|
| GTTGCAGGTG CAGCAGCCCT TGTTAAACAA AAGAACCCAT CTTGGTCCAA TGTACAAATC | 720 |
| CGCAACCATC TAAAGAATAC GGCAACGAGC TTAGGAAGCA CGAACTTGTA TGGAAGCGGA | 780 |
| CTTGTCAATG CAGAAGCGGC AACACGC | 807 |

(2) INFORMATION FOR SEQ ID NO:57:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S130T, S139Y, A188P, V193M, V199I (xi) SEQUENCE DESCRIPTION: SEQ ID NO:57:

| | | |
|---|---|---|
| GCGCAATCAG TGCCATGGGG AATTAGCCGT GTGCAAGCCC CGGCTGCCCA TAACCGTGGA | 60 |
| TTGACAGGTT CTGGTGTAAA AGTTGCTGTC CTCGATACAG GTATTTCCAC TCATCCAGAC | 120 |
| TTAAATATTC GTGGTGGCGC TAGCTTTGTA CCAGGGGAAC CATCCACTCA AGATGGGAAT | 180 |
| GGGCATGGCA CGCATGTGGC CGGGACGATT GCTGCTTTAA ACAATTCGAT TGGCGTTCTT | 240 |
| GGCGTAGCGC CTAGTGCGGA ACTATACGCT GTTAAAGTTT TAGGAGCCGA CGGTAGAGGT | 300 |
| GCAATCAGCT CGATTGCCCA AGGGTTGGAA TGGGCAGGGA ACAATGGCAT GCACGTTGCT | 360 |
| AATTTGAGTT TAGGAAGCCC TTCGCCAACA GCCACACTTG AGCAAGCTGT TAATTATGCG | 420 |
| ACTTCTAGAG GCGTTCTTGT TGTAGCGGCA TCTGGGAATT CAGGTGCAAG CTCAATCAGC | 480 |
| TATCCGGCCC GTTATGCGAA CGCAATGGCA GTCGGAGCTA CTGACCAAAA CAACAACCGC | 540 |
| GCCAGCTTTT CACAGTATGG CCCAGGGCTT GACATTATGG CACCAGGGGT AAACATTCAG | 600 |
| AGCACATACC CAGGTTCAAC GTATGCCAGC TTAAACGGTA CATCGATGGC TACTCCTCAT | 660 |
| GTTGCAGGTG CAGCAGCCCT TGTTAAACAA AAGAACCCAT CTTGGTCCAA TGTACAAATC | 720 |
| CGCAACCATC TAAAGAATAC GGCAACGAGC TTAGGAAGCA CGAACTTGTA TGGAAGCGGA | 780 |
| CTTGTCAATG CAGAAGCGGC AACACGC | 807 |

(2) INFORMATION FOR SEQ ID NO:58:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: A188P, V193M, V199I (xi) SEQUENCE DESCRIPTION: SEQ ID NO:58:

```
GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CCCAGGGCTT GACATTATGG CACCAGGGGT AAACATTCAG     600

AGCACATACC CAGGTTCAAC GTATGCCAGC TTAAACGGTA CATCGATGGC TACTCCTCAT     660

GTTGCAGGTG CAGCAGCCCT TGTTAAACAA AAGAACCCAT CTTGGTCCAA TGTACAAATC     720

CGCAACCATC TAAAGAATAC GGCAACGAGC TTAGGAAGCA CGAACTTGTA TGGAAGCGGA     780

CTTGTCAATG CAGAAGCGGC AACACGC                                        807
```

(2) INFORMATION FOR SEQ ID NO:59:

(i) SEQUENCE CHARACTERISTICS:
    (A) LENGTH: 807 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (B) STRAIN: Bacillus lentus DSM 5483

(vii) IMMEDIATE SOURCE:
    (B) CLONE: S3T, A188P, V193M (xi) SEQUENCE DESCRIPTION: SEQ ID NO:59:

```
GCGCAAACAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CCCAGGGCTT GACATTATGG CACCAGGGGT AAACGTGCAG     600

AGCACATACC CAGGTTCAAC GTATGCCAGC TTAAACGGTA CATCGATGGC TACTCCTCAT     660

GTTGCAGGTG CAGCAGCCCT TGTTAAACAA AAGAACCCAT CTTGGTCCAA TGTACAAATC     720

CGCAACCATC TAAAGAATAC GGCAACGAGC TTAGGAAGCA CGAACTTGTA TGGAAGCGGA     780

CTTGTCAATG CAGAAGCGGC AACACGC                                        807
```

(2) INFORMATION FOR SEQ ID NO:60:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S157T (xi) SEQUENCE DESCRIPTION: SEQ ID NO:60:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAC ATCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AGAACCCAT CTTGGTCCAA TGTACAAATC      720
CGCAACCATC TAAAGAATAC GGCAACGAGC TTAGGAAGCA CGAACTTGTA TGGAAGCGGA     780
CTTGTCAATG CAGAAGCGGC AACACGC                                        807
```

(2) INFORMATION FOR SEQ ID NO:61:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: A188P, V193M (xi) SEQUENCE DESCRIPTION: SEQ ID NO:61:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
```

137

-continued

```
GGCGTAGCGC CTAGTGCGGA ACTATACGCT GTTAAAGTTT TAGGAGCCGA CGGTAGAGGT        300

GCAATCAGCT CGATTGCCCA AGGGTTGGAA TGGGCAGGGA ACAATGGCAT GCACGTTGCT        360

AATTTGAGTT TAGGAAGCCC TTCGCCAAGT GCCACACTTG AGCAAGCTGT TAATAGCGCG        420

ACTTCTAGAG GCGTTCTTGT TGTAGCGGCA TCTGGGAATT CAGGTGCAAG CTCAATCAGC        480

TATCCGGCCC GTTATGCGAA CGCAATGGCA GTCGGAGCTA CTGACCAAAA CAACAACCGC        540

GCCAGCTTTT CACAGTATGG CCCAGGGCTT GACATTATGG CACCAGGGGT AAACGTGCAG        600

AGCACATACC CAGGTTCAAC GTATGCCAGC TTAAACGGTA CATCGATGGC TACTCCTCAT        660

GTTGCAGGTG CAGCAGCCCT TGTTAAACAA AAGAACCCAT CTTGGTCCAA TGTACAAATC        720

CGCAACCATC TAAAGAATAC GGCAACGAGC TTAGGAAGCA CGAACTTGTA TGGAAGCGGA        780

CTTGTCAATG CAGAAGCGGC AACACGC                                            807
```

(2) INFORMATION FOR SEQ ID NO:62:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: A188P (xi) SEQUENCE DESCRIPTION: SEQ ID NO:62:

```
GCGCAATCAG TGCCATGGGG AATTAGCCGT GTGCAAGCCC CGGCTGCCCA TAACCGTGGA         60

TTGACAGGTT CTGGTGTAAA AGTTGCTGTC CTCGATACAG GTATTTCCAC TCATCCAGAC        120

TTAAATATTC GTGGTGGCGC TAGCTTTGTA CCAGGGGAAC CATCCACTCA AGATGGGAAT        180

GGGCATGGCA CGCATGTGGC CGGGACGATT GCTGCTTTAA ACAATTCGAT TGGCGTTCTT        240

GGCGTAGCGC CTAGTGCGGA ACTATACGCT GTTAAAGTTT TAGGAGCCGA CGGTAGAGGT        300

GCAATCAGCT CGATTGCCCA AGGGTTGGAA TGGGCAGGGA ACAATGGCAT GCACGTTGCT        360

AATTTGAGTT TAGGAAGCCC TTCGCCAAGT GCCACACTTG AGCAAGCTGT TAATAGCGCG        420

ACTTCTAGAG GCGTTCTTGT TGTAGCGGCA TCTGGGAATT CAGGTGCAAG CTCAATCAGC        480

TATCCGGCCC GTTATGCGAA CGCAATGGCA GTCGGAGCTA CTGACCAAAA CAACAACCGC        540

GCCAGCTTTT CACAGTATGG CCCAGGGCTT GACATTGTCG CACCAGGGGT AAACGTGCAG        600

AGCACATACC CAGGTTCAAC GTATGCCAGC TTAAACGGTA CATCGATGGC TACTCCTCAT        660

GTTGCAGGTG CAGCAGCCCT TGTTAAACAA AAGAACCCAT CTTGGTCCAA TGTACAAATC        720

CGCAACCATC TAAAGAATAC GGCAACGAGC TTAGGAAGCA CGAACTTGTA TGGAAGCGGA        780

CTTGTCAATG CAGAAGCGGC AACACGC                                            807
```

(2) INFORMATION FOR SEQ ID NO:63:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (B) STRAIN: Bacillus lentus DSM 5483

(vii) IMMEDIATE SOURCE:
    (B) CLONE: S3T, V4I, A188P, V193M (xi) SEQUENCE DESCRIPTION: SEQ ID NO:63:

```
GCGCAAACAA TCCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CCCAGGGCTT GACATTATGG CACCAGGGGT AAACGTGCAG     600

AGCACATACC CAGGTTCAAC GTATGCCAGC TTAAACGGTA CATCGATGGC TACTCCTCAT     660

GTTGCAGGTG CAGCAGCCCT TGTTAAACAA AAGAACCCAT CTTGGTCCAA TGTACAAATC     720

CGCAACCATC TAAAGAATAC GGCAACGAGC TTAGGAAGCA CGAACTTGTA TGGAAGCGGA     780

CTTGTCAATG CAGAAGCGGC AACACGC                                         807
```

(2) INFORMATION FOR SEQ ID NO:64:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: V193M (xi) SEQUENCE DESCRIPTION: SEQ ID NO:64:

```
GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420
```

```
ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTATGG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACCATC TAAAGAATAC GGCAACGAGC TTAGGAAGCA CGAACTTGTA TGGAAGCGGA      780

CTTGTCAATG CAGAAGCGGC AACACGC                                          807
```

(2) INFORMATION FOR SEQ ID NO:65:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S104T (xi) SEQUENCE DESCRIPTION: SEQ ID NO:65:

```
GCGCAATCAG TGCCATGGGG AATTAGCCGT GTGCAAGCCC CGGCTGCCCA TAACCGTGGA       60

TTGACAGGTT CTGGTGTAAA AGTTGCTGTC CTCGATACAG GTATTTCCAC TCATCCAGAC      120

TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA CAATTCGAT TGGCGTTCTT       240

GGCGTAGCGC CTAGTGCGGA ACTATACGCT GTTAAAGTTT TAGGAGCCGA CGGTAGAGGT      300

GCAATCAGCA CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACCATC TAAAGAATAC GGCAACGAGC TTAGGAAGCA CGAACTTGTA TGGAAGCGGA      780

CTTGTCAATG CAGAAGCGGC AACACGC                                          807
```

(2) INFORMATION FOR SEQ ID NO:66:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO

143

-continued (vi) ORIGINAL SOURCE:
    (B) STRAIN: Bacillus lentus DSM 5483

(vii) IMMEDIATE SOURCE:
    (B) CLONE: T69V (xi) SEQUENCE DESCRIPTION: SEQ ID NO:66:

```
GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGGTTATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CGCAGGGCTT GACATTGTCG CACCAGGGGT AAACGTGCAG     600

AGCACATACC CAGGTTCAAC GTATGCCAGC TTAAACGGTA CATCGATGGC TACTCCTCAT     660

GTTGCAGGTG CAGCAGCCCT TGTTAAACAA AAGAACCCAT CTTGGTCCAA TGTACAAATC     720

CGCAACCATC TAAAGAATAC GGCAACGAGC TTAGGAAGCA CGAACTTGTA TGGAAGCGGA     780

CTTGTCAATG CAGAAGCGGC AACACGC                                        807
```

(2) INFORMATION FOR SEQ ID NO:67:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: V4I, A188P, V193M (xi) SEQUENCE DESCRIPTION: SEQ ID NO:67:

```
GCGCAATCAA TCCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CCCAGGGCTT GACATTATGG CACCAGGGGT AAACGTGCAG     600

AGCACATACC CAGGTTCAAC GTATGCCAGC TTAAACGGTA CATCGATGGC TACTCCTCAT     660
```

```
GTTGCAGGTG CAGCAGCCCT TGTTAAACAA AGAACCCAT CTTGGTCCAA TGTACAAATC       720

CGCAACCATC TAAAGAATAC GGCAACGAGC TTAGGAAGCA CGAACTTGTA TGGAAGCGGA      780

CTTGTCAATG CAGAAGCGGC AACACGC                                         807
```

(2) INFORMATION FOR SEQ ID NO:68:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: A224V (xi) SEQUENCE DESCRIPTION: SEQ ID NO:68:

```
GCGCAATCAG TGCCATGGGG AATTAGCCGT GTGCAAGCCC CGGCTGCCCA TAACCGTGGA       60

TTGACAGGTT CTGGTGTAAA AGTTGCTGTC CTCGATACAG GTATTTCCAC TCATCCAGAC      120

TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT TAGGAGCCGA CGGTAGAGGT      300

GCAATCAGCT CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG TTGCAGCCCT TGTTAAACAA AGAACCCAT CTTGGTCCAA TGTACAAATC       720

CGCAACCATC TAAAGAATAC GGCAACGAGC TTAGGAAGCA CGAACTTGTA TGGAAGCGGA      780

CTTGTCAATG CAGAAGCGGC AACACGC                                         807
```

(2) INFORMATION FOR SEQ ID NO:69:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: V199I (xi) SEQUENCE DESCRIPTION: SEQ ID NO:69:

```
GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CGCAGGGCTT GACATTGTCG CACCAGGGGT AAACATTCAG     600

AGCACATACC CAGGTTCAAC GTATGCCAGC TTAAACGGTA CATCGATGGC TACTCCTCAT     660

GTTGCAGGTG CAGCAGCCCT TGTTAAACAA AGAACCCAT CTTGGTCCAA TGTACAAATC      720

CGCAACCATC TAAAGAATAC GGCAACGAGC TTAGGAAGCA CGAACTTGTA TGGAAGCGGA     780

CTTGTCAATG CAGAAGCGGC AACACGC                                         807
```

(2) INFORMATION FOR SEQ ID NO:70:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: V4I (xi) SEQUENCE DESCRIPTION: SEQ ID NO:70:

```
GCGCAATCAA TCCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CGCAGGGCTT GACATTGTCG CACCAGGGGT AAACGTGCAG     600

AGCACATACC CAGGTTCAAC GTATGCCAGC TTAAACGGTA CATCGATGGC TACTCCTCAT     660

GTTGCAGGTG CAGCAGCCCT TGTTAAACAA AGAACCCAT CTTGGTCCAA TGTACAAATC      720

CGCAACCATC TAAAGAATAC GGCAACGAGC TTAGGAAGCA CGAACTTGTA TGGAAGCGGA     780

CTTGTCAATG CAGAAGCGGC AACACGC                                         807
```

(2) INFORMATION FOR SEQ ID NO:71:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S3T (xi) SEQUENCE DESCRIPTION: SEQ ID NO:71:

```
GCGCAAACAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                         807
```

(2) INFORMATION FOR SEQ ID NO:72:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S139Y (xi) SEQUENCE DESCRIPTION: SEQ ID NO:72:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
```

```
GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT TAGGAGCCGA CGGTAGAGGT      300

GCAATCAGCT CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATTATGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACCATC TAAAGAATAC GGCAACGAGC TTAGGAAGCA CGAACTTGTA TGGAAGCGGA      780

CTTGTCAATG CAGAAGCGGC AACACGC                                         807
```

(2) INFORMATION FOR SEQ ID NO:73:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: N242A (xi) SEQUENCE DESCRIPTION: SEQ ID NO:73:

```
GCGCAATCAG TGCCATGGGG AATTAGCCGT GTGCAAGCCC CGGCTGCCCA TAACCGTGGA       60

TTGACAGGTT CTGGTGTAAA AGTTGCTGTC CTCGATACAG GTATTTCCAC TCATCCAGAC      120

TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT TAGGAGCCGA CGGTAGAGGT      300

GCAATCAGCT CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCGCACATC TAAAGAATAC GGCAACGAGC TTAGGAAGCA CGAACTTGTA TGGAAGCGGA      780

CTTGTCAATG CAGAAGCGGC AACACGC                                         807
```

(2) INFORMATION FOR SEQ ID NO:74:

(i) SEQUENCE CHARACTERISTICS:
        (A) LENGTH: 807 base pairs
        (B) TYPE: nucleic acid
        (C) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (B) STRAIN: Bacillus lentus DSM 5483

(vii) IMMEDIATE SOURCE:
          (B) CLONE: S236T (xi) SEQUENCE DESCRIPTION: SEQ ID NO:74:

GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATAGCGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CGCAGGGCTT GACATTGTCG CACCAGGGGT AAACGTGCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AAGAACCCAT CTTGGACAAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                       807

(2) INFORMATION FOR SEQ ID NO:75:

(i) SEQUENCE CHARACTERISTICS:
          (A) LENGTH: 807 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (B) STRAIN: Bacillus lentus DSM 5483

(vii) IMMEDIATE SOURCE:
          (B) CLONE: S36A (xi) SEQUENCE DESCRIPTION: SEQ ID NO:75:

GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTGCAAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATAGCGCG    420

```
ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACCATC TAAAGAATAC GGCAACGAGC TTAGGAAGCA CGAACTTGTA TGGAAGCGGA      780

CTTGTCAATG CAGAAGCGGC AACACGC                                         807
```

(2) INFORMATION FOR SEQ ID NO:76:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: H243A (xi) SEQUENCE DESCRIPTION: SEQ ID NO:76:

```
GCGCAATCAG TGCCATGGGG AATTAGCCGT GTGCAAGCCC CGGCTGCCCA TAACCGTGGA       60

TTGACAGGTT CTGGTGTAAA AGTTGCTGTC CTCGATACAG GTATTTCCAC TCATCCAGAC      120

TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT TAGGAGCCGA CGGTAGAGGT      300

GCAATCAGCT CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACGCAC TAAAGAATAC GGCAACGAGC TTAGGAAGCA CGAACTTGTA TGGAAGCGGA      780

CTTGTCAATG CAGAAGCGGC AACACGC                                         807
```

(2) INFORMATION FOR SEQ ID NO:77:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (B) STRAIN: Bacillus lentus DSM 5483

(vii) IMMEDIATE SOURCE:
              (B) CLONE: A101T (xi) SEQUENCE DESCRIPTION: SEQ ID NO:77:

GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

ACAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CGCAGGGCTT GACATTGTCG CACCAGGGGT AAACGTGCAG     600

AGCACATACC CAGGTTCAAC GTATGCCAGC TTAAACGGTA CATCGATGGC TACTCCTCAT     660

GTTGCAGGTG CAGCAGCCCT TGTTAAACAA AAGAACCCAT CTTGGTCCAA TGTACAAATC     720

CGCAACCATC TAAAGAATAC GGCAACGAGC TTAGGAAGCA CGAACTTGTA TGGAAGCGGA     780

CTTGTCAATG CAGAAGCGGC AACACGC                                        807

(2) INFORMATION FOR SEQ ID NO:78:

(i) SEQUENCE CHARACTERISTICS:
              (A) LENGTH: 807 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (B) STRAIN: Bacillus lentus DSM 5483

(vii) IMMEDIATE SOURCE:
              (B) CLONE: S236A (xi) SEQUENCE DESCRIPTION: SEQ ID NO:78:

GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CGCAGGGCTT GACATTGTCG CACCAGGGGT AAACGTGCAG     600

5,985,639

159                                                                                                           160

-continued

```
AGCACATACC CAGGTTCAAC GTATGCCAGC TTAAACGGTA CATCGATGGC TACTCCTCAT    660

GTTGCAGGTG CAGCAGCCCT TGTTAAACAA AGAACCCAT CTTGGGCAAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                        807
```

(2) INFORMATION FOR SEQ ID NO:79:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: E87R (xi) SEQUENCE DESCRIPTION: SEQ ID NO:79:

```
GCGCAATCAG TGCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGCG TCTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATAGCGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CGCAGGGCTT GACATTGTCG CACCAGGGGT AAACGTGCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                        807
```

(2) INFORMATION FOR SEQ ID NO:80:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: N114S (xi) SEQUENCE DESCRIPTION: SEQ ID NO:80:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA GCAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                        807
```

(2) INFORMATION FOR SEQ ID NO:81:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: A47W (xi) SEQUENCE DESCRIPTION: SEQ ID NO:81:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCTG GAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                        807
```

(2) INFORMATION FOR SEQ ID NO:82:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: A120S (xi) SEQUENCE DESCRIPTION: SEQ ID NO:82:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTAGC     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                        807
```

(2) INFORMATION FOR SEQ ID NO:83:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: T56V (xi) SEQUENCE DESCRIPTION: SEQ ID NO:83:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCGTTCA AGATGGGAAT     180
```

```
GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATAGCGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CGCAGGGCTT GACATTGTCG CACCAGGGGT AAACGTGCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AAGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                       807
```

(2) INFORMATION FOR SEQ ID NO:84:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: A120V (xi) SEQUENCE DESCRIPTION: SEQ ID NO:84:

```
GCGCAATCAG TGCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGTT    360

AATTTGAGTT TAGGAAGCCC TTCGCCAAGT GCCACACTTG AGCAAGCTGT TAATAGCGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CGCAGGGCTT GACATTGTCG CACCAGGGGT AAACGTGCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AAGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                       807
```

(2) INFORMATION FOR SEQ ID NO:85:

(i) SEQUENCE CHARACTERISTICS:
        (A) LENGTH: 807 base pairs
        (B) TYPE: nucleic acid (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (B) STRAIN: Bacillus lentus DSM 5483

(vii) IMMEDIATE SOURCE:
            (B) CLONE: G205V (xi) SEQUENCE DESCRIPTION: SEQ ID NO:85:

GCGCAATCAG TGCCATGGGG AATTAGCCGT GTGCAAGCCC CGGCTGCCCA TAACCGTGGA    60

TTGACAGGTT CTGGTGTAAA AGTTGCTGTC CTCGATACAG GTATTTCCAC TCATCCAGAC   120

TTAAATATTC GTGGTGGCGC TAGCTTTGTA CCAGGGGAAC CATCCACTCA AGATGGGAAT   180

GGGCATGGCA CGCATGTGGC CGGGACGATT GCTGCTTTAA ACAATTCGAT TGGCGTTCTT   240

GGCGTAGCGC CTAGTGCGGA ACTATACGCT GTTAAAGTTT TAGGAGCCGA CGGTAGAGGT   300

GCAATCAGCT CGATTGCCCA AGGGTTGGAA TGGGCAGGGA ACAATGGCAT GCACGTTGCT   360

AATTTGAGTT TAGGAAGCCC TTCGCCAAGT GCCACACTTG AGCAAGCTGT TAATAGCGCG   420

ACTTCTAGAG GCGTTCTTGT TGTAGCGGCA TCTGGGAATT CAGGTGCAAG CTCAATCAGC   480

TATCCGGCCC GTTATGCGAA CGCAATGGCA GTCGGAGCTA CTGACCAAAA CAACAACCGC   540

GCCAGCTTTT CACAGTATGG CGCAGGGCTT GACATTGTCG CACCAGGGGT AAACGTGCAG   600

AGCACATACC CAGTTTCAAC GTATGCCAGC TTAAACGGTA CATCGATGGC TACTCCTCAT   660

GTTGCAGGTG CAGCAGCCCT TGTTAAACAA AAGAACCCAT CTTGGTCCAA TGTACAAATC   720

CGCAACCATC TAAAGAATAC GGCAACGAGC TTAGGAAGCA CGAACTTGTA TGGAAGCGGA   780

CTTGTCAATG CAGAAGCGGC AACACGC                                     807

(2) INFORMATION FOR SEQ ID NO:86:

(i) SEQUENCE CHARACTERISTICS:
            (A) LENGTH: 807 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (B) STRAIN: Bacillus lentus DSM 5483

(vii) IMMEDIATE SOURCE:
            (B) CLONE: S130A (xi) SEQUENCE DESCRIPTION: SEQ ID NO:86:

GCGCAATCAG TGCCATGGGG AATTAGCCGT GTGCAAGCCC CGGCTGCCCA TAACCGTGGA    60

TTGACAGGTT CTGGTGTAAA AGTTGCTGTC CTCGATACAG GTATTTCCAC TCATCCAGAC   120

TTAAATATTC GTGGTGGCGC TAGCTTTGTA CCAGGGGAAC CATCCACTCA AGATGGGAAT   180

GGGCATGGCA CGCATGTGGC CGGGACGATT GCTGCTTTAA ACAATTCGAT TGGCGTTCTT   240

GGCGTAGCGC CTAGTGCGGA ACTATACGCT GTTAAAGTTT TAGGAGCCGA CGGTAGAGGT   300

GCAATCAGCT CGATTGCCCA AGGGTTGGAA TGGGCAGGGA ACAATGGCAT GCACGTTGCT   360

```
AATTTGAGTT TAGGAAGCCC TTCGCCAGCA GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACCATC TAAAGAATAC GGCAACGAGC TTAGGAAGCA CGAACTTGTA TGGAAGCGGA      780

CTTGTCAATG CAGAAGCGGC AACACGC                                          807
```

(2) INFORMATION FOR SEQ ID NO:87:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S130T (xi) SEQUENCE DESCRIPTION: SEQ ID NO:87:

```
GCGCAATCAG TGCCATGGGG AATTAGCCGT GTGCAAGCCC CGGCTGCCCA TAACCGTGGA       60

TTGACAGGTT CTGGTGTAAA AGTTGCTGTC CTCGATACAG GTATTTCCAC TCATCCAGAC      120

TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT TAGGAGCCGA CGGTAGAGGT      300

GCAATCAGCT CGATTGCCCA AGGGTTGGAA TGGGCAGGGA ACAATGGCAT GCACGTTGCT      360

AATTTGAGTT TAGGAAGCCC TTCGCCAACA GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACCATC TAAAGAATAC GGCAACGAGC TTAGGAAGCA CGAACTTGTA TGGAAGCGGA      780

CTTGTCAATG CAGAAGCGGC AACACGC                                          807
```

(2) INFORMATION FOR SEQ ID NO:88:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (B) STRAIN: Bacillus lentus DSM 5483

(vii) IMMEDIATE SOURCE:
    (B) CLONE: A96I (xi) SEQUENCE DESCRIPTION: SEQ ID NO:88:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAATTGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                         807
```

(2) INFORMATION FOR SEQ ID NO:89:

(i) SEQUENCE CHARACTERISTICS:
    (A) LENGTH: 807 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (B) STRAIN: Bacillus lentus DSM 5483

(vii) IMMEDIATE SOURCE:
    (B) CLONE: S104T, S139Y, A224V (xi) SEQUENCE DESCRIPTION: SEQ ID NO:89:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCA CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATTATGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
```

```
AGCACATACC CAGGTTCAAC GTATGCCAGC TTAAACGGTA CATCGATGGC TACTCCTCAT    660

GTTGCAGGTG TTGCAGCCCT TGTTAAACAA AAGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                        807
```

(2) INFORMATION FOR SEQ ID NO:90:

(i) SEQUENCE CHARACTERISTICS:
       (A) LENGTH: 807 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (B) STRAIN: Bacillus lentus DSM 5483

(vii) IMMEDIATE SOURCE:
       (B) CLONE: S139A (xi) SEQUENCE DESCRIPTION: SEQ ID NO:90:

```
GCGCAATCAG TGCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATGCAGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CGCAGGGCTT GACATTGTCG CACCAGGGGT AAACGTGCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AAGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                        807
```

(2) INFORMATION FOR SEQ ID NO:91:

(i) SEQUENCE CHARACTERISTICS:
       (A) LENGTH: 807 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (B) STRAIN: Bacillus lentus DSM 5483

(vii) IMMEDIATE SOURCE:
       (B) CLONE: S142T (xi) SEQUENCE DESCRIPTION: SEQ ID NO:91:

```
GCGCAATCAG TGCCATGGGG AATTAGCCGT GTGCAAGCCC CGGCTGCCCA TAACCGTGGA        60

TTGACAGGTT CTGGTGTAAA AGTTGCTGTC CTCGATACAG GTATTTCCAC TCATCCAGAC       120

TTAAATATTC GTGGTGGCGC TAGCTTTGTA CCAGGGGAAC CATCCACTCA AGATGGGAAT       180

GGGCATGGCA CGCATGTGGC CGGGACGATT GCTGCTTTAA ACAATTCGAT TGGCGTTCTT       240

GGCGTAGCGC CTAGTGCGGA ACTATACGCT GTTAAAGTTT TAGGAGCCGA CGGTAGAGGT       300

GCAATCAGCT CGATTGCCCA AGGGTTGGAA TGGGCAGGGA ACAATGGCAT GCACGTTGCT       360

AATTTGAGTT TAGGAAGCCC TTCGCCAAGT GCCACACTTG AGCAAGCTGT TAATAGCGCG       420

ACTACAAGAG GCGTTCTTGT TGTAGCGGCA TCTGGGAATT CAGGTGCAAG CTCAATCAGC       480

TATCCGGCCC GTTATGCGAA CGCAATGGCA GTCGGAGCTA CTGACCAAAA CAACAACCGC       540

GCCAGCTTTT CACAGTATGG CGCAGGGCTT GACATTGTCG CACCAGGGGT AAACGTGCAG       600

AGCACATACC CAGGTTCAAC GTATGCCAGC TTAAACGGTA CATCGATGGC TACTCCTCAT       660

GTTGCAGGTG CAGCAGCCCT TGTTAAACAA AAGAACCCAT CTTGGTCCAA TGTACAAATC       720

CGCAACCATC TAAAGAATAC GGCAACGAGC TTAGGAAGCA CGAACTTGTA TGGAAGCGGA       780

CTTGTCAATG CAGAAGCGGC AACACGC                                           807
```

(2) INFORMATION FOR SEQ ID NO:92:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S139T (xi) SEQUENCE DESCRIPTION: SEQ ID NO:92:

```
GCGCAATCAG TGCCATGGGG AATTAGCCGT GTGCAAGCCC CGGCTGCCCA TAACCGTGGA        60

TTGACAGGTT CTGGTGTAAA AGTTGCTGTC CTCGATACAG GTATTTCCAC TCATCCAGAC       120

TTAAATATTC GTGGTGGCGC TAGCTTTGTA CCAGGGGAAC CATCCACTCA AGATGGGAAT       180

GGGCATGGCA CGCATGTGGC CGGGACGATT GCTGCTTTAA ACAATTCGAT TGGCGTTCTT       240

GGCGTAGCGC CTAGTGCGGA ACTATACGCT GTTAAAGTTT TAGGAGCCGA CGGTAGAGGT       300

GCAATCAGCT CGATTGCCCA AGGGTTGGAA TGGGCAGGGA ACAATGGCAT GCACGTTGCT       360

AATTTGAGTT TAGGAAGCCC TTCGCCAAGT GCCACACTTG AGCAAGCTGT TAATACAGCG       420

ACTTCTAGAG GCGTTCTTGT TGTAGCGGCA TCTGGGAATT CAGGTGCAAG CTCAATCAGC       480

TATCCGGCCC GTTATGCGAA CGCAATGGCA GTCGGAGCTA CTGACCAAAA CAACAACCGC       540

GCCAGCTTTT CACAGTATGG CGCAGGGCTT GACATTGTCG CACCAGGGGT AAACGTGCAG       600

AGCACATACC CAGGTTCAAC GTATGCCAGC TTAAACGGTA CATCGATGGC TACTCCTCAT       660

GTTGCAGGTG CAGCAGCCCT TGTTAAACAA AAGAACCCAT CTTGGTCCAA TGTACAAATC       720

CGCAACCATC TAAAGAATAC GGCAACGAGC TTAGGAAGCA CGAACTTGTA TGGAAGCGGA       780
```

```
        CTTGTCAATG CAGAAGCGGC AACACGC                              807

(2) INFORMATION FOR SEQ ID NO:93:

(i) SEQUENCE CHARACTERISTICS:
         (A) LENGTH: 807 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (B) STRAIN: Bacillus lentus DSM 5483

(vii) IMMEDIATE SOURCE:
         (B) CLONE: I102W (xi) SEQUENCE DESCRIPTION: SEQ ID NO:93:

GCGCAATCAG TGCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC   120

TTAAATATTC GTGGTGGCGC TAGCTTTGTA CCAGGGGAAC CATCCACTCA AGATGGGAAT   180

GGGCATGGCA CGCATGTGGC CGGGACGATT GCTGCTTTAA ACAATTCGAT TGGCGTTCTT   240

GGCGTAGCGC CTAGTGCGGA ACTATACGCT GTTAAAGTTT TAGGAGCCGA CGGTAGAGGT   300

GCATGGAGCT CGATTGCCCA AGGGTTGGAA TGGGCAGGGA ACAATGGCAT GCACGTTGCT   360

AATTTGAGTT TAGGAAGCCC TTCGCCAAGT GCCACACTTG AGCAAGCTGT TAATAGCGCG   420

ACTTCTAGAG GCGTTCTTGT TGTAGCGGCA TCTGGGAATT CAGGTGCAAG CTCAATCAGC   480

TATCCGGCCC GTTATGCGAA CGCAATGGCA GTCGGAGCTA CTGACCAAAA CAACAACCGC   540

GCCAGCTTTT CACAGTATGG CGCAGGGCTT GACATTGTCG CACCAGGGGT AAACGTGCAG   600

AGCACATACC CAGGTTCAAC GTATGCCAGC TTAAACGGTA CATCGATGGC TACTCCTCAT   660

GTTGCAGGTG CAGCAGCCCT TGTTAAACAA AAGAACCCAT CTTGGTCCAA TGTACAAATC   720

CGCAACCATC TAAAGAATAC GGCAACGAGC TTAGGAAGCA CGAACTTGTA TGGAAGCGGA   780

CTTGTCAATG CAGAAGCGGC AACACGC                                      807

(2) INFORMATION FOR SEQ ID NO:94:

(i) SEQUENCE CHARACTERISTICS:
         (A) LENGTH: 807 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (B) STRAIN: Bacillus lentus DSM 5483

(vii) IMMEDIATE SOURCE:
         (B) CLONE: A96N (xi) SEQUENCE DESCRIPTION: SEQ ID NO:94:

GCGCAATCAG TGCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC   120
```

| | |
|---|---|
| TTAAATATTC GTGGTGGCGC TAGCTTTGTA CCAGGGGAAC CATCCACTCA AGATGGGAAT | 180 |
| GGGCATGGCA CGCATGTGGC CGGGACGATT GCTGCTTTAA ACAATTCGAT TGGCGTTCTT | 240 |
| GGCGTAGCGC CTAGTGCGGA ACTATACGCT GTTAAAGTTT TAGGAAACGA CGGTAGAGGT | 300 |
| GCAATCAGCT CGATTGCCCA AGGGTTGGAA TGGGCAGGGA ACAATGGCAT GCACGTTGCT | 360 |
| AATTTGAGTT TAGGAAGCCC TTCGCCAAGT GCCACACTTG AGCAAGCTGT TAATAGCGCG | 420 |
| ACTTCTAGAG GCGTTCTTGT TGTAGCGGCA TCTGGGAATT CAGGTGCAAG CTCAATCAGC | 480 |
| TATCCGGCCC GTTATGCGAA CGCAATGGCA GTCGGAGCTA CTGACCAAAA CAACAACCGC | 540 |
| GCCAGCTTTT CACAGTATGG CGCAGGGCTT GACATTGTCG CACCAGGGGT AAACGTGCAG | 600 |
| AGCACATACC CAGGTTCAAC GTATGCCAGC TTAAACGGTA CATCGATGGC TACTCCTCAT | 660 |
| GTTGCAGGTG CAGCAGCCCT TGTTAAACAA AAGAACCCAT CTTGGTCCAA TGTACAAATC | 720 |
| CGCAACCATC TAAAGAATAC GGCAACGAGC TTAGGAAGCA CGAACTTGTA TGGAAGCGGA | 780 |
| CTTGTCAATG CAGAAGCGGC AACACGC | 807 |

(2) INFORMATION FOR SEQ ID NO:95:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: N42F (xi) SEQUENCE DESCRIPTION: SEQ ID NO:95:

| | |
|---|---|
| GCGCAATCAG TGCCATGGGG AATTAGCCGT GTGCAAGCCC CGGCTGCCCA TAACCGTGGA | 60 |
| TTGACAGGTT CTGGTGTAAA AGTTGCTGTC CTCGATACAG GTATTTCCAC TCATCCAGAC | 120 |
| TTATTTATTC GTGGTGGCGC TAGCTTTGTA CCAGGGGAAC CATCCACTCA AGATGGGAAT | 180 |
| GGGCATGGCA CGCATGTGGC CGGGACGATT GCTGCTTTAA ACAATTCGAT TGGCGTTCTT | 240 |
| GGCGTAGCGC CTAGTGCGGA ACTATACGCT GTTAAAGTTT TAGGAGCCGA CGGTAGAGGT | 300 |
| GCAATCAGCT CGATTGCCCA AGGGTTGGAA TGGGCAGGGA ACAATGGCAT GCACGTTGCT | 360 |
| AATTTGAGTT TAGGAAGCCC TTCGCCAAGT GCCACACTTG AGCAAGCTGT TAATAGCGCG | 420 |
| ACTTCTAGAG GCGTTCTTGT TGTAGCGGCA TCTGGGAATT CAGGTGCAAG CTCAATCAGC | 480 |
| TATCCGGCCC GTTATGCGAA CGCAATGGCA GTCGGAGCTA CTGACCAAAA CAACAACCGC | 540 |
| GCCAGCTTTT CACAGTATGG CGCAGGGCTT GACATTGTCG CACCAGGGGT AAACGTGCAG | 600 |
| AGCACATACC CAGGTTCAAC GTATGCCAGC TTAAACGGTA CATCGATGGC TACTCCTCAT | 660 |
| GTTGCAGGTG CAGCAGCCCT TGTTAAACAA AAGAACCCAT CTTGGTCCAA TGTACAAATC | 720 |
| CGCAACCATC TAAAGAATAC GGCAACGAGC TTAGGAAGCA CGAACTTGTA TGGAAGCGGA | 780 |
| CTTGTCAATG CAGAAGCGGC AACACGC | 807 |

(2) INFORMATION FOR SEQ ID NO:96:

(i) SEQUENCE CHARACTERISTICS:
        (A) LENGTH: 807 base pairs

```
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (B) STRAIN: Bacillus lentus DSM 5483

(vii) IMMEDIATE SOURCE:
            (B) CLONE: S142A (xi) SEQUENCE DESCRIPTION: SEQ ID NO:96:

GCGCAATCAG TGCCATGGGG AATTAGCCGT GTGCAAGCCC CGGCTGCCCA TAACCGTGGA    60

TTGACAGGTT CTGGTGTAAA AGTTGCTGTC CTCGATACAG GTATTTCCAC TCATCCAGAC   120

TTAAATATTC GTGGTGGCGC TAGCTTTGTA CCAGGGGAAC CATCCACTCA AGATGGGAAT   180

GGGCATGGCA CGCATGTGGC CGGGACGATT GCTGCTTTAA ACAATTCGAT TGGCGTTCTT   240

GGCGTAGCGC CTAGTGCGGA ACTATACGCT GTTAAAGTTT TAGGAGCCGA CGGTAGAGGT   300

GCAATCAGCT CGATTGCCCA AGGGTTGGAA TGGGCAGGGA ACAATGGCAT GCACGTTGCT   360

AATTTGAGTT TAGGAAGCCC TTCGCCAAGT GCCACACTTG AGCAAGCTGT TAATAGCGCG   420

ACTGCAAGAG GCGTTCTTGT TGTAGCGGCA TCTGGGAATT CAGGTGCAAG CTCAATCAGC   480

TATCCGGCCC GTTATGCGAA CGCAATGGCA GTCGGAGCTA CTGACCAAAA CAACAACCGC   540

GCCAGCTTTT CACAGTATGG CGCAGGGCTT GACATTGTCG CACCAGGGGT AAACGTGCAG   600

AGCACATACC CAGGTTCAAC GTATGCCAGC TTAAACGGTA CATCGATGGC TACTCCTCAT   660

GTTGCAGGTG CAGCAGCCCT TGTTAAACAA AAGAACCCAT CTTGGTCCAA TGTACAAATC   720

CGCAACCATC TAAAGAATAC GGCAACGAGC TTAGGAAGCA CGAACTTGTA TGGAAGCGGA   780

CTTGTCAATG CAGAAGCGGC AACACGC                                      807

(2) INFORMATION FOR SEQ ID NO:97:

(i) SEQUENCE CHARACTERISTICS:
            (A) LENGTH: 807 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (B) STRAIN: Bacillus lentus DSM 5483

(vii) IMMEDIATE SOURCE:
            (B) CLONE: H118F (xi) SEQUENCE DESCRIPTION: SEQ ID NO:97:

GCGCAATCAG TGCCATGGGG AATTAGCCGT GTGCAAGCCC CGGCTGCCCA TAACCGTGGA    60

TTGACAGGTT CTGGTGTAAA AGTTGCTGTC CTCGATACAG GTATTTCCAC TCATCCAGAC   120

TTAAATATTC GTGGTGGCGC TAGCTTTGTA CCAGGGGAAC CATCCACTCA AGATGGGAAT   180

GGGCATGGCA CGCATGTGGC CGGGACGATT GCTGCTTTAA ACAATTCGAT TGGCGTTCTT   240

GGCGTAGCGC CTAGTGCGGA ACTATACGCT GTTAAAGTTT TAGGAGCCGA CGGTAGAGGT   300

GCAATCAGCT CGATTGCCCA AGGGTTGGAA TGGGCAGGGA ACAATGGCAT GTTTGTTGCT   360
```

```
AATTTGAGTT TAGGAAGCCC TTCGCCAAGT GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AGAACCCAT CTTGGTCCAA TGTACAAATC       720

CGCAACCATC TAAAGAATAC GGCAACGAGC TTAGGAAGCA CGAACTTGTA TGGAAGCGGA      780

CTTGTCAATG CAGAAGCGGC AACACGC                                         807
```

(2) INFORMATION FOR SEQ ID NO:98:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: N237A (xi) SEQUENCE DESCRIPTION: SEQ ID NO:98:

```
GCGCAATCAG TGCCATGGGG AATTAGCCGT GTGCAAGCCC CGGCTGCCCA TAACCGTGGA       60

TTGACAGGTT CTGGTGTAAA AGTTGCTGTC CTCGATACAG GTATTTCCAC TCATCCAGAC      120

TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT TAGGAGCCGA CGGTAGAGGT      300

GCAATCAGCT CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AGAACCCAT CTTGGTCCGC TGTACAAATC       720

CGCAACCATC TAAAGAATAC GGCAACGAGC TTAGGAAGCA CGAACTTGTA TGGAAGCGGA      780

CTTGTCAATG CAGAAGCGGC AACACGC                                         807
```

(2) INFORMATION FOR SEQ ID NO:99:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (B) STRAIN: Bacillus lentus DSM 5483

(vii) IMMEDIATE SOURCE:
    (B) CLONE: N255P (xi) SEQUENCE DESCRIPTION: SEQ ID NO:99:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGCCATTGTA TGGAAGCGGA     780
CTTGTCAATG CAGAAGCGGC AACACGC                                        807
```

(2) INFORMATION FOR SEQ ID NO:100:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: T141W, N237A (xi) SEQUENCE DESCRIPTION: SEQ ID NO:100:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
TGGTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
```

```
GCCAGCTTTT CACAGTATGG CGCAGGGCTT GACATTGTCG CACCAGGGGT AAACGTGCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AAGAACCCAT CTTGGTCCGC TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                       807
```

(2) INFORMATION FOR SEQ ID NO:101:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: T268V (xi) SEQUENCE DESCRIPTION: SEQ ID NO:101:

```
GCGCAATCAG TGCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA CAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATAGCGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CGCAGGGCTT GACATTGTCG CACCAGGGGT AAACGTGCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AAGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AGTTCGC                                       807
```

(2) INFORMATION FOR SEQ ID NO:102:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:

(B) CLONE: K229W (xi) SEQUENCE DESCRIPTION: SEQ ID NO:102:

GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CGCAGGGCTT GACATTGTCG CACCAGGGGT AAACGTGCAG     600

AGCACATACC CAGGTTCAAC GTATGCCAGC TTAAACGGTA CATCGATGGC TACTCCTCAT     660

GTTGCAGGTG CAGCAGCCCT TGTTTGGCAA AAGAACCCAT CTTGGTCCAA TGTACAAATC     720

CGCAACCATC TAAAGAATAC GGCAACGAGC TTAGGAAGCA CGAACTTGTA TGGAAGCGGA     780

CTTGTCAATG CAGAAGCGGC AACACGC                                        807

(2) INFORMATION FOR SEQ ID NO:103:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: T141W (xi) SEQUENCE DESCRIPTION: SEQ ID NO:103:

GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

TGGTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CGCAGGGCTT GACATTGTCG CACCAGGGGT AAACGTGCAG     600

AGCACATACC CAGGTTCAAC GTATGCCAGC TTAAACGGTA CATCGATGGC TACTCCTCAT     660

GTTGCAGGTG CAGCAGCCCT TGTTAAACAA AAGAACCCAT CTTGGTCCAA TGTACAAATC     720

CGCAACCATC TAAAGAATAC GGCAACGAGC TTAGGAAGCA CGAACTTGTA TGGAAGCGGA     780

```
CTTGTCAATG CAGAAGCGGC AACACGC                                              807

(2) INFORMATION FOR SEQ ID NO:104:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: wild type (xi) SEQUENCE DESCRIPTION: SEQ ID NO:104:

GCGCAATCAG TGCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATAGCGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CGCAGGGCTT GACATTGTCG CACCAGGGGT AAACGTGCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AAGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                       807
```

MUTANT PROTEOLYTIC ENZYMES AND METHOD OF PRODUCTION

This application is a divisional of application Ser. No. 08/254,021 filed Jun. 2, 1994 which issued as U.S. Pat. No. 5,500,364, which is a divisional of application Ser. No. 07/706,691 filed May 29, 1991 which issued as U.S. Pat. No. 5,340,735.

BACKGROUND OF THE INVENTION

1. Field of the Invention

This invention relates to mutant proteolytic enzymes having improved properties relative to the wild-type enzyme, to genetic constructs which code for the mutant proteolytic enzymes, to methods of predicting mutations which enhance the stability of the enzyme, and to methods of producing the mutant proteolytic enzymes.

2. Description of the Related Art

Subtilisins are a family of extracellular proteins having molecular weights in the range of 25,000–35,000 daltons and are produced by various Bacillus species. These proteins function as peptide hydrolases in that they catalyze the hydrolysis of peptide linkages in protein substrates at neutral and alkaline pH values. Subtilisins are termed serine proteases because they contain a specific serine residue which participates in the catalytic hydrolysis of peptide substrates. A subtilisin enzyme isolated from soil samples and produced by *Bacillus lentus* for use in detergent formulations having increased protease and oxidative stability over commercially available enzymes under conditions of pH 7 to 10 and at temperature of 10 to 60° C. in aqueous solutions has been disclosed in copending patent application Ser. No. 07/398,854, filed on Aug. 25, 1989. This *B. lentus* alkaline protease enzyme (BLAP, vide infra) is obtained in commercial quantities by cultivating a *Bacillus licheniformis* ATCC 53926 strain which had been transformed by an expression plasmid which contained the wild type BLAP gene and the *B. licheniformis* ATCC 53926 alkaline protease gene promoter.

Industrial processes generally are performed under physical conditions which require highly stable enzymes. Enzymes may be inactivated by high temperatures, pH extremes, oxidation, and surfactants. Even though *Bacillus subtilisin* proteases are currently used in many industrial applications, including detergent formulations, stability improvements are still needed. Market trends are toward more concentrated detergent powders, and an increase in liquid formulations. Increased shelf stability and oxidative stability, with retention of catalytic efficiency are needed. It is therefore desirable to isolate novel enzymes with increased stability, or to improve the stability of existing enzymes, including subtilisin proteases such as BLAP.

The stability of a protein is a function of its three dimensional structure. A protein folds into a three dimensional conformation based upon the primary amino acid sequence, and upon its surrounding environment. The function and stability of a protein are a direct result of its three dimensional structure.

A large body of information has been published which describes changes in enzyme properties as a result of alterations in the primary amino acid sequence of the enzyme. These alterations can result from random or site specific alterations of the gene which expresses the enzyme using genetic engineering techniques. Random approaches mutagenize total cellular DNA, followed by selection for the synthesis of an enzyme with improved properties. This approach requires neither knowledge of the three dimensional structure of the enzyme, nor any predictive capability on the part of the researcher. Site directed mutagenesis, on the other hand, requires a rational approach for the introduction of amino acid changes. In this approach one or more amino acids may be replaced by other residues by altering the DNA sequence which encodes the protein. This can be accomplished using oligonucleotide directed in vitro mutagenesis. The following references teach site-directed mutagenesis procedures used to generate specific amino acid substitution(s): Hines, J. C., and Ray, D. S. (1980) Gene 11:207–218; Zoller, M. J., and Smith, M. (1982) Nucleic Acids Res. 10:6487–6500; Norrander, J., et al. (1983) Gene 26:101–106; Morinaga, Y., et al. (1984) Bio/Technology 2:636–639; Kramer, W., et al. (1984) Nucleic Acids Res. 12:9441–9456; Carter, P., et al. (1985) Nucleic Acids Res. 13:4431–4443; Kunkel, T. A. (1985) Proc. Natl. Acad. Sci. USA 82:488–492; Bryan, P., et al. (1986) Proc. Natl. Acad. Sci. USA 83:3743–3745.

A rational approach may or may not require knowledge of a protein's structure. For example, patent application WO 89/06279 describes the comparison of the primary amino acid sequence of different subtilisins while contrasting differences in physical and chemical properties. The primary amino acid sequences of the different subtilisins are aligned for the greatest homology, while taking into account amino acid insertions, deletions, and total number of amino acids.

Currently, the amino acid sequences of at least 10 subtilisin proteases have been published. Eight of these subtilisins were isolated from species of Bacilli, and include subtilisin 168 (Stahl, M. L., and Ferrari, E. (1984) J. Bacteriol. 158:411–418), subtilisin BPN' (Vasantha, N., et al., (1984) J. Bacteriol. 159:811–819), subtilisin Carlsberg (Jacobs, M., et al. (1985) Nucleic Acids Res. 13:8913–8926), subtilisin DY (Nedkov, P., et al. (1985) Biol. Chem. Hoppe-Seyler 366:421–430), subtilisin amylosaccharitcus (Kurihara, M., et al. (1972) J.Biol. Chem. 247:5619–5631), subtilisin mesenticopeptidase (Svendsen, I., et al. (1986) FEBS Lett. 196:228–232), subtilisin 147 and subtilisin 309 (Hastrup et al. (1989) WO 89/06279), subtilisin PB92 (Van Eekelen et al. (1989) EP 0328229), and subtilisin BLAP (Ladin, B., et al. (1990) Society for Industrial Microbiology Annual Meeting, Abstract P60). The remaining two subtilisin sequences are thermitase from the fungus *Thermoactinomyces vulgaris* (Meloun, B., et al. (1985) FEBS Lett. 183:195–200), and proteinase K from the fungus *Tritirachium album* limber (Jany, K. -D., and Mayer, B. (1985) Biol. Chem. Hoppe-Seyler 366:485–492).

Methods for obtaining optimum alignment of homologous proteins are described in Atlas of Protein Sequence and Structure, Vol. 5, Supplement 2 (1976) (Dayhoff, M. O., ed., Natl. Biomed. Res. Found., Silver Springs, Md.). This comparison is then used to identify specific amino acid alterations which might produce desirable improvements in the target enzyme. Wells, J. A., et al. (1987) Proc. Natl. Acad. Sci. USA 84:1219–1223, used primary sequence alignment to predict site directed mutations which affect the substrate specificity of a subtilisin. Using the alignment approach WO 89/06279 teaches the construction of mutant subtilisins having improved properties including an increased resistance to oxidation, increased proteolytic activity, and improved washing performance for laundry detergent applications. Patent applications WO 89/09819, and WO 89/09830 teach improvement in the thermal stability of subtilisin BPN' by the introduction of one or more amino acid changes based on the alignment of the primary amino acid sequences of subtilisin BPN' with the more thermal stable subtilisin Carlsberg. From hereon, amino acids will be referred to by the one or three letter code as defined in Table 1.

TABLE 1

One and Three Letter Code for Amino Acids

A = Ala = Alanine
C = Cys = Cysteine
D = Asp = Aspartic acid or aspartate
E = Glu = Glutamic acid or glutamate
F = Phe = Phenylalanine
G = Gly = Glycine
H = His = Histidine
I = Ile = Isoleucine
K = Lys = Lysine
L = Leu = Leucine
M = Met = Methionine
N = Asn = Asparagine
P = Pro = Proline
Q = Gln = Glutamine
R = Arg = Arginine
S = Ser = Serine
T = Thr = Threonine
V = Val = Valine
W = Trp = Tryptophan
Y = Tyr = Tyrosine Rational mutational approaches may also predict mutations which improve an enzyme property based upon the three dimensional structure of an enzyme, in addition to the alignment of primary amino acid sequences described above. One method for determining the three dimensional structure of a protein involves the growing of crystals of the protein, followed by X-ray crystallographic analysis. This technique has been successfully used to determine several high resolution subtilisin structures such as thermitase (Teplyakov, A. V., et al. (1990) 214:261–279), subtilisin BPN' (Bott, R., et al. (1988) J. Biol. Chem. 263:7895–7906) and subtilisin Carlsberg (Bode, W., et al. (1986) EMBO J. 5:813–818), for example.

EP 0251446 teaches the construction of mutant carbonyl hydrolases (proteases) which have at least one property different from the parental carbonyl hydrolase. It describes mutations which effect (either improve or decrease) oxidative stability, substrate specificity, catalytic activity, thermal stability, alkaline stability, pH activity profile, and resistance to autoproteolysis. These mutations were selected for introduction into *Bacillus amyloliquefaciens* subtilisin BPN' after alignment of the primary sequences of BPN' and proteases from *B. subtilis, B. licheniformis*, and thermitase. Such alignment can then be used to select amino acids in these other proteases which differ, as substitutes for the equivalent amino acid in the *B. amyloliquefaciens* carbonyl hydrolase. This application also describes alignment on the basis of a 1.8 Å X-ray crystal structure of the *B. amyloliquefaciens* protease. Amino acids in the carbonyl hydrolase of *B. amyloliquefaciens* which when altered can affect stability, substrate specificity, or catalytic efficiency include: Met50, Met124, and Met222 for oxidative stability; Tyr104, Ala152, Glu156, Gly166, Gly169, Phe189, and Tyr217 for substrate specificity; N155 alterations were found to decrease turnover, and lower Km; Asp36, Ile107, Lys170, Asp197, Ser204, Lys213, and Met222 for alkaline stability; and Met199, and Tyr21 for thermal stability. Alteration of other amino acids was found to affect multiple properties of the protease. Included in this category are Ser24, Met50, Asp156, Gly166, Gly169, and Tyr217. Substitution at residues Ser24, Met50, Ile107, Glu156, Gly166, Gly169, Ser204, Lys213, Gly215, and Tyr217 was predicted to increase thermal and alkaline stability. An important point about this patent application is that with the exception of those mutations effecting substrate specificity, no rational mutational approach for improving the alkaline or temperature stability of a protease based upon computer simulations of an X-ray crystal structure is described.

WO 88/08028 teaches a method for redesigning proteins to increase stability by altering amino acid residues that are in close proximity to the protein's metal ion binding site. This application describes the alteration of a calcium ion binding site present within subtilisin BPN' through the substitution, insertion, or deletion of amino acid residue(s) in close proximity to that site so that the electrostatic attraction between the amino acids and the calcium ion is increased. The characterization of the calcium ion binding site is accomplished through the analysis of a 1.3 Å three dimensional structure of subtilisin BPN' using a high resolution computer graphics system. This approach allows the selection of amino acids acceptable for replacing the native amino acids in the protease by first simulating the change using the computer model. This allows for the identification of any problems including steric hindrance prior to the actual construction and testing of the mutant proteases.

U.S. Pat. Nos. 4,908,773 and 4,853,871 teach a computer based method for evaluating the three dimensional structure of a protein to select amino acid residues where the introduction of a novel disulfide bond will potentially stabilize the protein. Potentially acceptable amino acid residues can then be ranked, and replaced using computer simulation, prior to the actual construction of the mutant protein using site directed mutagenesis protocols.

Several patent applications combine published data on biochemical stability with computer analysis of three dimensional protease structures in order to predict mutations which stabilize the enzyme. U.S. Pat. No. 4,914,031 and WO 88/08033 and WO 87/04461 teach a method for improving the pH and thermal stability of subtilisin aprA by replacing asparagine residues present in asparagine/glycine pairs. Asparagine/glycine pairs in proteins have been shown to undergo cyclization to form cyclic imide anhydroaspartylglycine (Bornstein, P., and Balian, G. (1977) Methods Enzymol. 47:132–145). This cyclic imide is susceptible to base hydrolyzed cleavage leading to inactivation of the enzyme. Computer analysis of the three dimensional structure of the aprA protease also predicted that formation of the cyclic imide could lead to protease inactivation resulting from a shift of the side chain of the active site serine. The decision to replace the asparagine residue and not the glycine residue was based upon alignment of the aprA sequence with other subtilisin-like enzymes, cucumisin and proteinase K.

Sensitivity to oxidation is an important deficiency of serine proteases used in detergent applications (Stauffer, C. E., and Etson, D. (1969) J. Biol. Chem. 244:5333–5338). EP 0130756, EP 0247647, and U.S. Pat. No. 4,760,025 teach a saturation mutation method where one or multiple mutations are introduced into the subtilisin BPN' at amino acid residues Asp32, Asn155, Tyr104, Met222, Gly166, His64, Ser221, Gly169, Glu156, Ser33, Phe189, Tyr217, and/or Ala152. Using this approach mutant proteases exhibiting improved oxidative stability, altered substrate specificity, and/or altered pH activity profiles are obtained. A method is taught in which improved oxidative stability is achieved by substitution of methionine, cysteine, tryptophan, and lysine residues. These publications also teach that mutations within the active site region of the protease are also most likely to influence activity. Random or selected mutations can be introduced into a target gene using the experimental approach but neither EP 0130756, EP 0247647, nor U.S. Pat. No. 4,760,025 teach a method for predicting amino acid alterations which will improve the thermal or surfactant stability of the protease.

WO 8705050 teaches a random mutagenesis approach for construction of subtilisin mutants exhibiting enhanced thermal stability. One or more random mutations are introduced into single stranded target DNA using the chemical mutagens sodium bisulfite, nitrous acid, and formic acid. Subsequently, the mutated DNA is transformed into a Bacillus host and at least 50,000 colonies are screened by a filter assay to identify proteases with improved properties. Site directed mutagenesis can then be used to introduce all possible mutations into a site identified through the random mutagenesis screen. No method for pre selection of amino acids to be altered is taught.

EP 0328229 teaches the isolation and characterization of PB92 subtilisin mutants with improved properties for laundry detergent applications based upon wash test results. It teaches that biochemical properties are not reliable parameters for predicting enzyme performance in the wash. Methods for selection of mutations involve the substitution of amino acids by other amino acids in the same category (polar, nonpolar, aromatic, charged, aliphatic, and neutral), the substitution of polar amino acids asparagine and glutamine by charged amino acids, and increasing the anionic character of the protease at sites not involved with the active site. No method for identifying which specific amino acids should be altered is taught, and no rational mutational approach is taught which is based on alignment of X-ray structures of homologous proteases with different properties.

EP 0260105 teaches the construction of subtilisin BPN' mutants with altered transesterification rate/hydrolysis rate ratios and nucleophile specificities by changing specific amino acid residues within 15 Å of the catalytic triad. Russell, A. J., and Fersht, A. R. (1987) Nature 328:496–500, and Russell, A. J., et al. (1987) J. Mol. Biol. 193:803–813, teach the isolation of a subtilisin BPN' mutant (D099S) that had a change in the surface charge 14–15 Å from the active site. This substitution causes an effect on the pH dependence of the subtilisin's catalytic reaction.

There are a number of different strategies for increasing protein stability. Many of these methods suggest types of substitutions to improve the stability of a protein but do not teach a method for identifying amino acid residues within a protein which should be substituted. From entropic arguments, many types of substitutions have been suggested such as Gly to Ala and any amino acid to Pro (Matthews, B. W., et al. (1987) Proc. Natl. Acad. Sci. 84:6663–6667). Likewise, while it is clear that increasing the apolar size of an amino acid in the core will add to stability, adverse packing effects may more than compensate for the hydrophobic effect, resulting in a decrease in protein stability (Sandberg, W. S., and Terwilliger, T. C. (1989) Science 245:54–57). Menéndez-Arias, L., and Argos, P. (1990) J. Mol. Biol. 206:397–406, performed a statistical evaluation of amino acid substitutions of thermophilic and mesophilic molecules and proposed that decreased flexibility and increased hydrophobicity in the α-helical regions contributes most towards increasing protein stability. From their data, they formulated a set of empirical rules to improve stability.

Increasing the hydrophobicity of certain side chains has long been suggested as a means to improve protein stability. The hydrophobic exclusion of nonpolar amino acids is the largest force driving protein folding. This has been studied by examining the partitioning of amino acids or amino acid analogs from water to a hydrophobic medium. While the numbers vary depending on the work, these studies generally agree that burying a hydrophobic side chain increases protein stability. For example, Kellis, J. T., Jr., et al. (1988) Nature 333:784–786, estimated that the removal of a methyl group destabilizes the enzyme by 1.1 kcal/mole assuming no other structural perturbations occur. Conversely, this predicts that the addition of a methylene group should add 1.1 kcal/mol if no unfavorable contacts occur. Similarly, Sandberg, W. S., and Terwilliger, T. C. (1989) Science 245:54–57, showed that the effect of removing or adding methylene groups is the sum of the hydrophobic effect and structural distortions. Simply adding buried hydrophobic groups may not increase protein stability because the total effect of adding or deleting a methyl group on the local packing structure must be considered. As the protein interior has a para-crystalline structure (Chothia, C. (1975) Nature 254:304–308), small distortions in the remainder of the structure resulting from the addition methyl group may exact a high cost and reduce rather than increase stability.

Along the same lines, the core of λ repressor has been shown to be amazingly tolerant to apolar amino acid substitutions in a functional assay (Bowie, J. U., et al. (1990) Science 247:1306–1310). It is not clear that this is true for larger proteins. The constraints on the hydrophobic core of a small protein may be less stringent than a larger protein simply due to the volume of the core relative to the number of amino acids which need to pack into the region. As the volume of the hydrophobic core increases, the number of amino acids which must pack together correctly increases, requiring more specific nonlocal interactions.

It has been recognized that increasing the interior hydrophobicity of a protein as a means of increasing the stability is hampered by the difficulty of determining which positions in the protein will lead to stabilization when substituted (Sandberg, W. S., and Terwilliger, T. C. (1991) Trends Biotechnol. 9:59–63). The methods discussed above provide a means of determining what substitutions to make to improve stability but do not identify which sites in the protein are most important. The present invention provides a method of determining which positions in the protein will lead to stabilization when substituted.

SUMMARY OF THE INVENTION

Other than in the operating examples, or where otherwise indicated, all numbers expressing quantities of ingredients or reaction conditions used herein are to be understood as modified in all instances by the term "about".

The native or wild-type protease from which the mutant proteases according to the invention are derived is a *B. lentus* alkaline protease (BLAP) obtained from *B. lentus* DSM 5483 having 269 amino acid residues, a molecular mass of 26,823 daltons, and a calculated isoelectric point of 9.7 based on standard pK values. The BLAP gene is obtained by isolating the chromosomal DNA from the *B. lentus* strain DSM 5483, constructing DNA probes having homology to putative DNA sequences encoding regions of the *B. lentus* protease, preparing genomic libraries from the isolated chromosomal DNA, and screening the libraries for the gene of interest by hybridization to the probes.

Mutant *B. lentus* DSM 5483 proteases have been made which are derived by the replacement of at least one amino acid residue of the mature form of the *B. lentus* DSM 5483 alkaline protease. The sites for replacement are selected from the group consisting of Ser3, Val4, Ser36, Asn42, Ala47, Thr56, Thr69, Glu87, Ala96, Ala101, Ile102, Ser104, Asn114, His118, Ala120, Ser130, Ser139, Thr141, Ser142, Ser157, Ala188, Val193, Val199, Gly205, Ala224, Lys229, Ser236, Asn237, Asn242, His243, Asn255, Thr268. The replacement amino acid residues are listed in Table 2. The numbering of the mutant proteases is based on the *B. lentus* DSM 5483 wild-type protease as given in the SEQ ID NO:52.

Genes which express the mutant *B. lentus* DSM 5483 proteases according to the invention are made by altering one or more codons of the wild-type *B. lentus* DSM 5483 alkaline protease gene which encode for a protease derived by accomplishing at least one of the amino acid substitutions listed in Table 2.

The protease sites listed in Table 2 are sites predicted to affect thermal and surfactant stability relative to the wild-type protease. These sites are identified by means of a computer based method which compares the three dimensional structure of the wild-type protease (henceforth, the target protein) and a homologous protease (henceforth, the reference protein). The three dimensional coordinates of the wild-type protease are probed with an uncharged probe molecule to produce a probe-accessible surface which has an external surface the interior of which contains one or more probe-accessible internal cavities. The amino acids of the reference protein having side chains lying outside the solvent-accessible surface or inside the internal cavities of the target protein are identified by aligning the three dimensional coordinates of the target protein and the reference protein.

Proteins having greater thermal and surfactant stability are produced by replacing the amino acid in the target protein if the amino acid in the target protein can be changed without creating unacceptable steric effects. The amino acid in the target protein is altered by site directed mutagenesis of the gene which expresses the target protein.

Genetic constructs are made which contain in the direction of transcription a promoter, ribosomal binding site, initiation codon and the major portion of the pre region of the *Bacillus licheniformis* ATCC 53926 alkaline protease gene operably linked to a portion of the pre region and all of the pro and mature regions of the *Bacillus lentus* DSM 5483 alkaline protease gene followed by a 164 bp DNA fragment containing the transcription terminator from the ATCC 53926 alkaline protease gene. The *Bacillus lentus* DSM 5483 alkaline protease gene is altered to produce a mutant gene which encodes for a protease derived by accomplishing at least one of the amino acid substitutions listed in Table 2. Mutant protease is made by fermenting a Bacillus strain transformed with a genetic construct containing a mutated *Bacillus lentus* DSM 5483 alkaline protease gene.

BRIEF DESCRIPTION OF THE FIGURES

FIG. 1 shows the atomic coordinates for *Bacillus lentus* alkaline protease (BLAP) to 1.4 Å resolution.

DESCRIPTION OF THE PREFERRED EMBODIMENTS

Figure 2:
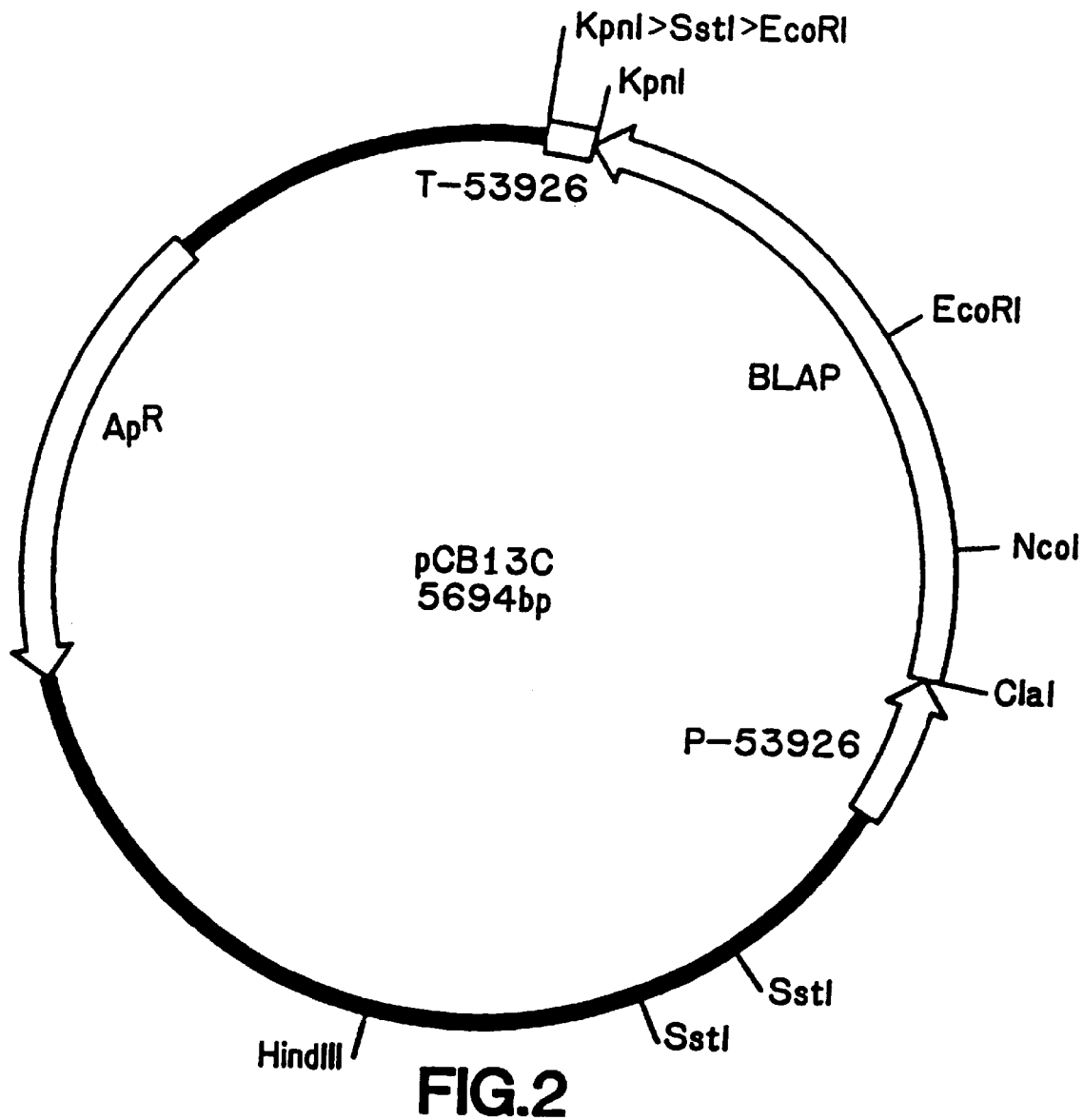
FIG. 2 shows the restriction map for plasmid pCB13C which contains a hybrid gene fusion between the *Bacillus licheniformis* ATCC 53926 protease gene and the Bacillus lentus DSM 5483 BLAP gene. The promoter, ribosomal binding site and presequence (P-53926) from ATCC 53926 were fused to the pro- and mature sequence of the BLAP gene. The transcription terminator of ATCC 53926 (T-53926) was appended to the BLAP coding region.

One aspect of the invention relates to mutant proteolytic enzymes which have superior thermal stability and surfactant stability relative to the wild-type protease as determined by laboratory tests. The mutant proteases according to the invention are those derived by the replacement of at least one amino acid residue of the mature *Bacillus lentus* DSM 5483 alkaline protease wherein said one amino acid residue which is selected from the group consisting of Ser3, Val4, Ser36, Asn42, Ala47, Thr56, Thr69, Glu87, Ala96, Ala101, Ile102, Ser104, Asn114, His118, Ala120, Ser130, Ser139, Thr141, Ser142, Ser157, Ala188, Val193, Val199, Gly205, Ala224, Lys229, Ser236, Asn237, Asn242, His243, Asn255, Thr268 is replaced with the amino acid residues listed in Table 2. Table 2 shows the identity and position of the wild-type amino acid and the amino acid residue(s) which replace it in the mutant protein. For example, the first entry in Table 2 shows Ser3, a serine residue at position 3 which can be replaced by threonine (abbreviated as T using the one letter code for amino acids) or any small amino acid. A small amino acid is defined as glycine, alanine, valine, serine, threonine or cysteine. A small hydrophobic amino acid is defined as glycine, alanine, threonine, valine or isoleucine. A charged amino acid is defined as lysine, arginine, histidine, glutamate or aspartate. The abbreviation a.a. stands for "amino acid" residue.

TABLE 2

| Residue | Replacement Amino Acid |
| --- | --- |
| Ser3 | T or any small, hydrophobic a.a. |
| Val4 | I, S or any small a.a. |
| Ser36 | A, T or any small a.a. |
| Ser42 | F, A, T, V, I, Y |
| Ala47 | W or any small a.a. except A |
| Thr56 | V, S or any small, hydrophobic a.a. |
| Thr69 | R, A or any charged a.a. |
| Glu87 | R, M or any charged a.a. |
| Ala96 | I, N, S or any small, hydrophobic a.a. |
| Ala101 | T, S or any small, hydrophobic a.a. |
| Ile102 | W or any small a.a. except P |
| Ser104 | T or any small hydrophobic a.a. |
| Asn114 | S, Q or any small, hydrophobic a.a. |
| His118 | F or any a.a. except P and W |
| Ala120 | V or any small, hydrophobic a.a. |
| Ser130 | A, T or any small, hydrophobic a.a. |
| Ser139 | A, T, Y or any a.a. except P and W |
| Thr141 | W or any a.a. except P |
| Ser142 | A, T or any small, hydrophobic a.a. |
| Ser157 | T or any small, hydrophobic a.a. |
| Ala188 | P or any small, hydrophobic a.a. |
| Val193 | M or any small, hydrophobic a.a. |
| Val199 | I or any small, hydrophobic a.a. |
| Gly205 | V or any small, hydrophobic a.a. |
| Ala224 | V or any small, hydrophobic a.a. |
| Lys229 | W or any a.a. except P |
| Ser236 | A, T or any small, hydrophobic a.a. |
| Asn237 | A, N, Q, M or any small, hydrophobic a.a. |
| Asn242 | A, N, Q, M or any small, hydrophobic a.a. |
| His243 | A, N, Q, M or any small, hydrophobic a.a. |
| Asn255 | P or any small, hydrophobic a.a. |
| Thr268 | V or any small, hydrophobic a.a. |

The amino acid sequences of the preferred proteolytic enzymes are given in SEQ ID NO:1 to SEQ ID NO:51. The preferred mutated *B. lentus* DSM 5483 proteases which are encoded for by genes according to the invention as disclosed above are given in SEQ ID NO: 53 to 105. These proteases are produced by bacterial strains which have been transformed with plasmids containing a native or hybrid gene, mutated at one or more nucleotide base pairs by known mutagenesis methods. These mutant genes encode for proteases in which selected amino acid residues have been substituted for by other amino acids.

The mutant proteases according to the invention are listed in Table 3.

TABLE 3

| | Temperature Stability | | SDS Stability | |
|---|---|---|---|---|
| Mutation | 50° C., pH 11.0 t½ (min) | 60° C., pH 10.0 t½ (min) | pH 10.5, 50° C. t½ (min) | pH 8.6, 50° C. t½ (min) |
| S3T, V4I, A188P, V193M, V199I | 120 | 67 | 3.2 | 12 |
| S3T, A188P, V193M, V199I | 95 | 60 | 3.75 | 18.5 |
| V4I, A188P, V193M, V199I | 72 | 39 | 1.75 | 3.75 |
| S139Y, A188P, V193M, V199I | 69 | 33 | 1.4 | 4.6 |
| S130T, S139Y, A188P, V193M, V199I | 64 | 22 | 2 | 6.3 |
| A188P, V193M, V199I | 55 | 23.5 | 3.0 | 12.5 |
| S3T, A188P, V193M | 54 | 21 | 1.5 | 3.4 |
| S157T | 52 | 17.5 | 1.2 | 0.95 |
| A188P, V193M | 50 | 27 | 2.5 | 7.25 |
| A188P | 48 | 19 | 1.4 | 2.8 |
| S3T, V4I, A188P, V193M | 43 | 21 | 1.4 | 3.7 |
| V193M | 42 | 16.6 | 1.2 | 3.0 |
| S104T | 42 | 8 | 1.0 | 1.8 |
| T69V | 41 | 12.3 | 0.8 | 1.8 |
| V4I, A188P, V193M | 40 | 19 | 1.25 | 2.7 |
| A224V | 39 | 15 | 0.9 | 1.1 |
| V199I | 38.5 | 11.6 | 1.0 | 2.0 |
| V4I | 32.5 | 10 | 0.75 | 1.0 |
| S3T | 32 | 6.6 | 1.2 | 2.8 |
| S139Y | 26 | 8.8 | 1.0 | 2.0 |
| N242A | 26 | 7.4 | 0.9 | 1.9 |
| S236T | 25.5 | 8.4 | 1.0 | 2.0 |
| S36A | 23.8 | 8.6 | 0.9 | 1.8 |
| H243A | 23 | 5.9 | 0.8 | 1.7 |
| A101T | 23 | 4.7 | 0.5 | 2.75 |
| S236A | 23 | 5.1 | 0.8 | 1.3 |
| E87R | 22.5 | 9.0 | 0.4 | 1.2 |
| N114S | 22 | 7.9 | 1.1 | 1.3 |
| A47W | 21 | 7.2 | 0.9 | 1.05 |
| A120S | 20.5 | 8.4 | 0.9 | 1.4 |
| T56V | 20 | 8.5 | 0.8 | 0.7 |
| A120V | 20 | 11.8 | 0.65 | 1.9 |
| G205V | 20 | 6.8 | 1.1 | 2.8 |
| S130A | 20 | 8.8 | 0.4 | 1.0 |
| S130T | 20 | 7.2 | 0.4 | 1.1 |
| A96I | 19 | 12 | 1.0 | 1.4 |
| S104T, S139Y, A224V | 18 | 9.5 | 1.0 | 1.8 |
| S139A | 18.5 | 7.8 | 0.5 | 0.8 |
| S142T | 17.5 | 11.5 | 0.9 | 1.7 |
| S139T | 16.5 | 4.3 | 0.5 | 0.8 |
| I102W | 16.5 | 7.2 | 0.7 | 1.6 |
| A96N | 16 | 6 | 0.9 | 0.95 |
| N42F | 16 | 5.9 | 1.0 | 1.4 |
| S142A | 16 | 9 | 1.0 | 1.7 |
| H118F | 15.8 | 5.1 | 1.0 | 1.3 |
| N237A | 15 | 7.8 | 0.67 | 1.3 |
| N255P | 15.0 | 5.3 | 1.2 | 1.25 |
| T141W, N237A | 14 | 5.4 | 0.33 | 1.1 |
| T268V | 14 | 3.8 | 0.75 | 1.1 |
| K229W | 13.4 | 4.6 | 1.0 | 1.4 |
| T141W | 12 | 6.5 | 0.6 | 1.4 |
| wildtype | 12.0 | 3.0 | 0.8 | 1.6 |

Any of the proteases listed in Table 3 will exhibit greater stability in some manner than the wild-type protease BLAP. The entries under the "Mutation" heading of Table 3 shows the identity of the wild-type amino acid (using the one letter code), its position, and the amino acid which replaces it in the mutant protease. For example, S3T signifies that the serine at position 3 of the mature protease is replaced with a threonine. Some of the preferred mutant proteases are single replacements at specific locations such as a protease wherein valine at position 4 is replaced by isoleucine to specific combinations of replacements such as a protease wherein threonine at position 141 is replaced by tryptophan and asparagine at position 237 is replaced by alanine. The latter protease containing two replacements is one of only a number of possibilities.

The preferred mutant proteases according to the invention are identified as: (S3T, V4I, A188P, V193M, V199I); E87R; (S3T, A188P, V193M, V199I); N114S; (V4I, A188P, V193M, V199I); A47W; (S139Y, A188P, V193M, V199I); A120S; (S130T, S139Y, A188P, V193M, V199I); T56V; A120V;(A188P, V193M, V199I); G205V; (S3T, A188P, V193M); S130A; S130T; S157T; A96I; (S104T, S139Y, A224V); S139A; S142T; S139T; I102W; V193M; A96N; N42F; S142A; H118F; N237A; N255P; (T141W, N237A); T268V; K229W; T141W; (A188P, V193M); V4I; S3T; S139Y; N242A; S236T; S36A; H243A; A101T; S236A; A188P; (S3T, V4I, A188P, V193M); V193N; S104T; T69V; (V4I, A188P, V193M); A224V; V199I. The system used to designate the above preferred proteases first lists the amino acid residue in the mature form of the B. lentus DSM 5483 alkaline protease at the numbered position followed by the replacement amino acid residue using the one letter codes for amino acids. For example, V193M is a protease in which valine has been replaced by methionine at position 193 of the mature B. lentus DSM 5483 alkaline protease. A mutant protease identified by more than one such designation is a mutant protease which contains all of the indicated substitutions. For example, (A188P, V193M) is a protease in which valine has been replaced by methionine at position 193 of the mature B. lentus DSM 5483 protease and alanine at position 188 has been replaced by proline.

Mutant forms of the B. lentus DSM 5483 alkaline protease are prepared by site-specific mutagenesis of DNA encoding the mature form of either wild-type BLAP, or a mutant BLAP. The DNA fragment encoding the mature form of wild type BLAP was prepared using plasmid pCB13C. Plasmid pCB13C contains a hybrid fusion between the B. licheniformis ATCC 53926 protease gene and the B. lentus DSM 5483 BLAP gene, shown in FIG. 2. Specifically, this hybrid fusion contains DNA encoding the promoter, ribosomal binding site, and 21 residues of the pre sequence from the ATCC 53926 protease gene fused to a DNA sequence encoding the last five residues of the BLAP pre sequence and all of the pro and mature residues of BLAP. This fusion is referred to as the ClaI fusion because this restriction site is located at the juncture between the ATCC 53926 and DSM 5483 DNA's. A new ClaI restriction site had to be introduced into the ATCC 53926 alkaline protease gene near to the junction of the pre and pro sequences. The ClaI site was introduced into the ATCC 53926 alkaline protease gene by using a polymerase chain reaction (PCR) to amplify a DNA fragment containing sequence information from the N-terminal part of the ATCC 53926 alkaline protease gene. The amplified fragment included the ATCC 53926 alkaline protease promoter, ribosomal binding site, initiation codon, and most of the pre sequence. This 292 bp DNA fragment was flanked by AvaI and ClaI restriction sites at its 5' and 3' ends, respectively. The BLAP gene already contained a naturally occurring ClaI site at the corresponding position. Analysis of the DNA sequence across the fusion of the ATCC 53926 and BLAP genes confirmed the expected DNA and amino acid sequences.

Figure 3:
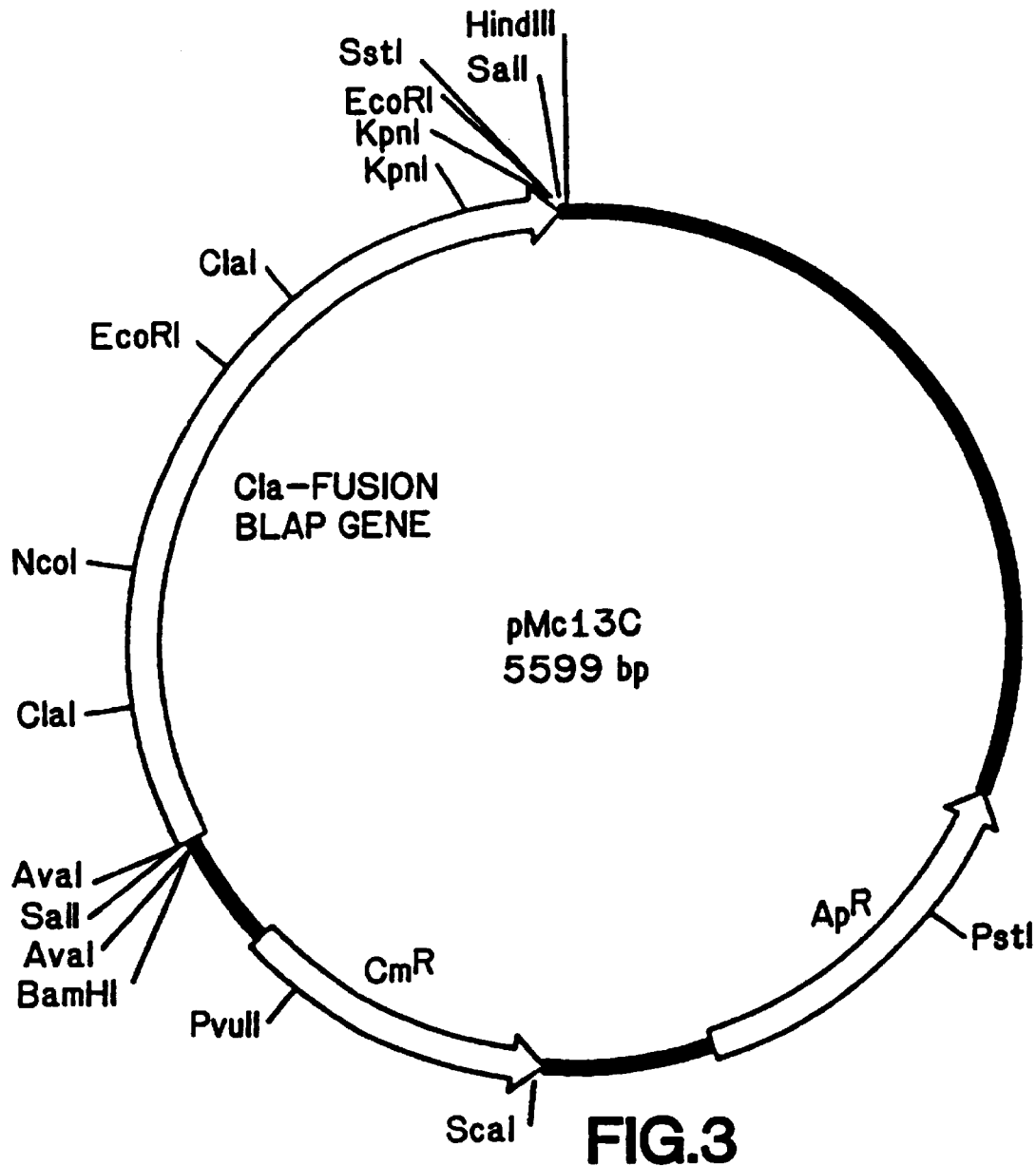
FIG. 3 shows the restriction map for plasmid pMc13C which is derived from pMac5-8 and contains the BLAP gene and carries an amber mutation in the $Ap^R$ gene which renders it inactive.

Before any mutagenesis can be carried out, the gene is subcloned into the mutagenesis vector pMa5-8. This is accomplished by synthesizing a DNA fragment containing the ClaI fusion gene and the ATCC 53926 transcription terminator as a SalI cassette using the PCR. The PCR was carried out using conditions as described by the manufacturer (Perkin Elmer Cetus, Norwalk, Conn.). In the PCR, two synthetic oligonucleotides bearing SalI sites are used as primers and *Escherichia coli* vector pCB13C DNA as a template. After cutting the PCR product with SalI, this fragment is cloned into the mutagenic plasmid pMc5-8 which has previously been cut with SalI and dephosphorylated with bacterial alkaline phosphatase. Plasmids pMc5-8, and pMa5-8 described below were obtained from H. -J. Fritz and are described by Stanssens, P., et al. (1989) Nucleic Acids Res. 17:4441–4454. SalI sites are chosen to allow the PCR fragment to be cloned into pMc5-8 in both orientations. The ligation mix is transformed into *E. coli* WK6. Chloramphenicol resistant ($Cm^R$) transformants are screened for the presence of an insert and a correct plasmid construct pMc13C is identified as shown in FIG. 3. Once the gene is cloned into the pMc vector and desirable sites for mutation are identified, the mutation(s) is introduced using synthetic DNA oligonucleotides according to a modification of a published protocol (Stanssens, P., et al. (1989) Nucleic Acids Res. 17:4441–4454). The oligonucleotide containing the mutation(s) to be introduced is annealed to a gapped duplex (gd) structure which carries the BLAP gene on a segment of single stranded (ss) DNA. The gapped duplex can be formed by annealing linear ss DNA from pMc13C with denatured and restricted pMa5-8 DNA. Plasmid pMa5-8 contains an active ampicillin resistance gene but has an inactivating point mutation in the chloramphenicol resistance gene, whereas plasmid pMc13C contains, in addition to an intact BLAP gene, an active chloramphenicol resistance gene, but has an inactivating point mutation in the ampicillin resistance gene. The annealed product is the gd DNA which is a double stranded heteroduplex with a ss DNA gap spanning the entire cloned BLAP gene. The mutant oligonucleotide is able to anneal to homologous ss BLAP DNA within the gap and the remaining gap is filled in by DNA polymerase I (Klenow fragment) and ligated using T4 DNA ligase, purchased from New England Biolabs Inc., Beverly, Mass. The mutagenic efficiency of such a system can be improved by the use of Exonuclease III (Exo III) purchased from New England Biolabs Inc., Beverly, Mass. Exo III is an exodeoxyribonuclease that digests double stranded DNA from the 3' end. As a free 3' end is required, closed circular ss DNA or ds DNA is unaffected by this enzyme. A subsequent treatment of the product of the fill-in reaction with Exo III removes any species with only partially filled gaps. This significantly improves the mutagenic efficiency and is the preferred mutagenesis method. The product of the fill-in reaction is then transformed into a repair deficient *E. coli* strain such as WK6mutS and ampicillin resistant transformants ($Ap^R$) are selected. Replication of the transformed heteroduplex phasmid results in two different progenies. One progeny contains the wild type BLAP gene and the intact chloramphenicol resistance gene, but an inactive ampicillin resistance gene. The other progeny contains a BLAP gene carrying the mutation of interest and is resistant to ampicillin but not to chloramphenicol.

Selection of $Ap^R$, $Cm^S$ mutant transformants with ampicillin is not sufficient to stop some background growth of the $Ap^S$, $Cm^R$ progeny carrying the wild type BLAP gene. Therefore, it is necessary to perform a second transformation into *E. coli* using plasmid DNA prepared from the $Ap^R$ transformants of the WK6mutS strain. This second transformation uses a low plasmid concentration with a large number of recipient cells of a suppressor deficient strain of *E. coli* such as WK6. This approach decreases the likelihood of a recipient cell receiving plasmid DNA from both progeny. $Ap^R$ transformants are selected and plasmid DNA from several transformants is isolated and screened for the presence of the mutation. The pMa mutant derivative of the first mutagenesis round can be used for a second round of mutagenesis by preparing ss DNA of that species and annealing it to XbaI/HindIII restricted and denatured DNA of pMc5-8. Plasmid pMc5-8 is identical to pMa5-8 except that it contains an active chloramphenicol resistance gene and an inactive ampicillin resistance gene. The general procedure is the same as that described above.

The mutant BLAP proteases can be produced by transferring the mutant BLAP genes from their particular *E. coli* pMa13C derivative vector into a plasmid vector which can replicate in Bacillus. To accomplish this, the mutant BLAP genes are separated from their pMa13C plasmids by digestion with the restriction endonucleases AvaI and SstI, followed by ligation to the larger AvaI/SstI fragment from either plasmid pH70 or pC51. These AvaI/SstI fragments from pH70 and pC51 include the DNA sequences necessary for replication in Bacillus and encode either kanamycin resistance ($Km^R$) or tetracycline resistance ($Tc^R$), respectively. Plasmid pH70 is constructed by cloning the ATCC 53926 alkaline protease gene carried on a EcoRI/BamHI DNA fragment into the $Km^R$ plasmid pUB110 between the EcoRI and BamHI sites. Plasmid pC51 is constructed by cloning the ATCC 53926 protease gene carried on a EcoRI-BamHI fragment into the $Tc^R$ plasmid pBC16 between the EcoRI and BamHI sites. The larger AvaI-SstI fragment from either pH70 or pC51 used for cloning the mutant BLAP genes is first purified from other DNA fragments by high pressure liquid chromatography (HPLC) on a Gen-Pak FAX column (Waters, Milford, Mass.). The column is 4.6 mm by 100 mm in size and contains a polymer-based high performance anion-exchange resin. Conditions for elution of the DNA are a flow rate of 0.75 ml/min with a gradient of Buffer A (25 mM tris (hydroxymethyl) aminomethane (Tris) pH 8.0 containing 1 mM disodium ethylenediamine tetraacetic acid (EDTA)) and Buffer B (25 mM Tris pH 8.0, 1 mM EDTA, 1 M NaCl) starting at 50% each and reaching a final concentration of 30% Buffer A and 70% Buffer B.

After ligation the mutant BLAP plasmids are transformed into *B. subtilis* DB104. The genes encoding the major alkaline and neutral proteases present in this strain have been inactivated (Kawamura, F., and Doi, R. A. (1984) J. Bacteriol. 160:442–444). Cells of *B. subtilis* DB104 transformed by these plasmids grow on a nutrient-skim milk agar in the presence of either kanamycin or tetracycline. Transformants of DB104 that manufacture mutant protease are identified by the formation of clear zones of hydrolysis in the skim milk. Confirmation that the protease-producing transformants carry a plasmid-borne BLAP gene with the desired mutation(s) is accomplished by purifying plasmid DNA from a culture of each transformant. The plasmid DNA is purified away from cell protein and chromosomal DNA by SDS-salt precipitation followed by chromatography over a Qiagen ion-exchange column (Qiagen Corporation, Studio City, Calif.). AvaI-SstI digested plasmid DNAs from different transformants are compared with AvaI/SstI-digested derivatives of plasmid pH70 or pC51 known to carry an intact BLAP gene. Restriction digests of these plasmids are compared by agarose gel electrophoresis to identify plasmids that have the proper-sized AvaI/SstI DNA fragments.

Selected plasmid DNAs are then sequenced across the region of the expected BLAP mutation(s) to confirm that the desired mutation(s) are present. One or more clones of each BLAP mutation are stored frozen in 15% glycerol at −70° C. and also cultivated in shake flasks (Example 4, Production of Proteases) to produce mutant protease for characterization.

Another aspect of the invention provides a computer based method for identifying the sites which affect the storage, thermal, SDS and pH stability of a protein. This method is based on the hypothesis that protein stability may be enhanced by decreasing the volume of internal cavities and improving surface packing of amino acid side chains. The interior of a protein contains many apolar amino acids which are tightly packed into a nearly crystalline state. One way in which these interior amino acids affect protein stability is through packing effects. These include van der Waal interactions, distortion of the remainder of the protein and electrostatic effects. Packing effects have been studied by measuring the contribution of methyl groups in the interior of a protein to the overall stability of the protein. It has been estimated that the removal of a methyl group from the interior of a protein destabilizes it by about 1.1 kcal/mol assuming no other perturbations occur (Kellis, J. T., Jr., et al. (1988) Nature 333:784–786). However, the inverse may not be true. Simply adding buried hydrophobic groups may not increase protein stability because the total effect of adding or deleting a methyl group on the local packing structure must be considered. As the protein interior has a para-crystalline structure (Chothia, C. (1975) Nature 254:304–308), small distortions in the remainder of the structure resulting from the addition methyl group may exact a high cost and reduce rather than increase stability.

While it is known in the art to make certain substitutions which may affect protein stability, there is no known way of identifying which sites in the protein will lead to stabilization when substituted. For example, it has been suggested that protein stability would be increased if alanine were substituted for glycine or serine; or if threonine were substituted for serine (Matthews, B. W., et al. (1987) Proc. Natl. Acad. Sci. 84:6663–6667); or if proline were substituted for glycine. However, the sites in which one or more of these substitutions should be made has been so far unpredictable. Other methods depend on comparisons of the amino acid sequences of different but related proteins. However, this does not show which sites are important to stability, only which positions are different.

There are two computer based methods for identifying the sites which affect the stability of a protein according to the invention.

In the first method for identifying sites which affect the stability of protein, the first step comprises generating a probe-accessible surface by analyzing the target protein coordinates with an uncharged probe molecule having a radius of about 0.9 to about 2.0 Å. It is important that no water molecules be included in the protein structure during this analysis. The second step of this method is the identification of the amino acids which form the boundaries of the internal cavities. These amino acids comprise a set of positions which, if mutated, may increase the stability of the protein. An increase in stability can be achieved by amino acid substitutions which decrease the volume of the internal cavities.

The molecular modeling program QUANTA (trademark of Polygen Corporation, 200 Fifth Ave., Waltham, Mass. 02254) was used to calculate probe-accessible surfaces as well as perform the alignment of the three dimensional coordinates of the proteins. These functions can be carried out equally well by other molecular modeling programs which are also commercially available. The following is a list of commercially available programs which can also be used to calculate probe-accessible surfaces: Insight or InsightII (trademark of Biosym Technologies, Inc., 10065 Barnes Canyon Road - Suite A, San Diego, Calif. 92121), BIOGRAF (trademark of Biodesign, Inc., 199 S. Los Robles Ave., #270, Pasadena, Calif. 91101) or Sybyl (trademark of Tripos Associates, 1699 S. Hanley Road, St. Louis, Mo. 63144) The probe-accessible surface referred to in step 1 of the first method can be generated in several ways (Richards, F. M. (1977) Annu. Rev. Biophys. Bioeng. 6:151–176): A spherical probe of radius R (0.9 to 2.0 Å) is allowed to roll on the outside of a molecule while maintaining contact with the van der Waal surface. The surface defined by the center of the probe is defined as the probe-accessible surface. Alternatively, a similar surf ace can be generated by increasing the van der Waal radii of all the atoms in a protein by the radius of the probe. Overlapping surfaces are eliminated and the remaining surface represents the probe-accessible surface. In the preferred embodiment, a three-dimensional box of dimensions 50×50×50 Å with a 1 Å grid size in all three dimensions (x, y, and z) is centered on the center of mass of the target protein coordinates. Most preferrably, the dimensions of the probe map are adjusted such that all of the protein atoms fall within the probe map's bounds. The grid size of 1 Å provides a sufficiently high resolution to clearly define the probe-accessible surface although another grid size could be used, ranging from 0.5 to 3.0 Å. An uncharged probe molecule is positioned at each grid point and the energy of interaction between the probe and the target protein atoms is determined. The energy of nonbonded interaction ($E_{nb}$) contains only the van der Waal component such that $$E_{nb} = \sum_{\substack{nonbonded \\ i,j\ pairs}} 4\varepsilon_{ij}\left[\left(\frac{\sigma_{ij}}{r}\right)^{12} - \left(\frac{\sigma_{ij}}{r}\right)^{6}\right] \qquad \text{EQUATION (1)}$$

where r is the nonbonded distance, $\epsilon_{ij}$ is the dispersion well depth and $\sigma_{ij}$ is the Lennard-Jones diameter. The result is a map consisting of a box with energy values at each grid point. This map can be contoured at a particular energy value to generate surfaces which correspond to the solvent accessible surface and internal cavities (Goodford, P. J. (1985) J. Med. Chem. 28:849–857). The value at which to contour the maps can vary depending on the particular radius used and the parameters used to define the probe molecule and the particular method used to generate the probe. The preferred embodiment is to used a probe radius of 0.9 Å and contour the surface at 10 kcal/mol.

The external surface of the probe-accessible surface is also known as the solvent-accessible surface. Probe-accessible surfaces inside of the solvent accessible surface are defined as internal cavities and represent cavities large enough to accommodate a molecule with a radius equal to the probe radius. The presence of such a cavity on the inside of a protein does not imply that the cavity will in fact be filled by one or more solvent molecules.

The second step of the method for identifying sites which affect the stability of a protein is the identification of the amino acids which form the internal cavities. The internal cavities are defined by the amino acids which make up its boundaries. These amino acids comprise a set of positions which, if mutated, may increase the stability of the protein.

In a second method for identifying sites which affect the stability of a protein, the first step comprises generating a probe-accessible surface by analyzing the target protein coordinates with an uncharged probe molecule having a radius of about 0.9 to about 2.0 Å. It is important that no water molecules be included in the protein structure during this analysis. This step is the same as the first step of the method set forth above.

The second step involves aligning the three dimensional structure of the target protein and a reference protein by moving the three dimensional coordinates of the reference protein into the coordinate frame of the target protein. The reference protein is usually chosen so that a high degree of similarity exists between it and the target protein so that packing differences between the target and reference protein which potentially affect the stability of the target protein can be identified. The reference protein can be any protein for which a three dimensional structure is available which is homologous to the target protein. Examples of such proetins include but are not limited to subtilisin Carlsberg, subtilisin BPN', proteinase K, and Thermitase. When the target protein is BLAP, one preferred reference protein is Thermitase. Thermitase is an extra-cellular subtilisin-like serine protease isolated from *Thermoactinomyces vulgaris* (Frömmel, C., et al. (1978) Acta Biol. Med. Ger. 37:1193–1204). The protein amino acid sequence of thermitase is 42% identical to BLAP. The high degree of similarity between these two proteins provides an ideal system with which to examine packing differences that affect BLAP stability. In this second step the three dimensional structures of Thermitase and BLAP are aligned using the computer program QUANTA™. The three dimensional alignment is carried out by first aligning the primary sequences of the two proteins to determine which amino acids are equivalent. This is accomplished using FASTA (Myers, E. W., and Miller, W. (1988) Comput. Applic. Biosci. 4:11–17; Pearson, W. R., and Lipman, D. J. (1988) Proc. Natl. Acad. Sci. USA 85:2444–2448). Based on this alignment of the primary sequence, residues are matched for subsequent alignment of the three dimensional structures using MULTLSQ (Sutcliffe, M. J., et al. (1987) Protein Eng. 1:377–384; Kabsch, W. (1976) Acta Cryst. A32:922–923). This program uses one structure as fixed coordinates (the target protein coordinates) and then rotates and translates a second structure (the reference protein coordinates) so as to give the smallest root mean squared (r.m.s.) deviation between the two sets of three dimensional coordinates. For example, the alignment of the BLAP and thermitase three dimensional coordinates results in an r.m.s. deviation between equivalent a-carbons of 0.8 Å. This demonstrates that the amino acid sequences of BLAP and thermitase fold into three dimensional structures which are extremely similar.

In the third step, the alignment of the three dimensional structures is used to identify sites which affect the stability of the target protein. This can be accomplished by a variety of methods. Using a computer program designed to display protein structures and surfaces such as QUANTA™, the structure of the reference protein can be displayed with the probe-accessible surface. The combined display of the reference protein and probe-accessible surface can then be visually examined to determine which amino acids in the reference protein fall outside of the solvent-accessible surface or inside internal cavities. An alternative method which can be used comprises coloring the atoms of the reference protein by determining whether amino acids in the reference protein fall outside of the solvent-accessible surface or inside internal cavities. The probe-accessible surface map (probe map) was used to color the atoms in the transformed subtilisin BPN' structure. In order to color each atom, an energy value needs to be interpolated from the probe map at each atomic coordinate.

The probe map consists of three dimensional grid with an energy value (E) at each grid point. In the preferred embodiment, the probe map is a 50×50×50 Å box centered on the center of mass of the protein with a 1 Å grid unit in all three dimensions (x, y, and z). In its optimal conception, the size of the probe map is adjusted such that all of the protein atoms fall within the probe map's bounds. The energy value at each protein atom position was approximated by interpolating from the energy values from the surrounded eight grid points in the probe map. Given the energy value at each point from the probe map, the grid spacing, and the atomic coordinate, it is a simple matter for any one skilled in the art to interpolate an energy value at each atomic coordinate.

In one such method, an energy value of zero is assigned arbitrarily if an atom falls outside the bounds of the map. From a given atomic coordinate (x,y,z), the eight closest grid points from the probe map which surround (X,Y,Z) are identified such that $(x_1<x<x_2)$, $(y_1<y<y_2)$, and $(z_1<z<z_2)$. The eight grid points are then A $(x_1, y_1, z_1)$, B $(x_1, y_1, z_2)$, C $(x_1, y_2, z_2)$, D $(x_1, y_2, z_1)$, E $(x_2, y_1, z_1)$, F $(x_2, y_1, z_2)$, G $(x_2, y_2, z_2)$, and H $(x_2, y_2, z_1)$. The energy value (E) at a given grid point such as $(x_1, y_1, z_1)$ is then $E(x_1,y_1,z_1)$ or equivalently $E_A$. The energy at a specific atomic coordinate $E_{((x,y,z)}$ can be interpolated from the probe map given the eight nearest surrounding grid points (A through H, as described above) and the value at each grid point ($E_A$ through $E_H$). The equation which was used for calculating the energy at specific atomic coordinates, $E_{(x,y,z)}$ is shown in Equation (2). The energy value at each coordinate can then be stored and used to display the molecule.

$$E_{(x,y,z)} = \left(\frac{x-x_1}{x_2-x_1}\right)(E_o - E_k) + E_k \quad \text{EQUATION (2)}$$

where $$E_o = \left(\frac{y-y_1}{y_2-y_1}\right)(E_m - E_l) + E_l; \text{ and}$$

$$E_k = \left(\frac{y-y_1}{y_2-y_1}\right)(E_j - E_i) + E_i;$$

and where $$E_i = \left(\frac{z-z_1}{z_2-z_1}\right)(E_F - E_E) + E_E;$$

$$E_j = \left(\frac{z-z_1}{z_2-z_1}\right)(E_G - E_H) + E_H;$$

$$E_l = \left(\frac{z-z_1}{z_2-z_1}\right)(E_B - E_A) + E_A;$$

$$E_m = \left(\frac{z-z_1}{z_2-z_1}\right)(E_C - E_D) + E_D;$$

The protein atoms were colored on the basis of this interpolated energy value. The protein was displayed using QUANTA™ and atoms with interpolated energies below 10 kcal/mol were colored as red. Atoms with interpolated energies above 10 kcal/mol were colored green. Visual inspection allowed identification of side chains which penetrated the solvent accessible surface or penetrated internal cavities.

There are also two computer based methods for increasing the stability of a protein. The first method comprises the steps of: (1) generating a probe-accessible surface of said target protein by probing the coordinates of said protein with an uncharged probe molecule having a radius of about 0.9 to about 2.0 Å, wherein said probe-accessible surface has an external surface the interior of which contains one or more probe-accessible internal cavities; (2) identifying the amino acids which make up the boundaries of the internal cavities, wherein said amino acids comprise a set of sites which when mutated increase the stability of the protein; (3) identifying an amino acid mutation which would decrease the volume of said internal cavities; (4) determining if said amino acid in said target protein can be changed without creating unacceptable steric interactions; (5) replacing the amino acid in said target protein by site-directed mutagenesis of the gene which expresses said target protein.

The first two steps of the above first method for improving the stability of a protein are the same as those disclosed above for the first computer based method for identifying the sites which affect the stability of a protein.

In step (3) an amino acid identified in step (2) is examined with the goal of identifying a mutation which would decrease the volume of said internal cavity. The size, shape and position of said internal cavity often defines and limits what mutations are acceptable and allowable given the distinct shape and size of each individual amino acid side chain. However, as a particular site in the protein has been identified for mutation, appropriate mutations can be also be determined by applying any of the various heuristics which define generally acceptable mutations (Matthews, B. W., et al. (1987) Proc. Natl. Acad. Sci. 84:6663–6667; Menéndez-Arias, L., and Argos, P. (1990) J. Mol. Biol. 206:397–406; Sandberg, W. S., and Terwilliger, T. C. (1991) Trends Biotechnol. 9:59–63; Bordo, D., and Argos, P. (1991) J. Mol. Biol. 217:721–729).

In step (4) a determination is then made if the amino acid identified for change in the target protein can be mutated or changed without creating a conformation of the target protein having unacceptable steric interactions. The separation distance between two atoms considered unacceptably short is some percentage of the sum of the van der Waal radii of the two atoms in question. Values of 90– 95% of the sum of the van der Waal radii are common though others could be used. Common atoms between the original and replacement amino acid side chain are located and fixed in the same position. The new amino acid is rotated to find the position with the least number of close contacts or unacceptable steric interactions (distances shorter than physically reasonable). The separation distance at which two atoms are considered unreasonably short is some percentage of the sum of the van der Waal radii of the two atoms in question. Values of 90–95% of the sum of the van der Waal radii are common though others could be used. If all conformations of the new amino acid have close contacts, the amino acid substitution is rejected. A conformation with no close contacts which can be matched to a preferred amino acid conformation as defined by Ponder, J. W., and Richards, F. M. (1987) J. Mol. Biol. 193:775–791, is most highly desirable. In step (6) the amino acid identified for change to the corresponding amino acid in the same position in the reference protein is changed by site-directed mutagenesis of the gene which expresses the target protein by the methods disclosed above.

The second method comprises the steps of: (1) generating a probe-accessible surface of said target protein by probing the three dimensional coordinates of said protein with an uncharged probe molecule having a radius of about 0.9 to about 2.0 Å, wherein said probe-accessible surface has an external surface the interior of which contains one or more probe-accessible internal cavities; (2) aligning said three dimensional coordinates of said target protein and a reference protein by moving the three dimensional coordinates of said reference protein into the coordinate frame of said target protein; (3) identifying an amino acid in said reference protein whose side chain lies outside said solvent-accessible surface of said protein or inside said internal cavities of said target protein; (4) identifying the amino acid in said target protein which occupies the equivalent position as said amino acid in said reference protein; (5) determining if said amino acid in said target protein can be changed without creating unacceptable steric effects; (6) replacing the amino acid in said target protein with the corresponding amino acid in the equivalent position in said reference protein by site-directed mutagenesis of the gene which expresses said target protein.

The first three steps of this method are the same as steps (1), (2), and (3) of the second method for the second computer based method for identifying the sites which affect the stability of a protein.

In step (4) the amino acid in the target protein which occupies the equivalent position as the amino acid in the reference protein is identified. Equivalency is determined from the primary sequence alignment and three dimensional structure alignment described above. Given two protein structures, a target and a reference structure, which have been aligned, equivalent amino acids are defined as pairs of amino acids, one from the target and one from the reference protein, which may differ in identity but occupy close to the same position in the secondary and tertiary structure of the two proteins.

The following examples are meant to illustrate but not to limit the invention.

EXAMPLE 1

Identification of sites in BLAP for mutagenesis

The structure of BLAP was obtained by X-ray crystallography and solved to 1.4 Å. The atomic coordinates are shown in FIG. 1. Water molecules were removed from the structure and the protein coordinates were used to generate a probe-accessible surface using a computer program QUANTA™ (version 3.0). This program can be used to calculate a probe-interaction map. The coordinates of BLAP were read into the computer and the following parameters were set in order to perform the probe interaction grid calculation. A Van der Waal calculation was requested with a "proton" probe (radius of 0.9 Å) with a charge of 0.0. The box dimensions were set to 50 Å with a grid size of 1 Å centered on the α-carbon of residue 219. The maximum energy was set to 500 and the minimum to –100. This means that energy values which exceed 500 will be set to 500. An energy value will exceed 500 when the probe is very close to an atom in the protein. The calculations were performed on a Silicon Graphics Inc. (2105 Landings Drive, Suite 2105, Mountain View, Calif. 94043) 4D/220 PowerIris™ workstation. QUANTA™ was used to visualize the probe-accessible surface. The map was contoured at 50 kcal/mol but this value depends on the particular constants in use and the method used to generate the probe accessible surface. The map was displayed simultaneously with the structure of BLAP and amino acid side chains which defined the boundaries of the internal cavities were identified visually.

One such amino acid was threonine-69. This side chain is completely buried with only 2% of its surface being solvent accessible. The hydroxyl group of the side chain defined part of the border of two internal cavities. These particular cavities are occupied by water molecules 278 on one side, and 280 on the other. Mutating this amino acid to valine represents a conservative change which increases the hydrophobicity of the side chain while having little effect on size and shape. Using computer modeling, it was determined that mutating threonine-69 to valine would not create any close contacts with other protein atoms or significantly perturb the structure if the valine occupies the same position as the hydroxyl of threonine-69 in the wild type protein. An oligonucleotide was synthesized which carried a mutation of the codon for threonine-69 to valine (T69V). This oligonucleotide was used to create a site directed mutation in the BLAP gene which was subcloned into a Bacillus vector and expressed in B. subtilis DB104 (See Examples 4 and 5). Strains were identified which were expressing the mutant protease and several shake flasks were prepared to produce the mutant protein (See Example 5). The mutant protease was purified from the shake flask media and characterized for surfactant and temperature stability (See Examples 7, 10, and 11).

The mutation T69V resulted in a 340% increase in the half-life of the protease at 50° C., from 12 minutes to 41 minutes (See Table 3).

sional grid of (x, y, z) coordinates in space and an energy value at each position, was read into computer memory along with the protein coordinates (the transformed 1CSE structure). The energy value at each atom position was approximated by interpolating from the energy values of the surrounding eight nearest grid points in the probe map. The protein atoms were colored on the basis of this interpolated energy value. The protein was displayed using QUANTA™ and atoms were displayed in different colors depending on their interpolated energy value. For example, if the energy were greater than 400 the atoms were dark blue; between 300 and 400, light blue; 200 and 300, green; 200 to 100 yellow; and between –100 and 100, red. Visual inspection of such a display allowed identification of side chains which penetrated the solvent accessible surface or internal cavities.

One such amino acid was methionine-199 (1CSE numbering) in subtilisin Carlsberg. The amino acid was identified by visual inspection of the transformed 1CSE structure (as described above). Below, the coordinates of residue 199 from the transformed 1CSE structure are shown in the Brookhaven Protein Data Bank file format along with the interpolated energy values.

| | | | | | | | | | |
|---|---|---|---|---|---|---|---|---|---|
| \multicolumn{10}{c}{Coordinates of Methionine-199 from the 1.2 Å structure of subtilisin Carlsberg.} |
| ATOM | 1364 | N | MET | 199 | 22.392 | 40.705 | 32.311 | 1.0 | 500.00 |
| ATOM | 1365 | CA | MET | 199 | 21.675 | 40.581 | 31.054 | 1.0 | 500.00 |
| ATOM | 1366 | C | MET | 199 | 22.438 | 39.677 | 30.103 | 1.0 | 500.00 |
| ATOM | 1367 | O | MET | 199 | 23.689 | 39.601 | 30.254 | 1.0 | 500.00 |
| ATOM | 1368 | CB | MET | 199 | 21.621 | 41.991 | 30.511 | 1.0 | 500.00 |
| ATOM | 1369 | CG | MET | 199 | 20.868 | 42.994 | 31.426 | 1.0 | 500.00 |
| ATOM | 1370 | SD | MET | 199 | 19.150 | 42.631 | 31.891 | 1.0 | 211.58 |
| ATOM | 1371 | CE | MET | 199 | 18.273 | 43.395 | 30.493 | 1.0 | 41.68 |

EXAMPLE 2

Identification of sites in BLAP for mutagenesis based on other proteases.

(A) Comparison to subtilisin Carlsberg.

The three dimensional coordinates of subtilisin Carlsberg (1CSE) were obtained from the Brookhaven Protein Database (Bernstein, F. C., et al. (1977) J. Mol. Biol. 112:535–542). The protease structures were aligned using the molecular modeling program QUANTA™. The BLAP coordinates were held fixed. The α-carbons of residues 1 to 32 of BLAP were matched to residues 1 to 32 of 1CSE, respectively; residues 40 to 60 of BLAP to residues 41 to 61 of 1CSE; residues 80 to 155 of BLAP to residues 82 to 157 of 1CSE; residues 170 to 269 of BLAP to residues 176 to 275 of 1CSE. The BLAP structure was held fixed, and the 1CSE structure was rotated and translated such that the r.m.s. deviation between the α-carbons of matched residues was minimized. The translation vector (–10.68738, 31.28904, –5.32134) and the rotation matrix

| | | |
|---|---|---|
| (0.17406 | –0.65535 | 0.73500 |
| –0.42119 | –0.72422 | –0.54599 |
| 0.89011 | –0.21454 | –0.40209) | were applied to the coordinates of 1CSE and the transformed coordinates were saved (henceforth, the transformed 1CSE structure). The final r.m.s. deviation between the matched 229 α-carbon pairs was 0.872 Å.

The probe-accessible surface map calculated in Example 1 was used to color the atoms in the transformed 1CSE structure. The entire map, which consists of three dimen- Column 1 is the record type; column 2 is the atom number; column 3 is the atom name; column 4 is the residue name; column 5 is the residue number; columns 6, 7 & 8 are the x, y, z coordinates of the atom, respectively; column 9 is the occupancy; column 10 is normally the temperature factor but this has been replaced with the interpolated energy value. Note that a value of 500 in this column means that the atom in nearly completely within the van der Waal surface of the BLAP molecule. When the probe map was calculated (see Example 1), energy values greater than 500 were set to 500. As can be seen, atoms 1370 and 1371 have significantly lower energy values (column 10). The end of this methionine residue extends into an internal cavity in the BLAP molecule.

This residue is equivalent in secondary and tertiary structure to valine-193 in BLAP. Using computer modeling, valine-193 in BLAP was changed to methionine. The X values for the new methionine side chain in BLAP were taken from the subtilisin BPN' structure. In this conformation, the new side chain had no close contacts except for the ε-carbon of the methionine which contacted a crystallographic water in the BLAP structure.

An oligonucleotide was synthesized which mutated the codon for valine-193 to methionine (V193M) in the BLAP gene. This oligonucleotide was used to create a site directed mutation in the BLAP gene which was subcloned into a Bacillus vector and expressed in B. subtilis DB104 (See Examples 3, 4, and 5). Strains were identified which were expressing the mutant protease and several shake flasks were prepared to produce the mutant protein (See Example 5). The mutant protease was purified from the shake flask media and characterized for temperature and surfactant stability (See Examples 6, 7, 10, and 11).

The mutation V193M resulted in a 350% increase in the half-life of the protease at 50° C., from 12 minutes to 42 minutes (See Table 3).

(B) Comparison to Thermitase.

The three-dimensional coordinates of thermitase (1TEC) were obtained from the Brookhaven Protein Database (Bernstein, F. C., et al. (1977) J. Mol. Biol. 112:535–542).

between −100 and 100, red. Visual inspection of such a display allowed identification of side chains which penetrated the solvent accessible surface or internal cavities.

One such amino acid was tyrosine-149 (1TEC numbering) in thermitase. The amino acid was identified by visual inspection of the transformed 1TEC structure. Below, the coordinates of residue 149 from the transformed 1TEC structure are shown in the Brookhaven Protein Data Bank file format along with the interpolated energy values.

| | | | | | | | | | |
|---|---|---|---|---|---|---|---|---|---|
| \multicolumn{10}{c}{Coordinates of Tyrosine-149 from the 2.0 Å structure of Thermitase.} |
| ATOM | 1052 | N   | TYR | 149 | 19.783 | 23.026 | 47.326 | 1.0 | 500.00 |
| ATOM | 1053 | CA  | TYR | 149 | 20.372 | 21.668 | 47.275 | 1.0 | 500.00 |
| ATOM | 1054 | C   | TYR | 149 | 21.456 | 21.557 | 46.165 | 1.0 | 500.00 |
| ATOM | 1055 | O   | TYR | 149 | 22.619 | 21.330 | 46.486 | 1.0 | 500.00 |
| ATOM | 1056 | CB  | TYR | 149 | 19.282 | 20.595 | 47.169 | 1.0 | 500.00 |
| ATOM | 1057 | CG  | TYR | 149 | 19.859 | 19.183 | 46.935 | 1.0 | 227.30 |
| ATOM | 1058 | CD1 | TYR | 149 | 20.262 | 18.427 | 48.038 | 1.0 | 79.13 |
| ATOM | 1059 | CD2 | TYR | 149 | 20.014 | 18.722 | 45.608 | 1.0 | 275.01 |
| ATOM | 1060 | CE1 | TYR | 149 | 20.762 | 17.146 | 47.807 | 1.0 | 10.99 |
| ATOM | 1061 | CE2 | TYR | 149 | 20.531 | 17.425 | 45.371 | 1.0 | 500.00 |
| ATOM | 1062 | CZ  | TYR | 149 | 20.860 | 16.649 | 46.488 | 1.0 | 131.28 |
| ATOM | 1063 | OH  | TYR | 149 | 21.165 | 15.337 | 46.282 | 1.0 | 147.29 |

The structures of BLAP and 1TEC were aligned using the molecular modeling program QUANTA™ by matching equivalent α-carbons as listed below.

| Matched α-carbons between BLAP and Thermitase (1TEC) | |
|---|---|
| BLAP | 1TEC |
| 5–20 | 12–27 |
| 23–34 | 29–41 |
| 43–72 | 52–81 |
| 75–227 | 85–237 |
| 232–256 | 240–264 |

The BLAP structure was held fixed and the 1TEC structure was rotated and translated such that the r.m.s. deviation between the α-carbons of matched residues was minimized. The translation vector (14.92521, 33.43270, 40.92134) and the rotation matrix

| | | |
|---|---|---|
| (0.79048 | −0.20395 | −0.57753 |
| −0.01688 | 0.93532 | −0.35340 |
| 0.61225 | 0.28911 | 0.73591) | were applied to the coordinates of 1TEC and the transformed coordinates were saved (henceforth, the transformed 1TEC structure). The final r.m.s. deviation between the matched 236 α-carbon pairs was 1.384 Å.

The probe-accessible surface map was used to color the atoms in the transformed 1TEC structure. The entire probe map was read into computer memory along with the coordinates of the transformed 1TEC structure. The energy value at each atomic position was interpolated from the energy values of the eight surrounding grid points in the probe map. The protein was displayed using QUANTA™ and atoms were displayed in different colors as a function of their interpolated energy value. For example, if the energy were greater than 400 the atoms were dark blue; between 300 and 400, light blue; 200 and 300, green; 200 to 100 yellow; and Column 10 is normally the temperature factor but this has been replaced with the interpolated energy value. As can be seen, the phenyl ring of the tyrosine side chain has significantly lower energy values (column 10 of atoms CG, CD1, CD2, CE1, CE2 and CZ).

This residue is equivalent in secondary and tertiary structure to serine-139 in BLAP. Using computer modeling, serine-139 in BLAP was changed to tyrosine. The X values for the new tyrosine side chain in BLAP were taken from the thermitase structure. In this conformation, the new side chain had no close contacts that could not be alleviated by small changes (less than 5°) of the X values. The modeled tyrosine side chain in BLAP fits neatly into a crevice on the surface of the BLAP protein between two surface helices.

An oligonucleotide was synthesized which mutated the codon for serine-139 to tyrosine (S139Y) in the BLAP gene. This oligonucleotide was used to create a site directed mutation in the BLAP gene which was subcloned into a Bacillus vector and expressed in B. subtilis DB104 (See Examples 3, 4, and 5). Strains were identified which expressed the mutant protease and several shake flasks were prepared to produce the mutant protein (See Example 5). The mutant protease was purified from the shake flask culture and characterized for temperature and surfactant stability (See Examples 6, 7, 10, and 11).

The mutation S139Y resulted in a 216% increase in the half-life of the protease at 50° C., from 12 minutes to 26 minutes (See Table 3).

EXAMPLE 3

Site Directed Mutagenesis of the BLAP gene

This mutagenesis procedure was first described by Stanssens, P., et al. (1989) Nucleic Acids Res. 17:4441–4454. While this is the preferred method, many other methods could be used to introduce oligonucleotide site-directed mutations, particularly those which use single stranded DNA. For example, the method of Kunkel (Kunkel, T. A. (1985) Proc. Natl. Acad. Sci. USA 82:488–492) has also been used.

A synthetic oligonucleotide was synthesized which mutates the codon of threonine-69 to the codon for valine.

The mutagenic oligonucleotide was annealed to a gapped duplex DNA which carries the BLAP gene on a segment of single stranded (ss) DNA. The gapped duplex (gd) was formed by denaturing linear DNA's from pMc13C and pMa5-8 followed by re-annealing. The mutagenic oligonucleotide annealed to homologous ss BLAP DNA within the gap and the remaining gap was filled in by a DNA polymerase and ligated using T4 DNA ligase. Subsequent treatment of the product of the fill-in reaction with ExoIII removed any species with only partially filled gaps.

The product of the fill-in reaction was then transformed into a repair deficient *E. coli* strain such as WK6mutS. Plasmid DNA from the recombinant *E. coli* WK6mutS was prepared and transformed in a low plasmid/recipient ratio into a suppressor deficient strain of *E. coli* such as WK6. Ampicillin resistant transformants were selected and plasmid DNA of several candidates was purified and checked for the presence of the mutation.

The mutant BLAP protease was expressed by transferring the mutant BLAP genes from their particular *E. coli* pMa13C derivative vector into a plasmid vector which can replicate in Bacillus such as pH70 or pC51. In the following example, the plasmids pC51 and pH70 can be used interchangeably with the exception that plasmid pH70 encodes resistance to kanamycin while plasmid pC51 encodes resistance to tetracycline. The mutant BLAP gene was separated from the pMa13C plasmids by digestion with the restriction endonucleases AvaI and SstI and then ligated with an AvaI-SstI cut fragment of plasmid pH70 that includes the regions necessary for kanamycin resistance and for replication in Bacillus. The pH70 AvaI-SstI fragment was purified by high pressure liquid chromatography (HPLC). After ligation the mutant BLAP plasmids were transformed into *B. subtilis* DB104, a strain that has been engineered to inactivate its own genes encoding the major alkaline and neutral proteases. *B. subtilis* DB104 transformed by these plasmids were grown on a nutrient-skim milk agar in the presence of the antibiotic kanamycin. Clones that manufactured mutant protease were identified by the formation of clear zones of hydrolysis in the skim milk. Plasmid DNA was purified from these clones to verify that the protease-producing clones carried the a plasmid-borne BLAP gene with the desired mutation. The plasmid DNA was purified away from cell protein and chromosomal DNA by SDS-salt precipitation followed by chromatography over a Qiagen ion-exchange column (Qiagen Corporation). AvaI-SstI digested plasmid DNAs from different clones were compared with AvaI/SstI-digested derivatives of plasmid pH70 known to carry an intact BLAP gene. Plasmid digests were compared by agarose gel electrophoresis to identify plasmids that have the proper-sized AvaI/SstI DNA fragments. Selected plasmid DNAs were then sequenced across the region of the particular BLAP mutation to confirm that the mutation was present. One or more clones of each BLAP mutation were stored frozen in 15% glycerol at −70° C. and also cultivated in shake flasks (Examples 4 and 5) to manufacture mutant protease for characterization.

EXAMPLE 4

Production of Proteases

Each strain of *B. subtilis* DB104 that carried a plasmid with one of the mutant BLAP genes was cultivated in shake flasks to make the mutant protease. Strains were grown in 50 ml precultures of (Difco) Luria Broth (LB) with the antibiotic kanamycin for pH70 derived clones or tetracycline for pC51 derived clones at 37° C. and 280 rpm in a New Brunswick Series 25 Incubator Shaker. After 7 to 8 hours of incubation 2.5 or 5.0 ml of the preculture was transferred to 50 or 100 μl of MLBSP medium (Table 5), respectively, with either 20 μg/ml of kanamycin, or 15 μg/ml of tetracycline in 500 ml (Bellco) baffled shake flasks for growth and eventual production of the protease. These main shake flask cultures were incubated at 240 rpm and 37° C. for 64 hours before the culture broths were treated to remove intact cells and cellular debris, and to reduce the pH to 5.8 before they were concentrated. The protease production of each culture was monitored by electrophoresis of culture supernatants with reverse polarity on 12.5% homogenous polyacrylamide gels with the Pharmacia PhastSystem.

EXAMPLE 5

Production of Mutant Proteases in Shake Flasks

A hot loop was used to streak each mutant strain from a frozen cryovial culture onto an LB-skim milk agar containing either 20 μg/ml of kanamycin or 15 μg/ml of tetracycline. The plates were incubated at 37° C. for 20 to 24 hours. A single, isolated colony producing a good zone of hydrolysis of the skim milk was picked into a 250 ml Erlenmeyer flask containing about 50 ml Luria Broth (LB) which contained either 20 μg/ml kanamycin or 15 μg/ml of tetracycline. The broth was incubated in a New Brunswick Series 25 Incubator Shaker at 37° C. with shaking at 280 rpm for 7 to 8 hours. Either 2.5 ml of the turbid preculture was transferred into 50 ml of MLBSP containing either 20 μg/ml kanamycin or 15 μg/ml of tetracycline in each of four baffled 500 ml flasks, or 5 ml of preculture was used as an inoculum for 100 ml of MLBSP broth with antibiotic contained in each of two 500 ml baffled flasks (a 5% v/v transfer). All flasks were incubated at 240 rpm and 37° C. for 64 hours. After 64 hours of incubation the set of flasks for each culture was consolidated, transferred to 50 ml centrifuge tubes, and centrifuged at 20,000 $g_{av}$ for 15 minutes at 4° C. The broth was filtered through Miracloth (Calbiochem Corp. #475855) into 400 ml beakers chilled on ice. The broth was slowly stirred on ice for 30 minutes before the broth pH was reduced to 5.8 by the slow addition of glacial acetic acid. More fine debris were removed by centrifugation again at 20,000 $g_{av}$ and the broth was filtered through Miracloth into graduated cylinders to measure the volume. Two sets of 1 ml samples were made for PhastSystem gels and activity assays. The broth was stored on ice until the protease could be purified. The MLBSP media used for the production of BLAP in shake flask cultures is described in Table 5.

TABLE 5

COMPOSITION OF MLBSP MEDIUM

| Component | Quantity (for 1 liter of media) |
| --- | --- |
| deionized water | 750 ml |
| Difco Casitone | 10 gm |
| Difco Tryptone | 20 gm |
| Difco Yeast Extract | 10 gm |
| NaCl | 5 gm |
| Sodium Succinate | 27 gm |

The media was adjusted to pH of 7.2 by addition of NaOH, the volume adjusted to 815 ml with water and autoclaved 15 minutes at 121° C. at 15 lbs/in². The media was cooled before adding the sterile stock solutions described in Appendix 1, while stirring.

APPENDIX 1

(additions to MLBSP broth)

| Component | | Quantity (for 1 L of media) |
|---|---|---|
| MgSO$_4$.7H$_2$O | (100 mg/ml stock, autoclaved) | 1.0 ml |
| CaCl$_2$.2H$_2$O | (30 mg/ml stock, autoclaved) | 2.5 ml |
| FeSO$_4$.7H$_2$O | (1mM stock, filter sterilized) | 0.5 ml |
| MnCl$_2$.4H$_2$O | (1mM stock, autoclaved) | 0.5 ml |
| Glucose | (25% (w/v) stock, autoclaved) | 80.0 ml |
| PIPES Buffer[1] | (pH 7.2, 1M stock, autoclaved) | 50.0 ml |
| KPO$_4$ Buffer[2] | (1.5M stock, autoclaved) | 50.0 ml |

[1]Piperazine-N,N'-bis(2-ethane sulfonic acid).
[2]A sufficient amount of 1.5M dibasic phosphate (K$_2$HPO$_4$) was added to 200 ml of 1.5M monobasic phosphate (KH$_2$PO$_4$) to adjust the pH to 6.0 using a Beckman pHI44 pH meter equipped with a Beckman combination electrode (#3952C). The final pH was adjusted to 7.0 with 4M KOH.

Either kanamycin or tetracycline antibiotic stock solutions were added to the media just before use to a final concentration of 20 μg/ml and 15 μg/ml respectively.

EXAMPLE 6

Purification of BLAP

Fermentation broth of transformed *B. subtilis* DB104, while still in the fermenter, was adjusted to pH 5.8 with 4 N H$_2$SO$_4$. The broth was collected and cooled to 4° C. If not mentioned otherwise, all subsequent steps were performed on ice or at 4° C. An aliquot of the broth material was clarified by centrifugation at 15,000×g$_{av}$ for 60 min. Floating lipid material was removed by aspiration, and the supernatant filtered through Miracloth. The dark brown solution was placed in dialysis tubing (Spectrapor; #1, 6 to 8 kilodalton (kDa) molecular-weight-cut-off, 1.7 ml/cm) and dialyzed for 16 hours in 20 mM 2-(N-morpholino) ethanesulfonic acid (MES) containing 1 mm CaCl$_2$, adjusted with NaOH to pH 5.8 ('MES buffer'). The dialysate was clarified by centrifugation (20,000×g$_{av}$ for 10 min) and the pH of the solution was adjusted to 7.8 with 2 N NaOH. The enzyme solution containing approximately 0.9 g of protein in 1.2 liter was loaded at a flow rate of 150 ml/hour onto a column of S-Sepharose Fast Flow (SSFF, Pharmacia; 25 mm diameter, 260 mm long) previously equilibrated with 20 mM N- (2-hydroxyethyl)piperazine-N'-(2-ethanesulfonic acid) [HEPES], containing 1 mM CaCl$_2$, adjusted with NaOH to pH 7.8 ('HEPES buffer'). After the application of the enzyme solution the column was washed with 2 column volumes (250 ml) of HEPES buffer and then developed at a flow rate of 140 ml/hour with a gradient of 0 to 0.25 M NaCl in 600 ml of HEPES buffer. The gradient eluate was fractionated into 5.2-ml aliquots which were collected into tubes containing 2 ml of 100 mM MES/Na$^+$, pH 5.8. The enzyme eluted between 0.12 and 0.15 M NaCl. Fractions containing the enzyme were pooled and protein was precipitated with ammonium sulfate at 52% of saturation. Solid salt (0.33 g per ml of solution) was added slowly with stirring over a period of 15 min, and stirring was continued for another 15 min. The precipitate was collected by centrifugation, the pellet was dissolved in MES buffer and the protein concentration in the solution was adjusted to 5 to 7 mg/ml. Following dialysis for 16 hours in MES buffer the solution was clarified by centrifugation and the pH of the supernatant was adjusted to 7.2. The protease was purified further by a second cation exchange separation on SSFF. All steps of this procedure were the same as above except that the pH of the HEPES buffer was 7.2 and that the NaCl gradient was from 0 to 0.25 M in 600 ml of HEPES buffer. Protein in pooled fractions was precipitated as above with ammonium sulfate and the enzyme was stored as ammonium sulfate precipitate at −70° C. Prior to use the ammonium sulfate precipitate of the enzyme was dissolved in an appropriate buffer, typically MES buffer, at the desired protein concentration, and dialyzed overnight in the buffer of choice.

EXAMPLE 7

Purification of BLAP Mutants

Fermentation broth from shake flasks, on average 180 ml, was collected and clarified by centrifugation at 20,000×g$_{av}$ for 15 min. The supernatant was placed, with stirring, on ice and after 30 min the pH of the solution was adjusted to 5.8 with glacial acetic acid. If not mentioned otherwise, all subsequent steps were performed on ice or at 4° C. The solution was clarified again by centrifugation (20,000×g$_{av}$ for 15 min) and was concentrated approximately 4-fold by ultrafiltration (Amicon; YM30 membrane). The dark brown solution was placed in dialysis tubing (Spectrapor; #1, 6 to 8 KDa molecular-weight-cut-off, 1.7 ml/cm) and dialyzed for 16 hours in 20 mM HEPES/Na$^+$, pH 7.8, containing 1 mM CaCl$_2$ ('HEPES buffer'). The dialysate was clarified by centrifugation (20,000×g$_{av}$ for 10 min) and the pH of the solution, if necessary, was adjusted to 7.8 with 2 N NaOH. The enzyme solution was loaded at a flow rate of 60 ml/hour onto a column of SSFF (15 mm diameter, 75 mm long), previously equilibrated with HEPES buffer. When all colored by-products were eluted, the column was washed with 50 ml of HEPES buffer. Then, the enzyme was eluted with 0.25 M NaCl in HEPES buffer. Fractions of 1.2 ml were collected into tubes containing 0.5 ml of 100 mM MES/Na$^+$, pH 5.8. Protein content in fractions was monitored either by a UV detector set at 280 nm or by protein assay as described below. Pooled fractions containing protease protein were placed on ice and protein was precipitated with a 5 to 8-fold volume excess of acetone at −20° C. The protein was allowed to precipitate for 6 min, the mixture was centrifuged for 4 min at 6,600×g$_{av}$, the supernatant was discarded, the pellet was briefly exposed to vacuum (water aspirator) to remove most of the acetone, and the pellet was dissolved in 20 mM MES/Na$^+$, pH 5.8, to give an approximate protein concentration of 30 mg/ml. Prior to any assays, the solution was centrifuged in an Eppendorf centrifuge for 3 min at full speed (13,000×g$_{max}$).

EXAMPLE 8

Protein Determination

Protein was determined by a modified biuret method (Gornall, A. G., et al. (1948) J. Biol. Chem. 177:751–766). The protein in a total volume of 500 μl was mixed with 500 μl of biuret reagent and incubated for 10 min at 50° C. The solution was briefly chilled and its absorbance was measured at 540 nm. Typically, a reagent blank and three different protein aliquots in duplicates were measured and the recorded optical densities analyzed by linear regression. Bovine serum albumin (BSA, crystalline; Calbiochem) was used as protein standard. With purified BLAP protein the usefulness of BSA as protein standard in the biuret assay was confirmed. A BLAP sample was exhaustively dialyzed in 1 mM sodium phosphate, pH 5.8, and subsequently lyophilized. A sample of the solid material was weighed, dissolved in 1 mM sodium phosphate, pH 5.8, and used to generate a standard curve for the biuret assay. From the actual difference in phosphate content (Black, M. J., and Jones, M. E. (1983) Anal. Biochem. 135:233–238) of the final protein solution and the nominally 1 mM sodium phosphate solution used to dissolve the protein, the contribution of phosphate to the weight of solid BLAP was estimated and used to correct the standard curve.

EXAMPLE 9

Protease Assays

Two different protease assays were used. With the HPE method protease activity was established at a single concentration of casein (prepared according to Hammarsten; Merck, #2242) as substrate. In the AAPF-pNA assay initial rates of succinyl-L-alanyl-L-alanyl-L-prolyl-L-phenylalanyl-p-nitroanilide (AAPF-pNA; Bachem) supported catalysis were used to determine the kinetic parameters $K_m$, $k_{cat}$, and $k_{cat}/K_m$.

A. HPE Method.

Culture supernatants or solutions of purified proteases were diluted with chilled buffer (10 mM MES/Na$^+$, pH 5.8) to give three different solutions with a protein concentration ratio of 1:3:5. The substrate solution contained 9.6 mg/ml casein, 24 mM Tris, and 0.4% (w/v) sodium tripolyphosphate, dissolved in synthetic tap water (STW; 0.029% (w/v) CaCl$_2$.2H$_2$O, 0.014% (w/v) MgCl$_2$.6H$_2$O, and 0.021% (w/v) NaHCO$_3$ in deionized water) adjusted to pH 8.5 at 50° C., prepared as follows. With stirring for 10 min, 6 g of casein was dissolved in 350 ml of STW. To this, 50 ml of 0.3 M Tris in STW was added and stirring was continued for another 10 min. This solution was heated to 70° C., then allowed to cool slowly. At 50° C., the pH was adjusted to 8.5 with 0.1 N NaOH. When the solution reached room temperature, the volume was adjusted to 500 ml with STW, followed by the addition of 125 ml of 2% (w/v) pentasodium tripolyphosphate in STW, pH 8.5 (adjusted with 3 N HCl). The protease assay was started by adding 50 Al of protease solution to 750 μl of substrate solution placed in a 2.2 ml Eppendorf container preincubated for 10 min at 50° C. After 15 min, the reaction was terminated by the addition of 600 Al of trichloroacetic reagent (0.44 M trichloroacetic acid, 0.22 H sodium acetate in 3% (v/v) glacial acetic acid). The mixture was placed on ice for 15 min, the precipitated protein removed by centrifugation for 8 min (at 13,000×g$_{max}$.) and a 900 μl aliquot of the supernatant was mixed with 600 μl of 2 N NaOH. The absorbance at 290 nm of this solution was recorded. Each dilution was assayed in duplicates and the data points for three different dilutions from one enzyme sample was analyzed by linear regression. A slope of 1 in this assay corresponds to 80 HPE units in the least diluted sample. In case of strongly colored culture supernatants with measurable quantities of UV absorbing material carried over by the diluted protease aliquot into the assay cuvette a control curve was constructed whose slope was subtracted from the slope of the protease assay before final HPE units were calculated.

B. AAPF-PNA Assay

Protease samples were diluted with 50% (v/v) 1,2-propanediol in 100 mM Tris, adjusted with 2 N HCl to pH 8.6 at 25° C. ('Tris-propanediol buffer'), in which they were stable for at least 6 h at room temperature. A stock solution of 160 mM AAPF-PNA was prepared in dimethylsulfoxide dried with a molecular sieve (Aldrich; 4 Å, 4–8 mesh) for at least 24 h prior to use. Fixed point assays were performed at 25° C. with 1.6 mM AAPF-pNA in 100 mM Tris, adjusted with 2 N HCl to pH 8.6 at 25° C., in a total volume of 1.020 ml. The substrate was added to the assay buffer 1 min prior to the assay initiation and the reaction was started by addition of enzyme at a final concentration of 20 ng to 1.3 μg of protein per ml (0.75 to 48.5 nM enzyme) depending on specific activity. Release of p-nitroanilide was monitored at 410 nm, and a molar extinction coefficient of 8,480 M$^{-1}$cm$^{-1}$ was used to calculate amount and concentration of product formed (DelMar, E. G., et al. (1979) Anal. Biochem. 99:316–320). Kinetic parameters were calculated from a velocity vs. substrate concentration plot constructed from initial rates measured once each at 12 different AAPF-pNA concentrations ranging from 0.16 to 3.2 mM. Data were fitted to a hyperbolic curve and proportionally weighted using the program ENZFITTER (Leatherbarrow, R. J. (1987) ENZFITTER, Biosoft, Cambridge, UK). A nominal molecular weight of 26.8 kDa was used in all calculations that required the interconversion of protein concentration and molarity of protease enzyme.

EXAMPLE 10

Temperature Stability of Purified Proteases

Stability of protease proteins was evaluated under two different conditions: (a) 100 mM glycine/Na$^+$, pH 10 at 60° C., and (b) 100 mM glycine/Na$^+$, pH 11 at 50° C. At t=0 min, the protein was diluted to approximately 0.25 mg/ml into incubation buffer maintained at the desired temperature. Periodically, an aliquot was removed from this incubation mixture and diluted into Tris-propanediol buffer chilled on ice. Residual protease activity was determined by the AAPF-pNA assay at a fixed AAPF-pNA concentration (1.6 mM). Stability is expressed as half-life ($t_{1/2}$) of activity determined from semi-logarithmic plots of residual activity as function of time. Each plot consisted of 6 data points with $t_{1/2}$ approximately in the center between experimental points.

EXAMPLE 11

Resistance of Proteases to Sodium Dodecylsulfate (SDS)

SDS was selected as representative of surfactants in general. Resistance of proteases to SDS was evaluated under two different conditions: (a) 100 mM Tris adjusted with 2 N HCl to pH 8.6 at 50° C., containing 1% (w/v) SDS, and (b) 50 mM sodium carbonate, pH 10.5 at 50° C., containing 1% (w/v) SDS. Protease proteins were incubated at a final protein concentration of 0.25 mg/ml. Data were collected and evaluated as described above under Example 10.

EXAMPLE 12

Polyacrylamide Gel Electrophoresis

Purity of protease samples was evaluated on 20% non-denaturing PhastSystem gels (Pharmacia) run with reversed polarity. The same system was used to monitor the protease content of crude shake flask and fermentation broths. Buffer strips were prepared as described in Application File No. 300 (Pharmacia).

Molecular weight determinations were performed on 20% SDS PhastSystem gels, using the following markers: bovine serum albumin, 66 kDa; egg albumin, 45 kDa; glyceraldehyde-phosphate dehydrogenase, 36 kDa; carbonic anhydrase, 29 kDa; trypsinogen, 24 kDa; trypsin inhibitor, 20.1 kDa; α-lactalbumin, 14.2 kDa (all from Sigma). Prior to SDS-PAGE, a protease sample was denatured with formic acid at a final concentration of 30 to 50% (v/v). Upon dilution of formic acid to 15% (v/v) protein was precipitated with trichloroacetic acid at a final concentration of 10% (v/v). The collected pellet was washed once with water, then dissolved in 2% (w/v) SDS and heated for 2 min in a boiling waterbath. Gels were stained with Coomassie Brilliant Blue R-250 (Kodak).

DEPOSIT OF MICROORGANISMS

Living cultures of the following have been accepted for deposit under the Budapest Treaty on the International Recognition of the Deposit of Microorganisms for the purposes of patent procedure by the American Type Culture Collection, 12301 Parklawn Drive, Rockville, Md. 20852 on May 8, 1991 (the accession number preceeds each deposit description): ATCC 68614—*Bacillus licheniformis* ATCC 53926 strain which contains a tetracycline-resistance plasmid originally derived from Bacillus plasmid pBC16 which carries the ATCC 53926 alkaline protease-BLAP ClaI fusion gene, whose structural gene has the mutations S3T, V4I, A188P, V193M, V199I; ATCC 68615—*E. coli* WK6 which carries phasmid pMc13C, a chloramphenicol-resistant derivative of phasmid pMc5-8, that contains the ATCC 53926 alkaline protease- BLAP ClaI fusion gene and a 164 bp KpnI fragment carrying the ATCC 53926 alkaline protease gene's transcriptional terminator. The genotype of strain WK6 are Δlac-proAB, galE, strA, mutS::Tn10/F'lacI$^q$, ZΔM15, proA$^+$B$^+$ (Zell, R., and Fritz, H. -J. (1987) EMBO J. 6:1809–1815); ATCC 68616—*E. coli* GM33 which carries plasmid pCB13C, an ampicillin-resistant derivative of Pharmacia plasmid vector pTZ19R (Pharmacia) that contains the ATCC 53926 alkaline protease-ClaI fusion gene. The GM33 strain's genotype is dam3 (dam-methylase minus (Marinus, M. G. and Norris, N. R. (1974) J. Mol. Biol. 85:309–322)); ATCC 68617—*E. coli* WK6 which carries phasmid pMa5-8, an ampicillin-resistant mutagenesis vector described in Stanssens, P. et al. (1989) Nucleic Acids Research 17:4441–4454. The genotype of strain WK6 mutations are Δlac-proAB, galE, strA, mutS::Tn10/F'lacI$^q$, ZΔM15, ProA$^+$B$^+$(Zell, R., and Fritz, H. -J. (1987) EMBO J. 6:1809–1815); ATCC 68618—an *E. coli* WK6 which carries phasmid pMc5-8, a chloramphenicol-resistant mutagenesis vector described in Stanssens, P., et al. (1989) Nucleic Acids Res. 17:4441–4454. The genotype of strain WK6 are Δlac-proAB, galE, strA, mutS::Tn10/F'lacI$^q$, ZΔM15, proA$^+$B$^+$ (Zell, R., and Fritz, H. -J. (1987) EMBO J. 6:1809–1815).

What is claimed is:

1. A mutant *Bacillus lentus* DSM 5483 protease derived by the replacement of at least one amino acid residue of the mature form of the *Bacillus lentus* DSM 5483 alkaline protease shown in SEQ ID NO: 52 wherein said at least one amino acid residue is selected from the group consisting of, Asn42, Ala47, Glu87, Ala96, Asn114, His118, Ser130, Thr141, Ser142 and Asn237, wherein the mutant protease has increased thermal stability relative to the mature form of the protease shown in SEQ ID NO: 52.

2. A mutant *Bacillus lentus* DSM 5483 protease of claim 1 wherein the glutamic acid residue at position 87 is substituted by arginine.

3. A mutant *Bacillus lentus* DSM 5483 protease of claim 1 wherein the asparagine residue at position 114 is substituted by serine.

4. A mutant *Bacillus lentus* DSM 5483 protease of claim 1 wherein the alanine residue at position 47 is substituted by tryptophan.

5. A mutant *Bacillus lentus* DSM 5483 protease of claim 1 wherein the serine residue at position 130 is substituted by alanine.

6. A mutant *Bacillus lentus* DSM 5483 protease of claim 1 wherein the serine residue at position 130 is substituted by threonine.

7. A mutant *Bacillus lentus* DSM 5483 protease of claim 1 wherein the alanine residue at position 96 is substituted by isoleucine.

8. A mutant *Bacillus lentus* DSM 5483 protease of claim 1 wherein the serine residue at position 142 is substituted by threonine.

9. A mutant *Bacillus lentus* DSM 5483 protease of claim 1 wherein the alanine residue at position 96 is substituted by asparagine.

10. A mutant *Bacillus lentus* DSM 5483 protease of claim 1 wherein the asparagine residue at position 42 is substituted by phenylalanine.

11. A mutant *Bacillus lentus* DSM 5483 protease of claim 1 wherein the serine residue at position 142 is substituted by alanine.

12. A mutant *Bacillus lentus* DSM 5483 protease of claim 1 wherein the histidine residue at position 118 is substituted by phenylalanine.

13. A mutant *Bacillus lentus* DSM 5483 protease of claim 1 wherein the asparagine residue at position 237 is substituted by alanine.

14. A mutant *Bacillus lentus* DSM 5483 protease of claim 1 wherein the asparagine residue at position 237 is substituted by alanine and the threonine residue at position 141 is substituted by tryptophan.

15. A mutant *Bacillus lentus* DSM 5483 protease of claim 1 wherein the threonine residue at position 141 is substituted by tryptophan.

16. A mutant gene which encodes for a mutant *Bacillus lentus* DSM 5483 protease comprising in the direction of transcription of a promoter, ribosomal binding site, initiation codon and the major portion of the pre region of the *Bacillus licheniformis* ATCC 53926 alkaline protease gene operably linked to a portion of the pre region and all of the pro and mature regions of the *Bacillus lentus* DSM 5483 alkaline protease gene wherein one or more codons of said *Bacillus lentus* DSM 5483 alkaline protease gene are altered to produce a mutant gene which encodes for a mutant protease derived by the replacement of at least one amino acid residue of the mature form of the *Bacillus lentus* DSM 5483 alkaline protease wherein said at least one amino acid residue is selected from the group consisting of Ser3, Asn42, Ala47, Glu87, Ala96, Asn114, His118, Ser130, Thr141, Ser142 and Asn237, wherein the mutant protease has increased thermal stability relative to the mature form of the protease shown in SEQ ID NO: 52.

17. The mutant gene of claim 16 which encodes for said mutant protease wherein the serine residue at position 3 is substituted by threonine and the substitution at position 3 is the only substitution in the *Bacillus lentus* DSM 5483 protease.

18. The mutant gene of claim 16 which encodes for said mutant protease wherein the glutamic acid residue at position 87 is substituted by arginine.

19. The mutant gene of claim 16 which encodes for said mutant protease wherein the asparagine residue at position 114 is substituted by serine.

20. The mutant gene of claim 16 which encodes for said mutant protease wherein the alanine residue at position 47 is substituted by tryptophan.

21. The mutant gene of claim 16 which encodes for said mutant protease wherein the serine residue at position 130 is substituted by alanine.

22. The mutant gene of claim 16 which encodes for said mutant protease wherein the serine residue at position 130 is substituted by threonine.

23. The mutant gene of claim 16 which encodes for said mutant protease wherein the alanine residue at position 96 is substituted by isoleucine.

24. The mutant gene of claim 16 which encodes for said mutant protease wherein the serine residue at position 142 is substituted by threonine.

25. The mutant gene of claim 16 which encodes for said mutant protease wherein the alanine residue at position 96 is substituted by asparagine.

26. The mutant gene of claim 16 which encodes for said mutant protease wherein the asparagine residue at position 42 is substituted by phenylalanine.

27. The mutant gene of claim 16 which encodes for said mutant protease wherein the serine residue at position 142 is substituted by alanine.

28. The mutant gene of claim 16 which encodes for said mutant protease wherein the histidine residue at position 118 is substituted by phenylalanine.

29. The mutant gene of claim 16 which encodes for said mutant protease wherein the asparagine residue at position 237 is substituted by alanine.

30. The mutant gene of claim 16 which encodes for said mutant protease wherein the asparagine residue at position 237 is substituted by alanine and the threonine residue at position 141 is substituted by tryptophan.

31. The mutant gene of claim 16 which encodes for said mutant protease wherein the threonine residue at position 141 is substituted by tryptophan.

32. A hybrid plasmid capable of replication in Bacillus including of a gene which encodes for a mutant *Bacillus lentus* DSM 5483 protease comprising in the direction of transcription a promoter, ribosomal binding site, initiation codon and the major portion of the pre region of the *Bacillus licheniformis* ATCC 53926 alkaline protease gene operably linked to a portion of the pre region and all of the pro and mature regions of the *Bacillus lentus* DSM 5483 alkaline protease gene followed by a 164 bp DNA fragment containing the transcription terminator from the ATCC 53926 alkaline protease gene wherein one or more codons of said *Bacillus lentus* DSM 5483 alkaline protease gene are altered to produce a mutant gene which encodes for a mutant protease derived by the replacement of at least one amino acid residue of the mature form of the *Bacillus lentus* DSM 5483 alkaline protease wherein said at least one amino acid residue is selected from the group consisting of Ser3, Asn42, Ala47, Glu87, Ala96, Asn114, His118, Ser130, Thr141, Ser142 and Asn237, wherein the mutant protease has increased thermal stability relative to the mature form of protease shown in SEQ ID NO: 52.

33. The hybrid plasmid of claim 32 wherein said mutant gene encodes for said mutant protease wherein the serine residue at position 3 is substituted by threonine and the substitution at position 3 is the only substitution in the *Bacillus lentus* DSM 5483 protease.

34. The hybrid plasmid of claim 32 wherein said mutant gene encodes for said mutant protease wherein the glutamic acid residue at position 87 is substituted by arginine.

35. The hybrid plasmid of claim 32 wherein said mutant gene encodes for said mutant protease wherein the asparagine residue at position 114 is substituted by serine.

36. The hybrid plasmid of claim 32 wherein said mutant gene encodes for said mutant protease wherein the alanine residue at position 47 is substituted by tryptophan.

37. The hybrid plasmid of claim 32 wherein said mutant gene encodes for said mutant protease wherein the serine residue at position 130 is substituted by alanine.

38. The hybrid plasmid of claim 32 wherein said mutant gene encodes for said mutant protease wherein the serine residue at position 130 is substituted by threonine.

39. The hybrid plasmid of claim 32 wherein said mutant gene encodes for said mutant protease wherein the alanine residue at position 96 is substituted by isoleucine.

40. The hybrid plasmid of claim 32 wherein said mutant gene encodes for said mutant protease wherein the serine residue at position 142 is substituted by threonine. isoleucine residue at position 102 is substituted by tryptophan.

41. The hybrid plasmid of claim 32 wherein said mutant gene encodes for said mutant protease wherein the alanine residue at position 96 is substituted by asparagine.

42. The hybrid plasmid of claim 32 wherein said mutant gene encodes for said mutant protease wherein the asparagine residue at position 42 is substituted by phenylalanine.

43. The hybrid plasmid of claim 32 wherein said mutant gene encodes for said mutant protease wherein the serine residue at position 142 is substituted by alanine.

44. The hybrid plasmid of claim 32 wherein said mutant gene encodes for said mutant protease wherein the histidine residue at position 118 is substituted by phenylalanine.

45. The hybrid plasmid of claim 32 wherein said mutant gene encodes for said mutant protease wherein the asparagine residue at position 237 is substituted by alanine.

46. The hybrid plasmid of claim 32 wherein said mutant gene encodes for said mutant protease wherein the asparagine residue at position 237 is substituted by alanine and the threonine residue at position 141 is substituted by tryptophan.

47. The hybrid plasmid of claim 32 wherein said mutant gene encodes for said mutant protease wherein the threonine residue at position 141 is substituted by tryptophan.

48. A mutant *Bacillus lentus* DSM 5483 protease derived by the replacement of at least one amino acid residue of the mature form of the *Bacillus lentus* DSM 5483 alkaline protease shown in SEQ ID NO: 52 wherein said at least one amino acid residue is selected from the group consisting of Asn42, Asn114, Ser130, Thr141, Ser142 and Asn237.

* * * * *